(12) United States Patent
Khademosseini et al.

(10) Patent No.: US 11,083,780 B2
(45) Date of Patent: Aug. 10, 2021

(54) SHEAR-THINNING COMPOSITIONS AS AN INTRAVASCULAR EMBOLIC AGENT

(71) Applicants: The Brigham and Women's Hospital, Inc., Boston, MA (US); The General Hospital Corporation, Boston, MA (US)

(72) Inventors: Ali Khademosseini, Cambridge, MA (US); Rahmi Oklu, Scottsdale, AZ (US)

(73) Assignees: The Brigham and Women's Hospital, Inc., Boston, MA (US); The General Hospital Corporation, Boston, MA (US)

(*) Notice: Subject to any disclaimer, the term of this patent is extended or adjusted under 35 U.S.C. 154(b) by 239 days.

(21) Appl. No.: 15/746,307

(22) PCT Filed: Jul. 20, 2016

(86) PCT No.: PCT/US2016/043099
§ 371 (c)(1),
(2) Date: Jan. 19, 2018

(87) PCT Pub. No.: WO2017/069822
PCT Pub. Date: Apr. 27, 2017

(65) Prior Publication Data
US 2018/0360920 A1    Dec. 20, 2018

Related U.S. Application Data

(60) Provisional application No. 62/194,644, filed on Jul. 20, 2015.

(51) Int. Cl.
*A61K 38/39* (2006.01)
*A61P 7/00* (2006.01)
*A61K 9/00* (2006.01)
*A61K 9/06* (2006.01)
*A61K 47/02* (2006.01)

(52) U.S. Cl.
CPC ............ *A61K 38/39* (2013.01); *A61K 9/0019* (2013.01); *A61K 9/06* (2013.01); *A61K 47/02* (2013.01); *A61P 7/00* (2018.01)

(58) Field of Classification Search
CPC .......... A61K 38/39; A61K 47/02; A61K 9/06; A61K 9/0019; A61P 7/00
See application file for complete search history.

(56) References Cited

U.S. PATENT DOCUMENTS

| | | | |
|---|---|---|---|
| 5,785,955 | A | 7/1998 | Fischer |
| 7,670,623 | B2 | 3/2010 | Kotha et al. |
| 8,106,030 | B2 | 1/2012 | Hardy et al. |
| 8,304,595 | B2 | 11/2012 | Daniels et al. |
| 8,703,208 | B2 | 4/2014 | Liu et al. |
| 2003/0108575 | A1 | 6/2003 | Lu |
| 2004/0157953 | A1 | 8/2004 | Porter |
| 2004/0197302 | A1 | 10/2004 | Porter et al. |
| 2006/0018966 | A1 | 1/2006 | Lin et al. |
| 2007/0154510 | A1 | 7/2007 | Wilcher et al. |
| 2010/0055167 | A1* | 3/2010 | Zhang ............... A61K 9/0085 424/450 |
| 2011/0171308 | A1 | 7/2011 | Zhang et al. |
| 2011/0275572 | A1 | 11/2011 | Rafailovich |
| 2013/0289131 | A1 | 10/2013 | Segal |
| 2014/0348959 | A1 | 11/2014 | Mitchnick et al. |

FOREIGN PATENT DOCUMENTS

| | | |
|---|---|---|
| CA | 2635379 | 4/2014 |
| CN | 102321255 | 1/2012 |
| EP | 1983951 | 10/2008 |
| EP | 2123309 | 11/2009 |
| WO | WO 2004/075989 | 9/2004 |
| WO | WO 2007/074326 | 7/2007 |
| WO | WO 2012/016695 | 2/2012 |
| WO | WO 2012/040331 | 3/2012 |
| WO | WO 2012/075087 | 6/2012 |
| WO | WO 2014/205261 | 12/2014 |
| WO | 2015/143148 | 9/2015 |

OTHER PUBLICATIONS

International Search Report and Written Opinion dated May 23, 2017 in international application No. PCT/US2016/043099, 17 pgs.
European Search Report and Written Opinion in Application No. 16857928.2, dated Feb. 21, 2019, 8 pages.
Assmann et al., "Acceleration of autologous in vivo recellularization of decellularized aortic conduits by fibronectin surface coating," Biomaterials, Aug. 2013, 34(25):6015-6026.
Cha et al., "Microfluidics-assisted fabrication of geletatin-silica core-shell nnicrogels for injectable tissue constructs," Biomacromolecules, 2014, 15(1): 283-290.
Dawson and Oreffo, "Clay: New Opportunities for Tissue Regeneration and Biomaterial Design," Adv. Mater, 2013, 25:4069-4086.
Huebsch et al, "Analysis of sterilization protocols for peptide-modified hydrogels," J. Biomed. Mater. Res. Part B Appl. Biomater, 2005, 74B:440-447.
International Preliminary Report on Patentability in International Application No. PCT/US16/43099, dated Feb. 23, 2018, 35 pages.
International Preliminary Report on Patentability dated Dec. 22, 2015 in international application No. PCT/US14/43251, 8 pgs.
International Search Report and Written Opinion dated Oct. 16, 2014 in international application No. PCT/US14/43251, 12 pgs.
Klebanoff, "Myeloperoxidase: friend and foe," J. Leukoc. Biol. 2005, 77:598-625.
Kumar et al., "A nanostructured synthetic collagen mimic for hemostasis," Biomacromolecules, 2014, 15:1484-1490.

(Continued)

*Primary Examiner* — Matthew P Coughlin
*Assistant Examiner* — Thurman Wheeler
(74) *Attorney, Agent, or Firm* — Fish & Richardson P.C.

(57) ABSTRACT

This disclosure relates to methods of using shear-thinning compositions in the treatment of a vascular disorders, cancers, infections, abscesses, and fistulas.

15 Claims, 28 Drawing Sheets

(56) References Cited

OTHER PUBLICATIONS

Li et al., "Cytotoxicity and potency of mesocellular foam-26 in comparison to layered clays used as hemostatic agents," Toxicol. Res., 2013, 2:136-144.
Liu et al., "The improvement of hemostatic and wound healing property of chitosan by halloysite nanotubes," RSC Adv., 2014, 4:23540-23553.
Lopera et al, "Embolization in trauma: principles and techniques," Semin. Intervent. Radiol, Mar. 2010, 27:14-28.
Marques et al, "Simulated Biological Fluids with Possible Application in Dissolution Testing," Dissolution Technol, 2011, 18:15-28.
Trampuz et al, "Effect of gamma irradiation on viability and DNA of *Staphylococcus epidermidis* and *Escherichia coli*," J. Med. Microbiol. 2006, 55:1271-1275.

\* cited by examiner

6D

6E

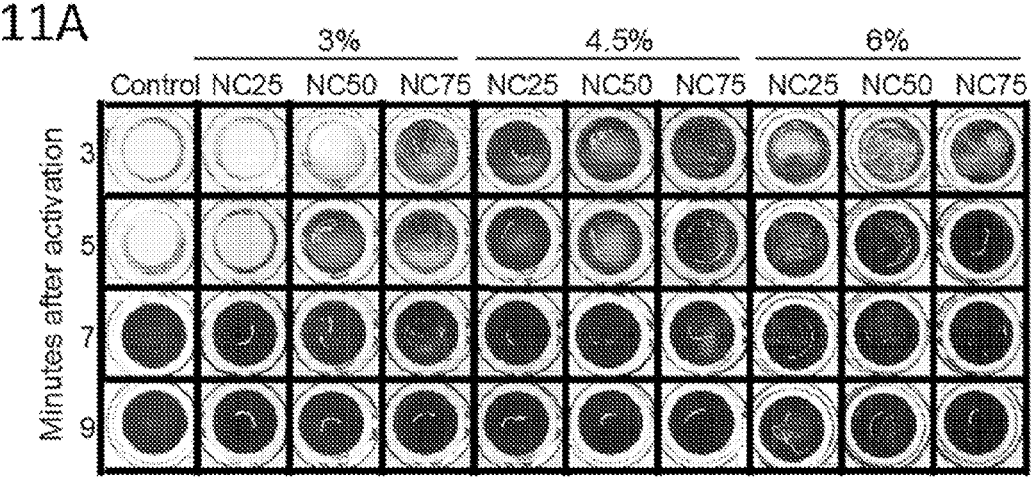
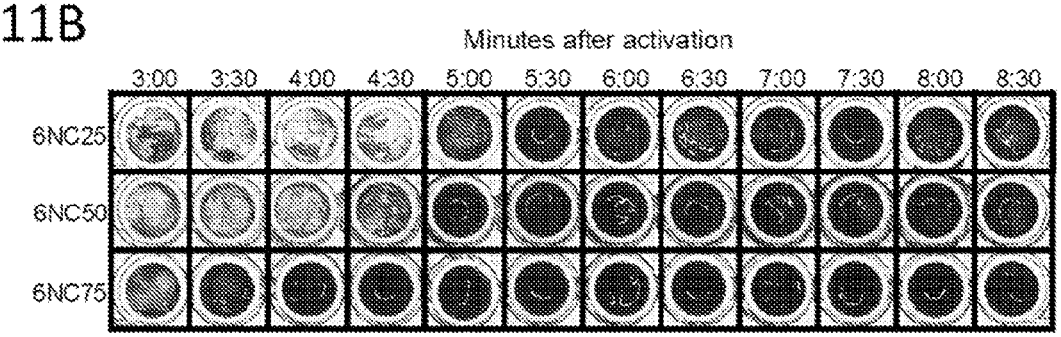
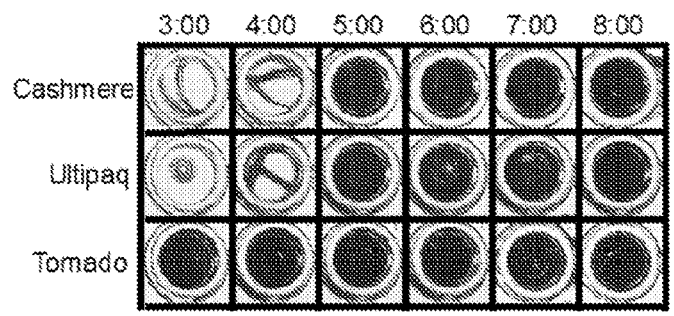
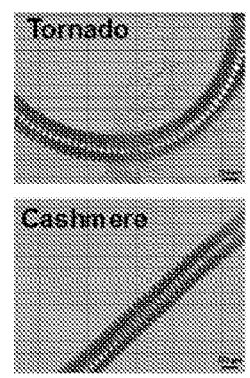
FIGs. 11A-11C

12A

12B

SHEAR-THINNING COMPOSITIONS AS AN INTRAVASCULAR EMBOLIC AGENT

CROSS-REFERENCE TO RELATED APPLICATIONS

This application is a § 371 National Stage Application of PCT/US2016/043099, filed Jul. 20, 2016, which claims the benefit of U.S. Provisional Application Ser. No. 62/194,644, filed Jul. 20, 2015, the disclosure of each of which is incorporated herein by reference in its entirety.

FEDERALLY SPONSORED RESEARCH OR DEVELOPMENT

This invention was made with Government support under Grant Nos. NIH/NIGMS 5T32GM008334, 1K99CA201603-01A1, EB012597, AR057837, DE021468, HL099073, AI105024, AR063745, EB021148, and CA172738, awarded by the National Institutes of Health, Grant No. W911NF-13-D-0001, awarded by the U.S. Army Research Office, and Grant No. EFRI-1240443, awarded by the National Science Foundation. The Government has certain rights in the invention.

TECHNICAL FIELD

This disclosure relates to methods of using shear-thinning compositions, and more particularly to methods of using shear-thinning compositions for the treatment of vascular pathologies, and additional diseases or disorders including cancer, infections, and abscesses.

BACKGROUND

The past half-century has witnessed development in the use of minimally invasive, endovascular techniques in medicine. Interventions predicated upon real-time image guidance to direct flexible catheters from an easily accessible, superficial blood vessel to a remote blood vessel deep within the body have revolutionized the clinical management of diseases involving many organs. A common paradigm in endovascular procedures is the performance of vascular embolization, a technique in which an occlusive agent is delivered through a catheter to obstruct flow within a target blood vessel.

SUMMARY

The present application provides, inter alia, a method of treating an aneurysm in a subject in need thereof, comprising administering to the subject a therapeutically effective amount of a shear-thinning composition. In some embodiments, the aneurysm is a saccular, fusiform or mycotic aneurysm or a pseudoaneurysm. In some embodiments, the aneurysm is selected from the group consisting of an idiopathic aneurysm, an iatrogenic aneurysm, a traumatic aneurysm, infectious aneurysm, and an atherosclerotic aneurysm. In some embodiments, the aneurysm is selected from the group consisting of cerebral aneurysm, aortic aneurysm, ventricular aneurysm, renal aneurysm, abdominal aneurysm, splenic, hepatic, mesenteric artery, gastric, femoral, popliteal, brachial, and pancreaticoduodenal arcade aneurysm. In some embodiments, the treating comprises administering the shear-thinning composition into the arterial or venous aneurysm. In some embodiments, the treating comprises administering the shear-thinning composition into the aneurysm in an amount effective to prevent rupture of the aneurysm, aneurysm growth, recanalization, or any combination thereof.

The present application further provides a method of treating a hemorrhage in a subject in need thereof, comprising administering to the subject a therapeutically effective amount of a shear-thinning composition. In some embodiments, the hemorrhage is an internal hemorrhage. In some embodiments, the hemorrhage is selected from the group consisting of an internal Class I hemorrhage, an internal Class II hemorrhage, an internal Class III hemorrhage, and an internal Class IV hemorrhage. In some embodiments, the hemorrhage is selected from the group consisting of arterial gastrointestinal hemorrhage, venous gastrointestinal hemorrhage, liver hemorrhage, spleen hemorrhage, stomach hemorrhage, kidney hemorrhage, pulmonary hemorrhage, small bowel hemorrhage, large bowel hemorrhage, lower limb/upper limb hemorrhage, intracranial hemorrhage, intracerebral hemorrhage, and subarachnoid hemorrhage.

In some embodiments, the hemorrhage is an internal hemorrhage associated with a medical disorder or a trauma. In some embodiments, the medical disorder comprises a gastrointestinal disorder. In some embodiments, the medical disorder selected from the group from the group consisting of an ulcer, a varix, esophagitis, gastritis, erosion, diverticular disease, vascular ectasia, ischemic colitis, infectious colitis, inflammatory bowel disease. In some embodiments, the medical disorder comprises benign cancer, malignant cancer, metastatic cancer, or any combination thereof. In some embodiments, the cancer is selected from the group consisting of breast cancer, prostate cancer, benign prostatic hyperplasia, esophageal cancer, liver cancer, colon cancer, endometrial cancer, brain cancer, bladder cancer, cancer of the uterus, fibroid (leiomyoma) uterus, cancer of the ovary, lung cancer, sarcoma, bone cancer, pancreatic cancer, renal cancer, and stomach cancer. In some embodiments, the trauma comprises blunt trauma, an abrasion, an avulsion, an incision, a laceration, a puncture, a penetration, surgical trauma, iatrogenic trauma, or any combination thereof.

In some embodiments, the treating comprises locally administering the shear-thinning composition at the site of the hemorrhage. In some embodiments, the treating comprises locally administering the shear-thinning composition at the site of the hemorrhage in an amount effective to reduce or stop bleeding of the hemorrhage. In some embodiments, the administration is endovascular or percutaneous administration.

The present application further provides a method of treating a venous congestion disorder in a subject in need thereof, comprising administering to the subject a therapeutically effective amount of a shear-thinning composition. In some embodiments, the venous congestion disorder is selected from the group consisting of pelvic congestion syndrome, chronic venous insufficiency, lower extremity varicose veins, hemorrhoids, and congested or distended mesenteric veins. In some embodiments, the treating comprises locally administering the shear-thinning composition at the site of the venous congestion disorder. In some embodiments, the treating comprises locally administering the shear-thinning composition at the site of the venous congestion disorder in an amount effective to occlude a blood vessel in the subject.

The present application further provides a method of treating a varix in a subject in need thereof, comprising administering to the subject a therapeutically effective amount of a shear-thinning composition. In some embodiments, the varix is selected from the group consisting of a varicose vein, an arterial varix, or a lymphatic varix. In some embodiments, the varix is associated with portal hypertension. In some embodiments, the treating comprises locally administering the shear-thinning composition at the site of the varix in an amount effective to occlude the varix.

The present application further provides a method of treating an abscess or fistula in a subject in need thereof, comprising administering to the subject a therapeutically effective amount of a shear-thinning composition and an additional therapeutic agent, an additional diagnostic agent, or a combination thereof. In some embodiments, the treating comprises locally administering the shear-thinning composition at the site of the abscess or fistula in an amount effective to substantially fill the abscess or fistula.

In some embodiments, the additional therapeutic or diagnostic agent is selected from the group consisting of an antimicrobial agent, an antifungal agent, an anti-inflammatory agent, an adhesive agent, a regenerative agent, a hemostatic agent, a magnetic agent, an electrical agent, a biosensor for bacteria to enable treatment monitoring, or any combination thereof. In some embodiments, the additional therapeutic agent is preloaded onto at least one surface of the shear-thinning composition prior to the treating. In some embodiments, the additional therapeutic agent is preloaded into the shear-thinning composition prior to the treating. In some embodiments, the additional therapeutic agent is released from the shear-thinning composition upon contacting the abscess with the shear-thinning composition.

The present application further provides a method of treating cancer in a subject in need thereof, comprising administering to the subject a therapeutically effective amount of a shear-thinning composition and an additional agent. In some embodiments, the cancer is selected from the group consisting of breast cancer, prostate cancer, benign prostatic hyperplasia, esophageal cancer, liver cancer, colon cancer, endometrial cancer, brain cancer, bladder cancer, cancer of the uterus, fibroid (leiomyoma) uterus, cancer of the ovary, lung cancer, sarcoma, bone cancer, pancreatic cancer, renal cancer, and stomach cancer. In some embodiments, the cancer comprises a solid tumor.

In some embodiments, the additional agent is selected from the group consisting of a chemotherapeutic agent, a diagnostic agent, a biosensor, and a sensitizing drug to an adjuvant therapy. In some embodiments, the additional agent preloaded onto at least one surface of the shear-thinning composition prior to the treating. In some embodiments, the additional agent preloaded into the shear-thinning composition prior to the treating. In some embodiments, the additional agent is released from the shear-thinning composition upon contacting the cancer with the shear-thinning composition.

The present application further provides a method of treating an infection in a subject in need thereof, comprising administering to the subject a therapeutically effective amount of a shear-thinning composition and an additional therapeutic agent. In some embodiments, the infection selected from the group consisting of a bacterial infection, a fungal infection, parasitic infection and a viral infection.

In some embodiments, the additional therapeutic agent is selected from the group consisting of an antibacterial agent, an antifungal agent, anti-parasitic agent, an anti-viral agent, an anti-inflammatory agent, a steroid, or any combination thereof. In some embodiments, the additional therapeutic agent is an antibacterial agent.

In some embodiments, the administering comprises injecting the shear-thinning composition into the subject. In some embodiments, the administering is performed using a catheter or a syringe. In some embodiments, the administration comprises an image guided endovascular procedure or an image guided percutaneous procedure.

In some embodiments, the shear-thinning composition is preloaded onto at least one surface of a medical device prior to the treating. In some embodiments, the shear-thinning composition is preloaded into a medical device prior to the treating. In some embodiments, the shear-thinning composition is preloaded into a catheter prior to the treating. In some embodiments, the shear-thinning composition is preloaded into a syringe prior to the treating.

In some embodiments, the shear-thinning composition comprises gelatin or a derivative thereof, and silicate nanoparticles. In some embodiments, the shear-thinning composition comprises about 0.5 percent to about 85 percent by weight of gelatin or a derivative thereof, and silicate nanoparticles together. In some embodiments, the shear-thinning composition comprises about 0.5 percent to about 60 percent by weight of gelatin or a derivative thereof, and silicate nanoparticles together. In some embodiments, the shear-thinning composition comprises about 0.5 percent to about 25 percent by weight of gelatin or a derivative thereof, and silicate nanoparticles together. In some embodiments, the shear-thinning composition comprises about 0.5 percent to about 11 percent by weight of gelatin or a derivative thereof, and silicate nanoparticles together. In some embodiments, the shear-thinning composition comprises about 3 percent to about 11 percent by weight of gelatin or a derivative thereof, and silicate nanoparticles together.

In some embodiments, the shear-thinning composition comprises about 0.5 percent to about 30 percent by weight of the silicate nanoparticles. In some embodiments, the shear-thinning composition comprises about 0.5 percent to about 20 percent by weight of the silicate nanoparticles. In some embodiments, the shear-thinning composition comprises about 0.5 percent to about 10 percent by weight of the silicate nanoparticles. In some embodiments, the shear-thinning composition comprises about 2.25 percent to about 6.75 percent by weight of the silicate nanoparticles. In some embodiments, the shear-thinning composition comprises about 1.5 percent to about 4.5 percent by weight of the silicate nanoparticles. In some embodiments, the shear-thinning composition comprises about 0.75 percent to about 2.25 percent by weight of the silicate nanoparticles.

In some embodiments, the shear-thinning composition comprises about 0.5 percent to about 70 percent by weight of the gelatin or a derivative thereof. In some embodiments, the shear-thinning composition comprises about 0.5 percent to about 60 percent by weight of the gelatin or a derivative thereof. In some embodiments, the shear-thinning composition comprises about 0.5 percent to about 40 percent by weight of the gelatin or a derivative thereof. In some embodiments, the shear-thinning composition comprises about 0.5 percent to about 20 percent by weight of the gelatin or a derivative thereof. In some embodiments, the shear-thinning composition comprises about 0.5 percent to about 10 percent by weight of the gelatin or a derivative thereof. In some embodiments, the shear-thinning composition comprises about 2.25 percent to about 6.75 percent by weight of the gelatin or a derivative thereof. In some embodiments, the shear-thinning composition comprises about 1.5 percent to about 4.5 percent by weight of the gelatin or a derivative thereof. In some embodiments, the shear-thinning composition comprises about 0.75 percent to about 2.25 percent by weight of the gelatin or a derivative thereof.

In some embodiments, the ratio of silicate nanoparticles to gelatin or a derivative thereof, is from about 0.1 to about 1.0.

In some embodiments, the silicate nanoparticles comprise silicate nanoplatelets. In some embodiments, the silicate nanoplatelets comprise a positively charged edge and a negatively charged surface. In some embodiments, the overall charge of the silicate nanoparticles is negative.

In some embodiments, the silicate nanoparticles are from about 5 nm to about 60 nm in diameter. In some embodiments, the silicate nanoparticles are from about 10 nm to about 40 nm in diameter. In some embodiments, the silicate nanoparticles are about 20 to 30 nm in diameter. In some embodiments, the silicate nanoparticles are from about 0.5 nm to about 2 nm in thickness. In some embodiments, the silicate nanoparticles are about 1 nm in thickness.

In some embodiments, the shear-thinning composition comprises a gelatin derivative. In some embodiments, the gelatin derivative is methacrylated gelatin (GelMA), acrylated gelatin, or thiolated gelatin. In some embodiments, the gelatin derivative is methacrylated gelatin (GelMA).

In some embodiments, the shear-thinning composition comprises:

about 6.75 percent by weight gelatin and about 2.25 percent by weight silicate nanoparticles; or about 4.5 percent by weight gelatin and about 4.5 percent by weight silicate nanoparticles; or about 2.25 percent by weight gelatin and about 6.75 percent by weight silicate nanoparticles; or about 4.5 percent by weight gelatin and about 1.5 percent by weight silicate nanoparticles; or about 3 percent by weight gelatin and about 3 percent by weight silicate nanoparticles; or about 1.5 percent by weight gelatin and about 4.5 percent by weight silicate nanoparticles; or about 2.25 percent by weight gelatin and about 0.75 percent by weight silicate nanoparticles; or about 1.5 percent by weight gelatin and about 1.5 percent by weight silicate nanoparticles; or about 0.75 percent by weight gelatin and about 2.25 percent by weight silicate nanoparticles.

In some embodiments, the shear-thinning composition further comprises water. In some embodiments, the shear-thinning composition comprises about 0.5 percent to about 99 percent by weight of the water. In some embodiments, the shear-thinning composition comprises about 30 percent to about 99 percent by weight of the water. In some embodiments, the shear-thinning composition comprises about 50 percent to about 99 percent by weight of the water. In some embodiments, the shear-thinning composition comprises about 70 percent to about 99 percent by weight of the water. In some embodiments, the shear-thinning composition comprises about 90 percent to about 99 percent by weight of the water. In some embodiments, the shear-thinning composition comprises about 80 percent to about 99 percent by weight of the water. In some embodiments, the shear-thinning composition comprises about 90 percent to about 99 percent by weight of the water. In some embodiments, the shear-thinning composition comprises about 91 percent to about 97 percent by weight of the water.

In some embodiments, the shear-thinning composition comprises:

about 6.75 percent by weight gelatin, about 2.25 percent by weight silicate nanoparticles, and about 91 percent by weight water; or about 4.5 percent by weight gelatin, about 4.5 percent by weight silicate nanoparticles, and about 91 percent by weight water; or about 2.25 percent by weight gelatin, about 6.75 percent by weight silicate nanoparticles, and about 91 percent by weight water; or about 4.5 percent by weight gelatin, about 1.5 percent by weight silicate nanoparticles, and about 94 percent by weight water; or about 3 percent by weight gelatin, about 3 percent by weight silicate nanoparticles, and about 94 percent by weight water; or about 1.5 percent by weight gelatin, about 4.5 percent by weight silicate nanoparticles, and about 94 percent by weight water; or about 2.25 percent by weight gelatin, about 0.75 percent by weight silicate nanoparticles, and about 97 percent by weight water; or about 1.5 percent by weight gelatin, about 1.5 percent by weight silicate nanoparticles, and about 97 percent by weight water; or about 0.75 percent by weight gelatin, about 2.25 percent by weight silicate nanoparticles, and about 97 percent by weight water.

In some embodiments, the shear-thinning composition is a gel. In some embodiments, the shear-thinning composition is a hydrogel.

In some embodiments, the gelatin is derived from a mammalian source. In some embodiments, the gelatin is type-A porcine gelatin.

In some embodiments, the yield stress of the shear-thinning composition is from about 1 Pa to about 200 Pa. In some embodiments, the yield stress of the shear-thinning composition is from about 1 Pa to about 100 Pa. In some embodiments, the yield stress of the shear-thinning composition is from about 2 Pa to about 50 Pa. In some embodiments, the yield stress of the shear-thinning composition is from about 1 Pa to about 25 Pa. In some embodiments, the yield stress of the shear-thinning composition is from about 1 Pa to about 10 Pa. In some embodiments, the yield stress of the shear-thinning composition is from about 1 Pa to about 5 Pa. In some embodiments, the shear-thinning composition flows upon application of a pressure greater than the yield stress.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIGS. 11A-11B shows the thrombosis potential of shear-thinning compositions.

FIG. 11C shows thrombosis using clinical metallic coils.

DETAILED DESCRIPTION

Figures 1A, 1B, 1C:
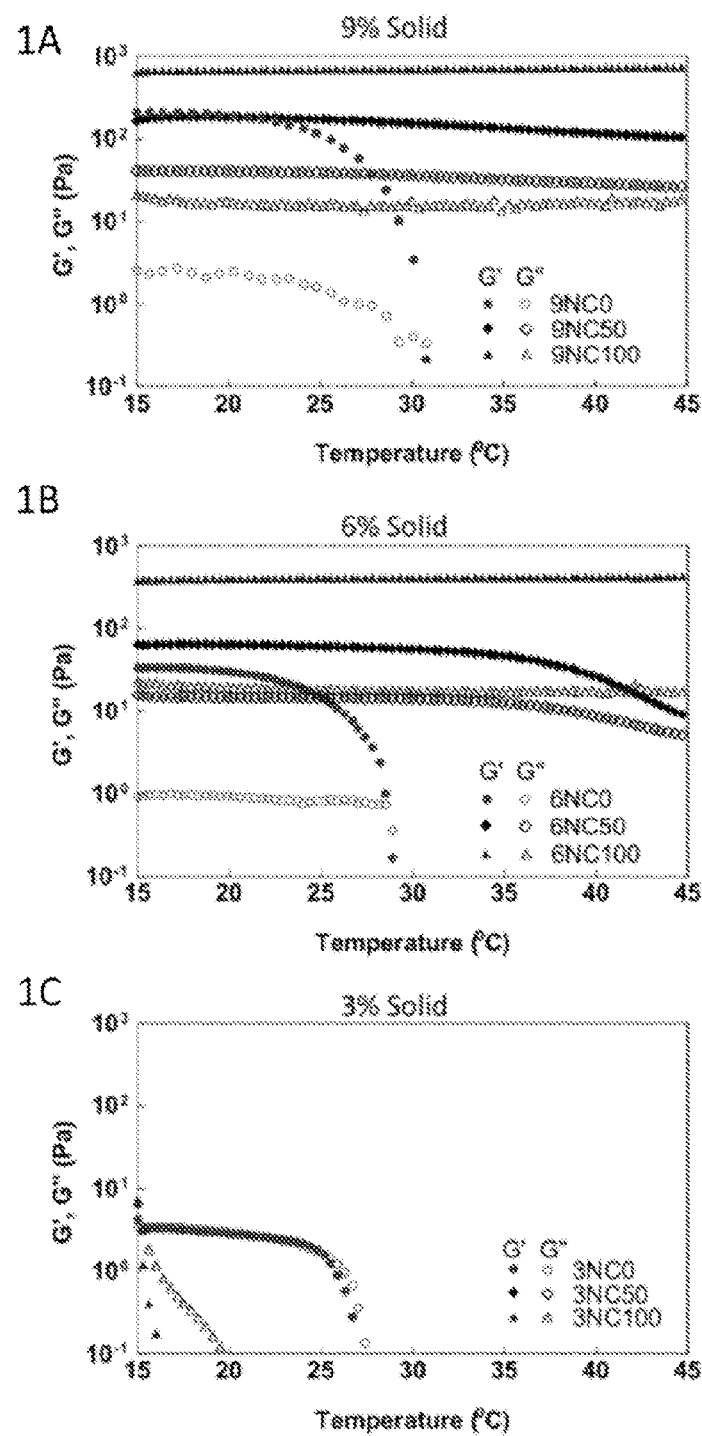
FIG. 1A shows the storage modulus (G') and loss modulus (G") of gelatin and compositions comprising 9 total weight percent solids in a PBS solution from 15° C. to 45° C. at 10 Pa stress and 1 Hz.
FIG. 1B shows the storage modulus (G') and loss modulus (G") of gelatin and compositions comprising 6 total weight percent solids in a PBS solution from 15° C. to 45° C. at 10 Pa stress and 1 Hz.
FIG. 1C shows the storage modulus (G') and loss modulus (G") of gelatin and compositions comprising 3 total weight percent solids in a PBS solution from 15° C. to 45° C. at 10 Pa stress and 1 Hz.

Shear-thinning compositions are able to flow when adequate force is applied to them, similar to commercial products like toothpaste or ketchup. Once the force is removed, the composition is able to recover its properties to remain stable in its new environment, resistant to physiological degradation or mechanical forces that could disrupt the composition.

Technologies used to-date to address hemorrhaging blood vessels include, for example, the use of metallic coils. These metallic coils are costly, generally require the availability of appropriate sizes at the time of procedure, require appropriate catheters to deliver the coils and may require additional devices to deploy the coils, which may be electrical, magnetic or mechanical in nature. Additionally, metallic coils require technical expertise in their use, and may lead to the sacrifice of a vascular bed. Accordingly, there are numerous clinical conditions where shear-thinning compositions could be applicable, which include, but are not limited to:

(1) Embolization of aneurysms. For example, an aneurysm may be embolized using a catheter delivery approach or stent-assisted approach in the treatment of saccular, fusiform or mycotic aneurysms such as those often found in the aorta and its branches. Arterial aneurysm rupture has a very high fatality rate. They can be fusiform or saccular in shape and can occur anywhere in the body. Saccular aneurysms (SAs) carry a greater risk of morbidity and mortality because they are more prone to rupture. Reports suggest an incidence of 6 million for SAs in the brain and 2% in autopsy series for visceral SAs. These aneurysms can be idiopathic, iatrogenic, traumatic, infectious or atherosclerotic in etiology. The current standard of medical practice is primarily to treat aneurysms with minimally-invasive endovascular interventions such as coil embolization and/or stent placement. Coils require a unique set of highly-specialized skills to navigate them within sub-millimeter micro-catheters to distant sites and require precise deployment within fragile aneurysm sacs. As a result, such cases today are very lengthy and expose patients and medical staff to high radiation doses. Endovascular coiling of aneurysms has a high technical success rate; however, coil compaction, aneurysm recanalization and re-treatment are common. Intra-procedural complications have been reported to be up to 15%, recanalization in approximately 40% of cases with half requiring a re-intervention and coil-mass effect or coil compaction has been reported in up to 90% of aneurysm coil-embolization cases.

(2) Embolization of bleeding arteries. For example, a bleeding gastroduodenal artery or gastric artery from an ulcer or tumor, or inferior or superior mesenteric artery bleeding from diverticulitis. Gastrointestinal bleeding (GIB) is often challenging to manage with its intermittent nature, propensity for rebleeding, and vasospasm. The annual incidence of acute GIB is approximately 380,000 per population in the US and 20,000 hospitalized patients die from GIB annually. In combat settings, hemorrhage is the leading cause of mortality with injury to the small bowel and colon alone accounting for 51% of cases. There are many causes of GIB, which include, but are not limited to, ulcers, varices, esophagitis, gastritis, erosions, diverticular disease, vascular ectasia, ischemic colitis, infectious colitis, inflammatory bowel disease, and neoplasm.

(3) Injection into tumors. Shear-thinning compositions can be tailored for bland or chemoembolization to achieve ischemia and delivery of chemotherapeutic agents to a tumor. For example, liver, renal, lung, fibroids, benign prostatic hyperplasia, prostate and metastatic tumors may be treated by arterial embolization of blood vessels that supply the neoplasm. The shear-thinning compositions provided herein may also be used as a carrier of drugs such as chemotherapy agents or additional therapeutic agents.

(4) Treatment of infectious cavities. For example, infectious abscesses and fistulas or infectious aneurysms such mycotic aneurysms may be filled with shear-thinning compositions. Further, the shear-thinning compositions provided herein may also be used as a carrier of additional therapeutic agents to aid in the treatment and healing of infectious cavities, including, but not limited to, antimicrobial agents, adhesive agents, anti-inflammatory agents, regenerative agents, and hemostatic agents.

(5) Organ Displacement. The shear-thinning compositions provided herein may be used for displacing one or more organs, for example, during a surgical procedure. For example, the shear-thinning composition may be administered to displace a solid organ to enable safe needle access to a target for biopsy under computed tomography, ultrasound or flurosocopy guidance. The shear-thinning compositions provided herein may also be injected between two solid organs to act as a heat-sink, thereby preventing injury to adjacent structures when tissue is thermally ablated during a surgical procedure. A non-limiting example includes the shear-thinning composition being injected between the diaphragm and the liver of a subject to enable safe ablation of liver tumors near the liver surface, thereby protecting the diaphragm from the ablation procedure and minimizing pain symptoms in the subject. A further non-limiting example includes injecting the shear-thinning composition between the kidneys and large bowel of the subject to protect the bowel from injury when kidney tumors are ablated.

Additional uses of shear-thinning compositions include, but are not limited to the occlusion of abnormal veins, for example, congested gastric and esophageal veins resulting from portal hypertension or from pelvic congestion syndrome and treatment of varicose veins. Shear-thinning compositions may be delivered via percutaneous approach such as a needle or maybe navigated to region of interest within the vasculature via endovascular approach.

In a previous study, shear-thinning compositions were assessed for rheological behavior, physiological stability, and activity (see e.g., International Publication No. WO 2014/205261). Although the application of the shear-thinning composition on rat liver surface was hemostatic in nature, the study did not require injectable shear-thinning behavior and therefore a concentrated formulation was tested. In contrast, endovascular embolization and other small bore catheter based applications require easy injectability through long catheters (up to 150 cm), rapid gelation to create an occlusive seal of the arterial lumen without fragmentation, a formulation that does not cause CT, MRI or US artifact and a gamma irradiated material that is sterile and easy to use. These conditions were not previously assessed or characterized, supporting further investigations into the suitability of the new shear-thinning composition formulations with enhanced properties as injectable hydrogel embolic agents. Indeed, the shear-thinning compositions form a complete, impenetrable cast of the vessel after injection, which is sufficient to occlude the vessel or the aneurysm without relying on thrombosis.

Accordingly, the present application provides methods of treating a variety of vascular pathologies in a patient by administering shear-thinning compositions. Vascular pathologies that may be treated with the compositions provided herein may include, but are not limited to, aneurysms, hemorrhages, (e.g., internal hemorrhages, hemorrhages associated with cancer, hemorrhages associated with trauma, and the like), gastrointestinal disorders (e.g. gastrointestinal bleeding, ulcers, gastritis, and the like), cancer (e.g., arterial embolization of solid tumors), venous congestion disorders (e.g., pelvic congestion syndrome and chronic venous insufficiency), varices (e.g., varicose veins), and abcesses or fistulas. In some embodiments, the compositions provided herein may be administered in combination with an additional therapeutic agent for the treatment of a disease or disorder in a patient. Example diseases and disorders include, but are not limited to, vascular pathologies provided herein, a cancer, an infection, an abscess, or a fistula. In some embodiments the compositions provided herein are injectable and can be administered via a catheter. In some embodiments, the compositions provided herein form a physiologically stable artificial matrix and can promote the natural clotting cascade. For example, the compositions provided herein flow with minimal applied pressure during injection, providing a method of application that avoids additional patient trauma. Moreover, in some embodiments, the compositions provided herein, once applied to a treatment site, solidify to prevent biomaterial loss (e.g., blood loss) to unaffected areas.

Definitions

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "therapeutically effective amount" of a composition with respect to the subject method of treatment, refers to an amount of the composition(s) in a preparation which, when administered as part of a desired dosage regimen (to a patient or a subject, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting one or more of the symptoms, clinical signs, and underlying pathology of a condition in a manner to improve or stabilize a patient's condition.

As used herein, the term "medical condition" refers to a condition or disorder in a subject who is experiencing or displaying the pathology or symptomatology of a disease, condition, or disorder (i.e., symptoms), for example, pain, dysfunction, or distress. It is understood that one of ordinary skill (e.g., a clinician, physician, veterinarian, and the like), is able to diagnose a medical condition.

As used herein, the term "vascular condition" refers to a condition or disorder in a subject related to the vascular system of the subject (i.e., the circulatory system). Example vascular conditions may include, but are not limited to, an aneurysm, a hemorrhage, a venous congestion disorder, a varix, an abscess, a fistula, a cancer, and an infection.

As used here, the term "locally administering" refers to administration at or within close proximity to a vascular condition in a subject. For example, upon cessation of the administration, a shear-thinning composition provided herein will remain substantially localized at the site of the administration. In some embodiments, a shear-thinning composition provided herein is locally administered at the site of a vascular condition (e.g., administered within abscess, administered within a tumor, administered within an aneurysm, and the like).

Shear-Thinning Compositions

The present application provides shear-thinning compositions. The expression "shear-thinning" or "shear-thinning behavior", refers to a decrease in viscosity (i.e., increasing flow rate) of a composition with increasing application of shear stress. For example, a shear-thinning composition (i.e. a composition exhibiting shear-thinning behavior) can exhibit a decrease in viscosity (i.e. increase in flow) upon application of an increasing rate of shear stress. As shown in Example 6, shear-thinning behavior was not observed in the individual components of exemplary compositions (e.g., gelatin, 9NC0), but was observed in the compositions upon combination of the components (e.g., a composition comprising both gelatin and silicate nanoparticles (e.g., 9NC75)).

In some embodiments, a shear-thinning composition provided herein comprises gelatin or a derivative thereof, and silicate nanoparticles. As used herein, the term "gelatin", alone or in combination with other terms, refers to a mixture of proteins and peptides derived from the partial hydrolysis or denaturing of collagen. The intermolecular, intramolecular, and hydrogen bonds which stabilize collagen proteins and peptides are broken down to form gelatin, for example, by acid hydrolysis, alkali hydrolysis, or enzymatic hydrolysis. In some embodiments, the gelatin may be derived from a mammalian source. Examples of such gelatins include, but are not limited to porcine gelatin (e.g., type-A porcine gelatin, gelatin derived from porcine skin, gelatin derived from porcine bones, and the like), bovine gelatin (e.g., gelatin derived from bovine skin, type B bovine gelatin, gelatin derived from bovine bones, and the like), and equine gelatin.

In some embodiments, the shear-thinning compositions provided herein comprise a gelatin derivative. As used here, the term "gelatin derivative", alone or in combination with other terms, refers to gelatin that has been reacted with various types of reagents to functionalize the gelatin (e.g., methacrylated gelatin (GelMA), acrylated gelatin, thiolated gelatin). For example, derivatives of gelatin may be prepared by reacting gelatin with an acid anhydride or acid chloride, including, but not limited to, phthalic anhydride, maleic anhydride, succinic anhydride, benzoic anhydride, isatoic anhydride, methacrylic anhydride, 3,4-dibromo phthalic anhydride, benzoyl chloride, p-nitro benzoyl chloride, 1-hydroxy-2-naphthoyl chloride, o-hydroxy benzoyl chloride, phthalyl chloride, and ethyl chlorocarbonate. In some embodiments, the shear-thinning compositions provided herein comprise methacrylated gelatin (GelMA), acrylated gelatin, or thiolated gelatin.

In some embodiments, the shear-thinning compositions provided herein comprise about 0.5 percent to about 70 percent by weight of gelatin or a derivative thereof, for example, from about 0.5 percent to about 60 percent by weight, about 0.5 percent to about 40 percent by weight, about 0.5 percent to about 20 percent by weight, about 0.5 percent to about 10 percent by weight, about 2.25 percent to about 6.75 percent by weight, about 1.5 percent to about 4.5 percent by weight, or from about 0.75 percent to about 2.25 percent by weight.

As used herein, the term "silicate nanoparticles", used alone or in combination with other terms, refers to silicate layered clays. Example silicate layered clays include, but are not limited to, laponite, montmorillonite, saponite, hectorite, kaolinite, palygorskite, and sepiolite. Silicate nanoparticles can be prepared, for example, by dialysis and similar purification techniques known in the art to remove any impurities. In some embodiments, overall charge of the silicate nanoparticles is negative. In some embodiments, the silicate nanoparticles are from about 5 nm to about 60 nm in diameter, for example, from about 10 nm to about 40 nm in diameter, from about 10 nm to about 30 nm in diameter, or from about 20 to about 30 nm in diameter. In some embodiments, the silicate nanoparticles are from about 0.5 nm to about 2 nm in thickness. In some embodiments, the silicate nanoparticles are about 1 nm in thickness.

In some embodiments, the silicate nanoparticles comprise silicate nanoplatelets. As used herein, the term "silicate nanoplatelets", used alone or in combination with other terms, refers to silicate layered clays characterized by a discotic charge distribution on the surface. Silicate nanoplatelets can be prepared, for example, by dispersion and sonication in an aqueous solution. In some embodiments, the silicate nanoplatelets comprise a positively charged edge and a negatively charged surface. In some embodiments, the overall charge of the silicate nanoplatelets is negative. In some embodiments, the silicate nanoplatelets are from about 5 nm to about 60 nm in diameter, for example, from about 10 nm to about 40 nm in diameter, from about 10 nm to about 30 nm in diameter, or from about 20 to about 30 nm in diameter. In some embodiments, the silicate nanoplatelets are from about 0.5 nm to about 2 nm in thickness. In some embodiments, the silicate nanoplatelets are about 1 nm in thickness.

In some embodiments, the shear-thinning compositions provided herein comprise about 0.5 percent to about 30 percent by weight of the silicate nanoparticles, for example, about 0.5 percent to about 20 percent by weight, about 0.5 percent to about 10 percent by weight, about 2.25 percent to about 6.75 percent by weight, about 1.5 percent to about 4.5 percent by weight, or about 0.75 percent to about 2.25 percent by weight.

In some embodiments, the ratio of silicate nanoparticles to gelatin or a derivative thereof, is from about 0.1 to about 1.0, for example, about 0.1, about 0.2, about 0.3, about 0.4, about 0.5, about 0.6, about 0.7, about 0.8, about 0.9 or about 1.0. In some embodiments, the ratio of gelatin or a derivative thereof to silicate nanoparticles is from about 0.1 to about 1.0, for example, about 0.1, about 0.2, about 0.3, about 0.4, about 0.5, about 0.6, about 0.7, about 0.8, about 0.9 or about 1.0.

In some embodiments, the shear-thinning compositions provided herein comprise about 0.5 percent to about 85 percent by weight of gelatin or a derivative thereof and silicate nanoparticles together, for example, from about 0.5 percent to about 70 percent by weight, from about 0.5 percent to about 60 percent by weight, from about 0.5 percent to about 50 percent by weight, from about 0.5 percent to about 40 percent by weight, from about 0.5 percent to about 30 percent by weight, about 0.5 percent to about 25 percent by weight, from about 0.5 percent to about 15 percent by weight, about 0.5 percent to about 11 percent by weight, or about 3 percent to about 11 percent by weight. In some embodiments, the shear-thinning compositions provided herein comprise about 6.75 percent by weight gelatin and about 2.25 percent by weight silicate nanoparticles, about 4.5 percent by weight gelatin and about 4.5 percent by weight silicate nanoparticles, about 2.25 percent by weight gelatin and about 6.75 percent by weight silicate nanoparticles, about 4.5 percent by weight gelatin and about 1.5 percent by weight silicate nanoparticles, about 3 percent by weight gelatin and about 3 percent by weight silicate nanoparticles, about 1.5 percent by weight gelatin and about 4.5 percent by weight silicate nanoparticles, about 2.25 percent by weight gelatin and about 0.75 percent by weight silicate nanoparticles, about 1.5 percent by weight gelatin and about 1.5 percent by weight silicate nanoparticles, or about 0.75 percent by weight gelatin and about 2.25 percent by weight silicate nanoparticles.

In some embodiments, a shear-thinning composition provided herein is a physically crosslinked gel comprising gelatin or a derivative thereof, and silicate nanoparticles. In some embodiments, the shear-thinning composition is a physically crosslinked hydrogel comprising gelatin or a derivative thereof, and silicate nanoparticles.

In some embodiments, a shear-thinning composition provided herein further comprises water, for example, ultrapure water (e.g., Milli-Q) or buffered water (e.g., phosphate buffered saline). In some embodiments, the shear-thinning composition comprises from about 0.5 percent to about 99 percent by weight of water, for example, from about 30 percent to about 99 percent by weight, about 50 percent to about 99 percent by weight, about 70 percent to about 99 percent by weight, about 80 percent to about 99 percent by weight, about 90 percent to about 99 percent by weight, or about 91 percent to about 97 percent by weight.

In some embodiments, the shear-thinning composition comprises, for example, about 6.75 percent by weight gelatin, about 2.25 percent by weight silicate nanoparticles, and about 91 percent by weight water, about 4.5 percent by weight gelatin, about 4.5 percent by weight silicate nanoparticles, and about 91 percent by weight water, about 2.25 percent by weight gelatin, about 6.75 percent by weight silicate nanoparticles, and about 91 percent by weight water, about 4.5 percent by weight gelatin, about 1.5 percent by weight silicate nanoparticles, and about 94 percent by weight water, about 3 percent by weight gelatin, about 3 percent by weight silicate nanoparticles, and about 94 percent by weight water, about 1.5 percent by weight gelatin, about 4.5 percent by weight silicate nanoparticles, and about 94 percent by weight water, about 2.25 percent by weight gelatin, about 0.75 percent by weight silicate nanoparticles, and about 97 percent by weight water, about 1.5 percent by weight gelatin, about 1.5 percent by weight silicate nanoparticles, and about 97 percent by weight water, or about 0.75 percent by weight gelatin, about 2.25 percent by weight silicate nanoparticles, and about 97 percent by weight water.

In some embodiments, a shear-thinning composition provided herein is self-healing. As used herein, the expression "self-healing", used alone or in combination with other terms, refers to recovery of the elastic gel strength of a composition upon removal of a stress. In some aspects, a self-healing composition may recover elastic gel strength from about 2 seconds to about 1 minute after removal of a stress, for example, from 30 seconds to 1 min., from 30 seconds to 45 seconds, from 15 seconds to 1 minute, from 15 seconds to 45 seconds, from 15 seconds to 30 seconds, from 10 seconds to 15 seconds, from 10 seconds to 30 seconds, from 10 seconds to 45 seconds, from 10 seconds to 1 minute, from 5 seconds to 10 seconds, from 5 seconds to 25 seconds, from 5 seconds to 45 seconds, from 5 seconds to 1 minute, from 2 seconds to 10 seconds, from 2 seconds to 25 seconds, from 2 seconds to 45 seconds, or from about 2 seconds to 1 minute.

In some embodiments, a shear-thinning composition provided herein flows upon application of a pressure greater than the yield stress, for example, application of a pressure about 10% greater, about 20% greater, about 30% greater, about 40% greater, about 50% greater about 60% greater, about 70% greater, about 80% greater, about 90% greater, or about 100% greater than the yield stress. In some embodiments, the yield stress of the shear-thinning composition is from about 1 Pa to about 200 Pa, for example, from about 1 Pa to about 100 Pa, from about 2 Pa to about 89 Pa, from about 2 Pa to about 50 Pa, from about 1 Pa to about 25 Pa, from about 1 Pa to about 10 Pa, or from about 1 Pa to about 5 Pa.

In some embodiments, shear-thinning compositions provided herein are useful for accelerating blood clotting (e.g., reducing blood clotting time). Prior to the application of a shear-thinning composition, an active bleeding site may be characterized as bleeding at a rate from about 0.5 mL/min to about 1000 mL/min, for example, 0.5 mL/min to 500 mL/min, 0.5 mL/min to 200 mL/min, 0.5 mL/min to 100 mL/min, 0.5 mL/min to 25 mL/min, 1 mL/min to 10 mL/min, 1 mL/min to 100 mL/min, 1 mL/min to 500 mL/min, 10 mL/min to 100 mL/min, 10 mL/min to 250 mL/min, 10 mL/min to 500 mL/min, 10 mL/min to 1000 mL/min, 50 mL/min to 250 mL/min, or 50 mL/min to 500 mL/min.

In some embodiments, the active bleeding is an internal active bleeding. An internal active bleeding site may be characterized by a rate of blood flow from 0.1 mL/min to 20 mL/min, for example, 0.1 mL/min to 10 mL/min, 0.1 mL/min to 5 mL/min, 0.1 mL/min to 1 mL/min, 0.1 mL/min to 0.5 mL/min, 0.25 mL/min to 20 mL/min, 0.25 mL/min to 10 mL/min, 0.25 mL/min to 5 mL/min, 0.25 mL/min to 1 mL/min, or 0.25 mL/min to 0.5 mL/min.

In some embodiments, a shear-thinning composition provided herein can be prepared according to procedures provided in International Publication WO 2014/205261, which is incorporated herein by reference in its entirety.

In some embodiments, a shear-thinning composition provided herein comprises chitosan. In some embodiments, the shear-thinning composition comprises about 1 to about 15% chitosan, for example, about 1 to about 15%, about 2 to about 15%, about 5 to about 15%, about 8 to about 15%, about 10 to about 15%, about 12 to about 15%, about 1 to about 12%, about 2 to about 12%, about 5 to about 12%, about 8 to about 12%, about 10 to about 12%, about 1 to about 10%, about 2 to about 10%, about 5 to about 10%, about 8 to about 10%, about 1 to about 8%, about 2 to about 8%, about 5 to about 8%, about 1 to about 5%, about 2 to about 5%, or about 1 to about 2% chitosan. In some embodiments, the composition comprises about 5 to about 10% chitosan. In some embodiments, the composition comprises about 8% chitosan.

Methods of Treatment

The present application further provides methods of treating a vascular disorder or condition in a subject in need thereof, comprising administering to the subject a therapeutically effective amount of a shear-thinning composition provided herein. In some embodiments, the vascular disorder or condition is selected from the group consisting of an aneurysm, a hemorrhage, a venous congestion disorder, a varix, an abscess, a fistula, a cancer, and an infection.

In some embodiments, the present application provides a method of treating of treating an aneurysm in a subject in need thereof, comprising administering to the subject a therapeutically effective amount of a shear-thinning composition. In some embodiments, the aneurysm is a saccular, fusiform or mycotic aneurysm or a pseudoaneurysm. In some embodiments, the aneurysm is selected from the group consisting of an idiopathic aneurysm, an iatrogenic aneurysm, a traumatic aneurysm, infectious aneurysm, and an atherosclerotic aneurysm. In some embodiments, the aneurysm is selected from the group consisting of cerebral aneurysm, aortic aneurysm, ventricular aneurysm, renal aneurysm, abdominal aneurysm, splenic, hepatic, mesenteric artery, gastric, femoral, popliteal, brachial, and pancreaticoduodenal arcade aneurysm.

In some embodiments, the treating comprises administering the shear-thinning composition into the arterial or venous aneurysm. In some embodiments, the administration comprises stent-assisted administration. In some embodiments, the administration is endovascular or percutaneous administration. In some embodiments, the treating comprises administering the shear-thinning composition into the aneurysm in an amount effective to prevent rupture of the aneurysm, aneurysm growth, recanalization, or any combination thereof.

In some embodiments, the present application provides a method of treating a hemorrhage in a subject in need thereof, comprising administering to the subject a therapeutically effective amount of a shear-thinning composition. In some embodiments, the hemorrhage is an internal hemorrhage. In some embodiments, the hemorrhage is selected from the group consisting of an internal Class I hemorrhage, an internal Class II hemorrhage, an internal Class III hemorrhage, and an internal Class IV hemorrhage. In some embodiments, the hemorrhage is selected from the group consisting of arterial gastrointestinal hemorrhage, venous gastrointestinal hemorrhage, liver hemorrhage, spleen hemorrhage, stomach hemorrhage, kidney hemorrhage, pulmonary hemorrhage, small bowel hemorrhage, large bowel hemorrhage, lower limb/upper limb hemorrhage, intracranial hemorrhage, intracerebral hemorrhage, and subarachnoid hemorrhage. In some embodiments, the hemorrhage is a hemorrhage of the femoral artery or an aortic hemorrhage.

In some embodiments, the hemorrhage is an internal hemorrhage associated with a medical disorder or a trauma. Example medical disorders include, but are not limited to a gastrointestinal disorder, a renal disorder, a pulmonary disorder, and a cancer. Example traumas include, but are not limited to blunt trauma, an abrasion, an avulsion, an incision, a laceration, a puncture, a penetration, and surgical trauma.

In some embodiments, hemorrhage is associated with a medical disorder, wherein the medical disorder is a gastrointestinal disorder. Example gastrointestinal disorders include, but are not limited to, an ulcer, a gastrointestinal varix, esophagitis, gastritis, atrophic gastritis, gastrointestinal or esophageal erosion, diverticular disease, vascular ectasia, ischemic colitis, infectious colitis, ulcerative colitis, inflammatory bowel disease, Crohn's disease, gastroesophageal reflux disease, and Barrett's oesophagus. In some embodiments, the gastrointestinal disorder selected from the group from the group consisting of an ulcer, a varix, esophagitis, gastritis, erosion, diverticular disease, vascular ectasia, ischemic colitis, infectious colitis, inflammatory bowel disease. In some embodiments, the gastrointestinal disorder is selected from the group from the group consisting of an ulcer, a gastrointestinal varix, esophagitis, gastritis, gastrointestinal or esophageal erosion, diverticular disease, vascular ectasia, ischemic colitis, infectious colitis, and inflammatory bowel disease.

In some embodiments, the hemorrhage is associated with a medical disorder, wherein the medical disorder is cancer. In some embodiments, the hemorrhage is associated with a cancer, wherein the cancer is selected from the group consisting of breast cancer, prostate cancer, benign prostatic hyperplasia, esophageal cancer, liver cancer, colon cancer, endometrial cancer, brain cancer, bladder cancer, cancer of the uterus, fibroid (leiomyoma) uterus, cancer of the ovary, lung cancer, sarcoma, bone cancer, pancreatic cancer, renal cancer, and stomach cancer. In some embodiments, the cancer is selected from the group consisting of gastric cancer, stomach cancer, liver cancer, and lung cancer. In some embodiment, the cancer is gastric cancer or stomach cancer.

In some embodiments, the hemorrhage is associated with a trauma, wherein the trauma is selected from the group consisting of blunt trauma, an abrasion, an avulsion, an incision, a laceration, a puncture, a penetration, surgical trauma, iatrogenic trauma, or any combination thereof. In some embodiments, the trauma is a blunt trauma. In some embodiments, the blunt trauma comprises an internal trauma, for example, blunt abdominal trauma, gastrointestinal trauma, trauma of the lung, trauma of the gall bladder, trauma of the stomach, trauma of the appendix, trauma of the liver, trauma of the spleen, trauma of the small intestine, and trauma of the large intestine. In some embodiments, the trauma comprises blunt abdominal trauma.

In some embodiments, the treating comprises locally administering the shear-thinning composition at the site of the hemorrhage. In some embodiments, the treating comprises locally administering the shear-thinning composition at the site of the hemorrhage in an amount effective to reduce or stop bleeding of the hemorrhage. In some embodiments, the administration is endovascular or percutaneous administration.

In some embodiments, the shear-thinning composition is administered to reduce or stop bleeding in a subject wherein the subject has been treated with one or more anti-coagulants, one or more anti-platelet agents, or a combination thereof (e.g., prior to administration of the shear-thinning composition). In some embodiments, the subject has been treated with one or more anti-coagulants, one or more anti-platelet agents, or a combination thereof, less than about 48 hours prior to administering the shear-thinning composition, for example, less than about 36 hours, less than about 24 hours, less than about 18 hours, less than about 12 hours, less than about 8 hours, less than about 6 hours, less than about 4 hours, less than about 2 hours, or less than about 1 hour prior to administering the shear-thinning composition. In a subject having been treated with one or more anti-coagulants, one or more anti-platelet agents, or a combination thereof, the standard of therapy, which can include using coil embolization, may be ineffective, as the standard of therapy requires that the subject have the ability to form a blood clot to occlude a vessel to prevent bleeding. The shear-thinning compositions provided herein can be used to occlude anticoagulated blood vessels, as the composition does not require the subject to form a blood clot to occlude the blood vessel.

In some embodiments, the shear-thinning composition is administered to reduce or stop bleeding in a subject, wherein the subject has been treated with:
  i) one or more anti-coagulants, one or more anti-platelet agents, or a combination thereof; and
  ii) a standard embolization therapy (e.g., coil embolization);
prior to administration of the shear-thinning composition.

In some embodiments, the bleeding comprises active bleeding. In some embodiments, the bleeding comprises active bleeding after the subject has been treated with the standard embolization therapy (e.g., coil embolization).

In some embodiments, the shear-thinning composition is administered to stop bleeding in a subject wherein the subject has been treated with one or more anti-coagulants. Example anti-coagulants include, but are not limited to, warfarin, apixaban, dabigatran, rivaroxaban, edoxaban, dalteparin, desirudin, enoxaparin, fondaparinux, and heparin. In some embodiments, the anti-coagulant is selected from the group consisting of warfarin, apixaban, dabigatran, rivaroxaban, and edoxaban.

In some embodiments, the shear-thinning composition is administered to reduce or stop bleeding in a subject wherein the subject has been treated with one or more anti-platelet agents. Example anti-platelet agents include, but are not limited to, anagrelide, aspirin, cilostazol, clopidogrel, dipyridamole, prasugrel, ticagrelor, ticlopidine, and vorapaxar. In some embodiments, the anti-platelet agent is selected from the group consisting of anagrelide, aspirin, cilostazol, clopidogrel, dipyridamole, prasugrel, ticagrelor, ticlopidine, and vorapaxar.

In some embodiments, the present application provides a method of treating a venous congestion disorder in a subject in need thereof, comprising administering to the subject a therapeutically effective amount of a shear-thinning composition. In some embodiments, the venous congestion disorder is selected from the group consisting of pelvic congestion syndrome, chronic venous insufficiency, lower extremity varicose veins, hemorrhoids, and congested or distended mesenteric veins. In some embodiments, the lower extremity varicose veins comprise branches of the saphenous vein, for example, the great saphenous vein and small saphenous vein. In some embodiments, the congested or distended mesenteric veins include, but are not limited to, gastric, splenic, umbilical, esophageal, and inferior branches of the mesenteric veins or superior branches of the mesenteric veins, for example, rectal and duodenal branches. In some embodiments, the venous congestion disorder is pelvic congestion syndrome or chronic venous insufficiency. In some embodiments, the treating comprises locally administering the shear-thinning composition at the site of the venous congestion disorder. In some embodiments, the treating comprises locally administering the shear-thinning composition at the site of the venous congestion disorder in an amount effective to occlude a blood vessel in the subject. In some embodiments, the administration is endovascular or percutaneous administration. In some embodiments, the venous congestion disorder is associated with varicose veins, venous stasis, an ulcer, stasis dermatitis, contact dermatitis, livedoid vasculopathy, lipodermatosclerosis, inflammation, discoloration of the skin, cellulitis, or any combination thereof.

In some embodiments, the present application provides a method of treating a varix in a subject in need thereof, comprising administering to the subject a therapeutically effective amount of a shear-thinning composition. In some embodiments, the varix is selected from the group consisting of a varicose vein, an arterial varix, a lymphatic varix, an esophageal varix, an intestinal varix, a scrotal varix, a vesical varix, a pelvic varix, and a rectal varix. In some embodiments, the varix is selected from the group consisting of a varicose vein, an arterial varix, or a lymphatic varix. In some embodiments, the varix is a varicose vein. In some embodiments, the varix is associated with portal hypertension. In some embodiments, the treating comprises locally administering the shear-thinning composition at the site of the varix in an amount effective to occlude the varix. In some embodiments, the treating comprises locally administering the shear-thinning composition at the site of a varicose vein in an amount effective to occlude the varicose vein. In some embodiments, the administration is endovascular or percutaneous administration.

In some embodiments, the present application provides a method of treating an abscess or fistula in a subject in need thereof, comprising administering to the subject a therapeutically effective amount of a shear-thinning composition. In some embodiments, the treating comprises administering the shear-thinning composition into the abscess or fistula. In some embodiments, the treating comprises administering the shear-thinning composition into the abscess or fistula in an amount effective to substantially fill the abscess or fistula. In some embodiments, the treating comprises locally administering the shear-thinning composition at the site of the abscess or fistula. In some embodiments, the administration is endovascular or percutaneous administration.

Combination Therapies

One or more additional agents can be used in combination with the compositions provided herein for the treatment of a vascular disorder or condition in a subject in need thereof. In some embodiments, the additional agent is a therapeutic agent or a diagnostic agent. In some embodiments, the additional agent is a therapeutic agent. In some embodiments, the additional agent is a diagnostic agent. In some embodiments, the present application provides a method of treating a vascular disorder or condition in a subject in need thereof, comprising administering to the subject a shear-thinning composition provided herein and one or more additional therapeutic agents. In some embodiments, the present application provides a method of treating a vascular disorder or condition in a subject in need thereof, comprising administering to the subject a shear-thinning composition provided herein and an additional therapeutic agent. In some embodiments, the present application provides a method of treating a vascular disorder or condition in a subject in need thereof, comprising administering to the subject a shear-thinning composition provided herein and one or more additional diagnostic agents. In some embodiments, the present application provides a method of treating a vascular disorder or condition in a subject in need thereof, comprising administering to the subject a shear-thinning composition provided herein and an additional diagnostic agent. In some embodiments, the vascular disorder or condition is selected from the group consisting of an aneurysm, a hemorrhage, a venous congestion disorder, a varix, an abscess, a fistula, a cancer, and an infection. In some embodiments, the vascular disorder or condition is selected from the group consisting of an abscess, a fistula, a cancer, and an infection.

In some embodiments, at least one of the additional agents is preloaded onto at least one surface of the shear-thinning composition prior to the treating. In some embodiments, at least one of the additional agents is preloaded into the shear-thinning composition prior to the treating. In some embodiments, at least one of the additional agents is preloaded onto at least one surface of the shear-thinning composition and at least one of the additional agents is preloaded into the shear-thinning composition prior to the treating. In some embodiments, at least one of the additional agents is a therapeutic agent.

In some embodiments, each of the one or more additional therapeutic agents is independently selected from the group consisting of a steroid, an anti-allergic agent, an anesthetic, an immunosuppressant, an anti-microbial agent, an anti-fungal agent, an anti-inflammatory agent, an adhesive agent, a regenerative agent, a hemostatic agent, a chemotherapeutic agent.

Example steroids include, but are not limited to, corticosteroids such as cortisone, dexamethasone, hydrocortisone, methylprednisolone, prednisolone, and prednisone.

Example anti-allergic agents include, but are not limited to anti-histamines (e.g., cetirizine, fexofenadine, hydroxyzine, and loratadine), ephedrine, and theophylline.

Example anesthetics include, but are not limited to local anesthetics such as lidocaine, procain, and ropivacaine.

Example immunosuppressants include, but are not limited to, azathioprine, chlorambucil, cyclophosphamide, cyclosporine, daclizumab, infliximab, methotrexate, and tacrolimus.

Example anti-microbial agents include, but are not limited to, aminoglycosides (e.g., gentamicin, neomycin, and streptomycin), penicillins (e.g., amoxicillin and ampicillin), and macrolides (e.g., erythromycin).

Example anti-fungal agents include, but are not limited to, polyene anti-fungal agents (e.g., amphotericin B and candicidin), imidazole anti-fungal agents (e.g., bifonazole, clotrimazole, and econazole), triazole anti-fungal agents (e.g., albaconazole, efinaconazole, and fluconazole), thiazole anti-fungal agents (e.g., abafungin), allylamine anti-fungal agents (e.g., amorolfin, butenafine, and naftifine), echinocandins (e.g., anidulafungin and caspofungin).

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example adhesive agents include, but are not limited to surgical glues such as fibrin-based glues; crosslinked proteins such as collagen, gelatin, and albumin; cyanoacrylates; and polymers such as poly(ethylene-glycol), poly(urethanes), poly(caprolactone), poly(hydroxy ethyl methacrylate), and poly(methyl methacrylate).

Example regenerative agents include, but are not limited to proteins such as vascular endothelial growth factor, fibroblast growth factor, interleukins, keratinocyte growth factor; small molecule drugs and peptides and natural polysaccharides.

Example hemostatic agents include, but are not limited to chitosan, or a salt thereof, and styptics.

Example chemotherapeutics include, but are not limited to, proteosome inhibitors (e.g., bortezomib), thalidomide, revlimid, and DNA-damaging agents such as melphalan, doxorubicin, cyclophosphamide, vincristine, etoposide, carmustine, and the like.

One or more of the following agents may be used in combination with the compositions provided herein and are presented as a non-limiting list: a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, SCH 66336, R115777, L778,123, BMS 214662, gefitinib, erlotinib hydrochloride, antibodies to EGFR, imatinib mesylate, intron, ara-C, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, doxorubicin, epirubicin, idarubicin, mithramycin, deoxycoformycin, mitomycin-C,L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, vinorelbine, porfimer, erbitux, liposomal, thiotepa, altretamine, melphalan, trastuzumab, fulvestrant, exemestane, ifosfamide, rituximab, C225, alemtuzumab, clofarabine, cladribine, aphidicolin, sunitinib, dasatinib, tezacitabine, Sml1, triapine, didox, trimidox, amidox, 3-AP, MDL-101,731, bendamustine, ofatumumab, and GS-1101 (also known as CAL-101).

In some embodiments, each of the one or more diagnostic agents is independently selected from the group consisting of a magnetic agent, an electrical agent, a biosensor for bacteria, or any combination thereof. In some embodiments, the biosensor for bacteria is useful to enable treatment monitoring of the subject.

Example magnetic agents include, but are not limited to, magnetic resonance imaging agents, iron oxide nanoparticles, zinc oxide nanoparticles, magnesium oxide particles, metallic particles for contrast agents, and polymeric nanoparticles containing metallic nanoparticles.

Example electrical agents include, but are not limited to, metallic nanoparticles, graphene/graphene oxide, and carbon nanotubes.

Example biosensors for bacteria include, but are not limited to pH and oxygen responsive nanoparticles.

In some embodiments, the present application provides a method of treating an abscess or a fistula in a subject in need thereof, comprising administering to the subject a therapeutically effective amount of a shear-thinning composition and an additional agent. In some embodiments, the treating comprises locally administering the shear-thinning composition at the site of the abscess or fistula in an amount effective to substantially fill the abscess or fistula. In some embodiments, the additional agent is selected from the group consisting of an antimicrobial agent, an antifungal agent, an anti-inflammatory agent, an adhesive agent, a regenerative agent, a hemostatic agent, a magnetic agent, an electrical agent, a biosensor for bacteria to enable treatment monitoring, or any combination thereof. In some embodiments, the additional agent is an additional therapeutic agent. In some embodiments, the additional agent is selected from the group consisting of an antimicrobial agent, an antifungal agent, an anti-inflammatory agent, an adhesive agent, a regenerative agent, a hemostatic agent, or any combination thereof.

In some embodiments, the present application provides a method of treating cancer in a subject in need thereof, comprising administering to the subject a therapeutically effective amount of a shear-thinning composition and an additional agent. In some embodiments, the cancer is selected from the group consisting of breast cancer, prostate cancer, benign prostatic hyperplasia, esophageal cancer, liver cancer, colon cancer, endometrial cancer, brain cancer, bladder cancer, cancer of the uterus, fibroid (leiomyoma) uterus, cancer of the ovary, lung cancer, sarcoma, bone cancer, pancreatic cancer, renal cancer, and stomach cancer. In some embodiments, the cancer comprises a solid tumor. In some embodiments, the additional agent is a diagnostic agent. In some embodiments, the diagnostic agent is a biosensor. In some embodiments, the additional agent is a therapeutic agent. In some embodiments, the additional therapeutic agent is a sensitizing drug to adjuvant therapy (e.g., a sensitizing drug to a chemotherapy or radiation therapy). Example sensitizing drugs include, but are not limited to, misonidazole, bromodeoxyuridine, cisplatin, 5-fluorouracil [5-FU], taxanes, tirapazamine, mitomycin C, and paclitaxel.

In some embodiments, the additional therapeutic agent is a chemotherapeutic agent. In some embodiments, the additional therapeutic agent is released from the shear-thinning composition upon contacting the cancer with the shear-thinning composition.

In some embodiments, the present application provides a method of treating an infection in a subject in need thereof, comprising administering to the subject a therapeutically effective amount of a shear-thinning composition and an additional agent. In some embodiments, the infection is selected from the group consisting of a bacterial infection, a fungal infection, a viral infection, a nematode infection, and a parasitic infection. In some embodiments, the infection is selected from the group consisting of a bacterial infection, a fungal infection, parasitic infection and a viral infection. In some embodiments, the additional agent is a therapeutic agent or a diagnostic agent. In some embodiments, the additional agent is a therapeutic agent. In some embodiments, the additional therapeutic agent is selected from the group consisting of an antibacterial agent, an antifungal agent, an anti-viral agent, an anti-inflammatory agent, a steroid, or any combination thereof. In some embodiments, the additional therapeutic agent is an antibacterial agent.

Administration and Dosage Forms

The compositions provided herein can be administered by a variety of routes, depending upon the area to be treated. In some embodiments, the shear-thinning compositions are administered by parenteral administration. Parenteral administration includes intravenous, intraarterial, subcutaneous, intraperitoneal intramuscular, injection, or infusion; or intracranial, (e.g., intrathecal or intraventricular administration). Parenteral administration can be in the form of a single bolus dose, or may be, for example, by a continuous perfusion pump. In some embodiments, the administering comprises injecting the shear-thinning composition. In some embodiments, the administering comprises an image guided endovascular procedure or an image guided percutaneous procedure where computed tomography, fluoroscopy or ultrasound imaging is used to deliver the composition. In some embodiments, the administering comprises injecting the shear-thinning composition into the vascular system of a subject. In some embodiments, the administering comprises injecting the shear-thinning composition into a cancer of the subject. In some embodiments, the cancer is a solid tumor. In some embodiments, the administering comprises injecting the shear-thinning composition into an abscess or fistula of the subject.

In some embodiments, the shear-thinning composition is administered to displace a solid organ. In some embodiments, the shear-thinning composition is administered to displace a solid organ during a surgical procedure (e.g., a biopsy procedure, an ablation procedure, and the like). In some embodiments, the surgical procedure further comprises imaging the subject (e.g., a tissue, cell, or bone of the subject) with an appropriate imaging technique. Example imaging techniques include, but are not limited to, computed tomography, ultrasound, and flurosocopy imaging techniques. In some embodiments, the surgical procedure is a biopsy procedure. For example, the shear-thinning composition can be used to displace a solid organ (e.g., an adrenal gland) to provide safe needle access for a tissue biopsy (e.g., a lymph node biopsy). In some embodiments, the surgical procedure is an ablation procedure. In some embodiments, the ablation procedure is an organ ablation procedure or a tumor ablation procedure. Without being bound by any theory, a shear-thinning composition as provided herein can function as a "heat-sink" to protect adjacent tissues when solid tissue is thermally ablated. For example, the biomaterial can be injected in between a kidney and the large bowel to allow safe ablation of kidney tumor-protecting the bowel from potential thermal injury.

In some embodiments, the administering is performed using a catheter or a syringe. In some embodiments, the administering is performed using a catheter. In some embodiments, the shear-thinning composition is preloaded onto at least one surface of a medical device prior to the treating. In some embodiments, the shear-thinning composition is preloaded into a medical device prior to the treating. In some embodiments, the shear-thinning composition is preloaded into a catheter prior to the treating. In some embodiments, the shear-thinning composition is preloaded into a syringe prior to the treating.

The amount of the composition administered to a subject will vary depending upon the composition being administered, the purpose of the administration, the state of the subject, the manner of administration, and the like. In therapeutic applications, compositions can be administered to a subject to cure or at least partially arrest the symptoms and its complications. Effective doses will depend on the necessary treatment as well as by the judgment of the attending clinician depending upon factors such as the type and severity of the complication (e.g., aneurysm, abscess, GI bleed, and the like), the age, weight and general condition of the subject, and the like.

Cosmetic Applications

The compositions provided herein may also be useful as components in cosmetic compositions. Benefits of shear-thinning compositions in cosmetic applications include, but are not limited to, the biocompatibility and non-toxic character of shear-thinning compositions provided herein (e.g., a shear-thinning composition may degrade over time in subcutaneous tissue). Example cosmetic compositions include, but are not limited to, dermal fillers, Botulinum toxin compositions (e.g., Botox®), and cosmetic implants (e.g., breast implants, lip implants, buttock implants, and the like). In some embodiments, the compositions provided herein may be combined with a therapeutic agent provided herein (e.g., antibacterial agent, anti-inflammatory agent, and the like), for use in cosmetic applications. Example cosmetic applications include, but are not limited to, dental augmentation, breast augmentation, buttock augmentation, lip augmentation, jaw augmentation, hip augmentation, chin augmentation, brow augmentation, arm augmentation, leg augmentation, and the like.

Kits

The present application further provides a kit comprising a shear-thinning composition provided herein and one or more catheters. The kit is useful, for example, in the treatment of a vascular disorder or condition such as an aneurysm, a hemorrhage, a venous congestion disorder, a varix, an abscess, a fistula, a cancer, or an infection.

In some embodiments, the kit comprises one or more components of a shear-thinning composition provided herein (e.g., gelatin or a derivative thereof, silicate nanoparticles, silicate nanoplatelets, chitosan, or any combination thereof) and one or more catheters. For example, the components can be separately packaged or contained.

In some embodiments, the kit comprises a pharmaceutically acceptable amount of a shear-thinning composition preloaded onto one or more of the catheters. In some embodiments, the kit comprises a pharmaceutically acceptable amount of a shear-thinning composition preloaded into one or more of the catheters.

In some embodiments, the kit comprises a shear-thinning composition provided herein and one or more sterile syringes. In some embodiments, the shear-thinning composition is preloaded into one or more of the sterile syringes.

Instructions, either as inserts or as labels, indicating quantities of the composition to be administered, guidelines for administration, and/or guidelines for mixing components of the composition, can also be included in a kit provided herein. In some embodiments, the instructions further comprise instructions for performing one or more of the methods provided herein. In some embodiments, the instructions further comprise instructions for quantities of the composition to be administered, guidelines for administration, and/or guidelines for mixing components of the composition.

In some embodiments, the kit further comprises an additional therapeutic agent. In some embodiments, the additional therapeutic agent is selected from the group consisting of a steroid, an anti-allergic agent, an anesthetic, an immunosuppressant, an anti-microbial agent, an anti-fungal agent, an anti-inflammatory agent, an adhesive agent, a regenerative agent, a hemostatic agent, a chemotherapeutic agent.

The kits provided herein can further include, if desired, one or more conventional pharmaceutical kit components, such as, for example, containers with one or more pharmaceutically acceptable carriers, additional containers, etc., as will be readily apparent to those skilled in the art.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.
General Methods.

Physical mixtures of gelatin and silicate nanoplatelets were used to formulate the compositions disclosed herein. Synthetic silicate nanoplatelets (Laponite XLG) were purchased from Southern Clay Products, Inc. (Louisville, Ky.). Type-A porcine skin gelatin was obtained from Sigma Aldrich (Milwaukee, Wis.).

As a general procedure, silicate nanoplatelets were exfoliated in ultrapure (Milli-Q) water using a vortexer to enhance the surface area available for interaction with gelatin. Next, a gelatin stock, heated to liquefy the solution, was vigorously mixed with the exfoliated silicate at room temperature. Vigorous agitation was necessary to prevent clumping of the nanoplatelets during gelation; however, the nanoplatelets were stably dispersed after the gel had set.

The compositions of the examples were prepared with total solid concentrations (e.g., gelatin+silicate nanoplatelets) of 3, 6, and 9 weight percent. The ratio of solid components used in the compositions provided herein (e.g. gelatin:nanoplatelet and chitosan:nanoplatelet) is from about 0:1 to about 1:0. Shear-thinning compositions provided herein are abbreviated by XNCY where X represents the percent of the shear-thinning composition by weight made up of solid materials (e.g., gelatin, silicate nanoplatelets, and chitosan) and Y represents the percent of the solid material that is silicate nanoplatelets. In the absence of silicate nanoplatelets, the gelatin solution was a viscous liquid at 37° C. Upon mixing silicate nanoplatelets with gelatin, the composition gelled in about 1 minute.

Oscillatory shear rheology was performed over a temperature range from 15° C. to 45° C., mimicking common environmental and physiological temperatures that the compositions may be exposed during sample preparation and in vivo applications.

Small Angle X-Ray Scattering (SAXS) was performed at the National Synchrotron Light Source (NSLS) at Brookhaven National Laboratory at beamline X27C. Samples were placed in a 1 mm thick washer and sealed between Kapton tape. Samples were equilibrated at 37° C. and 20° C. for 20 minutes prior to data collection. Scattering patterns were collected for 30 seconds per sample. Radial integration of the two dimensional scattering pattern was performed to yield a one dimensional scattering curve, which was corrected for empty cell and dark field scattering. Thin disk form factor model fitting was performed in MatLab using a nonlinear fit algorithm to fit the radius and a Gaussian distribution for polydispersity of the composition.

An Anton Paar MCR 301 rheometer was used for mechanical testing. A 25 mm diameter parallel plate geometry with a gap height of 500 μm was used for temperature sweeps and mineral oil was placed around the circumference of the plate to prevent evaporation of water from the composition for all tests. Compositions were equilibrated for 10 minutes prior to testing, followed by a 2 minute steady shear at 10 s$^{-1}$. 10 s of equilibrium time was sufficient for the viscosity to return to a higher plateau value, after which point testing was initiated. Frequency and shear rate sweeps were performed at 20 and 37° C., with frequencies from 0.001-100 Hz at 1% strain and shear rates from 0.001 to 100 s$^{-1}$ with 10 points/decade. Frequency sweeps were performed with a cone geometry (25 mm diameter, 1° angle, 50 μm truncation gap). Stress-controlled temperature sweeps were performed from 15-45° C. at 10 Pa stress and 1 Hz. All other tests were performed at 37° C. Oscillatory stress sweeps were performed from 0.01-100 Pa at 1 Hz. Strain Sweeps were performed from 0.01-1000% at 1 Hz. Recovery testing was conducted at 1 Hz by applying 100% strain, a value outside of the linear viscoelastic range, followed by 1% strain for 5 minutes to monitor gel recovery. Interfacial strength was also measured by applying a linearly increasing strain to a system of a composition and coagulated blood. Shear stress was measured until 1,800% strain. The maximum stress attained was used as a measure of the strength of the clot system.

Zeta potentials of gelatin and silicate nanoplatelets were determined in ultrapure water (Milli-Q) and phosphate buffered saline (PBS), pH 7.4 (Invitrogen) using a 633 nm laser in a Malvern ZEN3600 (Malvern Instruments, UK). Silicate nanoplatelets were dissolved with vigorous agitation (vortexing) while gelatin was dissolved with stirring at 40° C.

Viscosity vs shear rate curves were plotted on a log-log plot and fitted using the nonlinear least-squares regression algorithm in MATLAB. The linear region of the curves was fit with the fluid power law, Equation 1:

$$\eta = \eta_c \dot{\gamma}^{n-1} \qquad \text{Equation 1.}$$

where η is the viscosity, $\eta_c$ is the viscosity at 1 s$^{-1}$, $\dot{\gamma}$ is the shear rate and n is the power. Values of n<1 suggest a shear-thinning material.

Clotting Time

Blood was mixed with 10% 0.1-M $CaCl_2$ in MilliQ deionized (DI) water and pipetted to mix. 50 μL of whole blood was added to successive wells of a 96 well plate that were either uncoated, coated with a shear-thinning composition, or containing a 1 cm section of an embolic coil. After selected times, a well was washed with 0.9% saline solution and the liquid aspirated to leave only coagulated blood. Well plate images were taken using a Zeiss Axio Zoom V16 stereomicroscope.

Degradation

Human plasma was separated from citrated whole blood by gravity settling of the red blood cells. Plasma was used to incubate weighed shear-thinning composition (500 μL) in 1.5 mL Eppendorf tubes (VWR) at 37° C. Over 24 h, the plasma was removed, the remaining shear-thinning composition weighed, and replaced with fresh plasma.

Injection Force

The injectability of the material was analyzed using a mechanical tester (Instron Model 5542). The shear-thinning composition was added to a 3-mL plastic syringes (ID=8.66 mm, BD) and injected through medical catheters (4-French Beacon®, pediatric pigtail flush, and 5-French Beacon®, multipurpose A, Cook Incorporated) or needles (18 G and 23 G, Becton-Dickinson), using standard luer-lock fittings. The syringe plunger was depressed using an upper compressive platen and the housing of the syringe or catheter was fitted into a lower tensile grip to prevent movement during the experiment. The injection rate was controlled by changing the cross speed of the compression platen to achieve the desired flow rates. The force on the plunger was measured with a 100 N load cell and recorded using Bluehill 3 software.

Hemocompatibility

Citrated human whole blood (Research Blood Components, Brighton, Mass.) was used for all blood related testing.

Hemolysis

Hemolysis testing was performed according to protocols described in Kumar et al. *Biomacromolecules*, 2014, 15:1484-1490. Briefly, citrated whole blood was diluted 50× into 0.9% saline solutions. The shear-thinning composition was flattened in 1.5-mL Eppendorf tubes in a swinging bucket centrifuge. Equal volumes of diluted blood and either the shear-thinning composition, saline (negative control) or DI water (positive control) were incubated at 37° C. for 2 h under agitation in a shaker incubator (100 rpm, Labline Instruments). Samples were centrifuged (2000 rpm, Labnet) and the supernatant was transferred into wells of a 96-well plate. Percent hemolysis was calculated according to the Equation 2:

$$\% \text{ Hemolysis} = \frac{A_{sample} - A_{neg}}{A_{pos}} \times 100 \quad \text{Equation 2}$$

where $A_{sample}$ is the absorbance at 545 nm of the shear-thinning composition containing supernatant, $A_{neg}$ is the absorbance of the saline diluted blood and $A_{pos}$ is the absorbance of the DI water diluted blood.

Mouse Model

Shear-thinning compositions were mixed with contrast dye (Visipaque™) at a ratio of 1:30 Visipaque™:water and sterilization was performed as described herein. Following induction of anesthesia, mice were placed in a supine position over a warming platform to maintain a core temperature of 37° C. Laser Doppler perfusion imaging of the hind limbs was performed to obtain per-injection baseline scans. A 0.5-1 cm incision was made longitudinally on the anterior thigh of one hind limb. The vessels in the thigh were exposed under a surgical microscope using a combination of sharp and blunt dissection to expose the femoral artery and vein. The femoral artery segment distal to the inguinal ligament was mobilized and freed of its surrounding tissue. Two 6-0 silk sutures were passed distally and proximally underneath the artery to allow for gentle manipulation of the artery by lifting and aligning the vessel for injection. The artery was injected distally with a shear-thinning composition (6NC75) using 30 gauge sterile syringe needles. After injection, the incision was closed with a 5.0 polypropylene sutures and the mouse remained on the warming table for 1 h under general anesthesia followed by post shear-thinning composition injection laser Doppler perfusion imaging. The perfusion scanning of the injected hind limb was compare to the non-injected contralateral hind limb to confirm ischemia. After laser Doppler imaging was completed, animals were euthanized and the carcasses were placed inside a non-opaque container for contrast-enhanced micro computed tomography scanning (μCT) imaging.

μCT imaging was completed to produce high-resolution three-dimensional images constructed of two-dimensional trans-axial projections of the euthanized mouse hind limb to detect the radiodense contrast-containing shear-thinning composition casting of the vasculature 1 h after injection using Nikon XT H 225 (μCT) and Bruker SkyScan 1275 imaging scanners. The parameters used in the a Nikon platform were 70 kV, 20 W, 2400 projections, 4 frames per projection, and 225 ms exposure and for the SkyScan system were 70 kV, 166 μA, 2400 projections, and 4 frames per projection. The Nikon specimens were reconstructed with Nikon's CT Agent and CT Pro 3D software, and viewed in VGStudio MAX Version 2.2.The SkyScan specimens were reconstructed with SkyScan's NRecon software, and viewed in their CTAn Version 1.15 software.

Porcine Model

Female Yorkshire swine (Sus scrofa domestica; n=4; weight, 50 to 55 kg; Tufts Veterinary School, North Grafton, Mass.) were allowed to acclimate for at least 2 d in a cage; the night before procedure, food was withheld but water was provided ad libitum. For the procedure, all swine received tiletamine-zolazepam (5 mg/kg intramuscularly; Telazol, Zoetis, Florham Park, N.J.) and atropine (0.04 mg/kg IM) as pre-induction medication and then were placed supine on the operating table. After anesthesia induction (20 mg/kg intravenously; propofol), all swine were intubated (internal diameter of endotracheal tube, 7.5 to 8.0 mm) and ventilated mechanically (Evita 4, Drager, Lubeck, Germany).

During the procedure, electrocardiogram, transcutaneous oxyhemoglobin saturation (SpO2), end-tidal $CO_2$ concentration, inspired oxygen fraction and core temperature were monitored. A bolus of propofol (1 mg/kg IV) was used to maintain general anesthesia. Following anesthesia, access to the carotid artery or to the common femoral vein was obtained using ultrasound and C-Arm fluoroscopy (Siemens). The access needle and wire were exchanged for a 5 French catheter (Cook Medical). Using a glidewire, the target vessel was selected and embolized using a sterilized shear-thinning composition (6NC75) as described herein. Following the procedure, the catheter was removed and hemostasis at the puncture site was obtained using manual compression for up to 15 minutes. The animals were subsequently recovered and placed back into their cages.

Statistical Analysis

Two-tailed Student's t test were performed for experiments with 2 groups. One-way analysis of variance (ANOVA) with Tukey post hoc test ($p<0.05$ was defined as significant) were performed on experiments with more than 2 test groups. Standard deviation was the measure of uncertainty in all data. All statistical analysis and graphing were performed with the GraphPad Prism 5 software.

Example 1

Gelatin-Silicate Nanoparticle Composition Formulation

Stock solutions of 18% (w/w) gelatin and 9, 6, or 3% (w/w) silicate nanoplatelets were prepared in water. Milli-Q water was heated to 40° C. to dissolve gelatin and 4° C. water was used for nanoplatelet stock solutions to slow gelation and allow for full dissolution of nanoplatelet particles prior to gelling. The nanoplatelet gels were kept at room temperature to fully hydrate until a clear gel formed. The compositions were again heated and vortexed at 3000 rpm for 5 minutes to achieve the appropriate solid concentration and nanoplatelet loading. Once formed, the compositions were stored at 4° C.

Composition 9NC0 had a gel-sol transition temperature of 32° C., too low for application as a hemostat. However, the addition of silicate nanoplatelets to gelatin improved the thermal stability, increasing the sol-gel transition to above 45° C. for compositions having total solids concentrations of 6 weight percent or greater. In contrast, composition having a total solid concentration of 3 weight percent were not solid within the experimentally observed temperature range. Physiological stability was observed for all compositions having a total solids concentration of 9 weight percent. Physiological stability was also observed for compositions 6NC50, 6NC75, and 6NC100. Weight percentages of example compositions is shown below in Table 1.

TABLE 1

Example Shear-Thinning Compositions

| Composition | Gelatin (wt %) | Nanoplatelets (wt %) | Water (wt %) |
|---|---|---|---|
| 9NC0 | 9 | 0 | 91 |
| 9NC25 | 6.75 | 2.25 | 91 |
| 9NC50 | 4.5 | 4.5 | 91 |
| 9NC75 | 2.25 | 6.75 | 91 |
| 9NC100 | 0 | 9 | 91 |
| 6NC0 | 6 | 0 | 94 |
| 6NC25 | 4.5 | 1.5 | 94 |
| 6NC50 | 3 | 3 | 94 |
| 6NC75 | 1.5 | 4.5 | 94 |
| 6NC100 | 0 | 6 | 94 |
| 3NC0 | 3 | 0 | 97 |
| 3NC25 | 2.25 | 0.75 | 97 |
| 3NC50 | 1.5 | 1.5 | 97 |
| 3NC75 | 0.75 | 2.25 | 97 |
| 3NC100 | 0 | 3 | 97 |

Example 2

Composition Degradation

Composition samples were placed in 2.0 mL Eppendorf tubes and weighed. Each sample was centrifuged in a swinging bucket rotor centrifuge to obtain a flat interface. Each sample was then soaked in phosphate buffered saline (PBS, pH 7.4; Invitrogen), stored at 37° C. At set times, the PBS was removed, and the composition was reweighed. The change in weight was recorded up to 24 hours after initial soaking. PBS was replaced after each weighing.

Example 3

Small Angle X-Ray Scattering

Scattering measurements of gelatin-silicate nanoparticle compositions suggested the presence of disk shaped particles, indicating that clay particles remain exfoliated in the composition. Small Angle X-ray Scattering (SAXS) intensity curves of the compositions exhibited a power law decay with an exponent of −2 at high q, the scattering vector, characteristic of disk-shaped scatterers. The scattering intensity from 9NC75 can be fit with a thin disk model with a radius of 9.5±2.7 nm, in agreement with the reported size of the silicate nanoplatelets. The SAXS intensity curves suggest that scattering was produced from individual nanoplatelets dispersed within the gelatin and not aggregates of nanoplatelets.

Example 4

Effect of Silicate Nanoplatelets on Physiological Stability of Compositions

Storage modulus (G') and loss modulus (G") of gelatin and gelatin-silicate compositions with total solid concentrations of 9, 6, and 3 weight percent were monitored from 15° C. to 45° C. Gelatin (NC0) was observed to flow at all solid concentrations above 32° C. The addition of silicates improved the thermal stability of the composition network. All temperature sweeps were performed at 10 Pa stress and 1 Hz and are shown in FIGS. 1A-1C.

Example 5

Effect of Silicate Nanoplatelets on the Stability of Hydrogel Compositions in Physiological Solution Physiological stability was determined by measuring the weight of compositions with total solid concentration of 9, 6, and 3 weight percent stored in phosphate buffered solution (PBS) at 37° C. Gelatin (NC0) immediately dissolved in PBS, while compositions having a total solid concentration of 6 and 9 weight percent maintained their structural integrity throughout a 24 hour test.

Example 6

Linear Viscoelastic Range of Hydrogel Compositions

Figure 2:
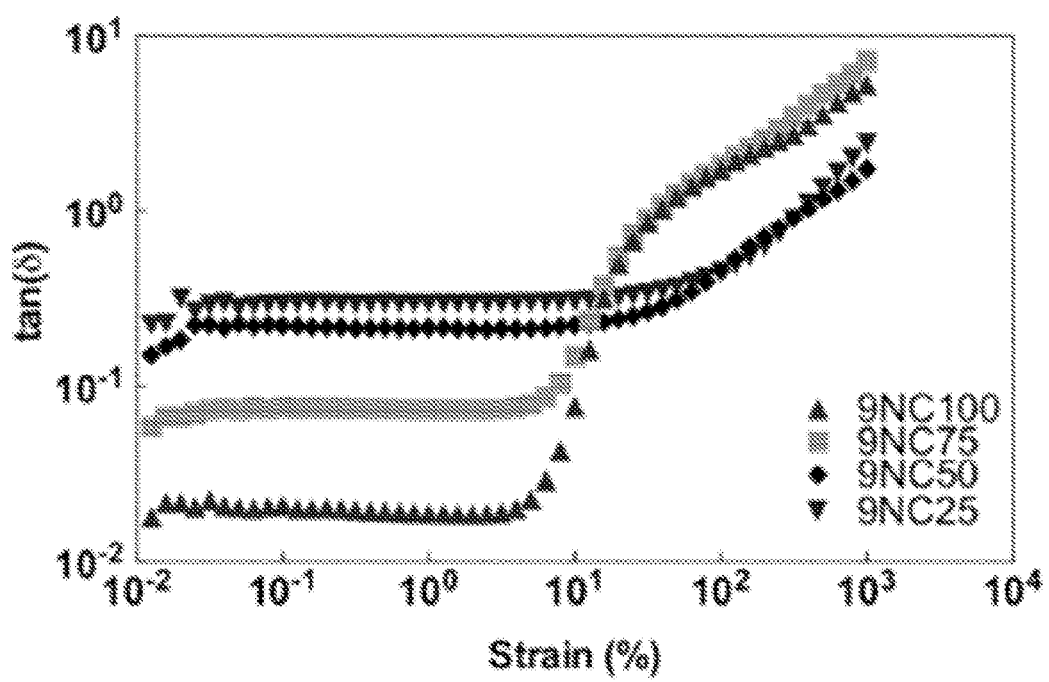
FIG. 2 shows strain sweep curves representative of compositions 9NC100, 9NC75, 9NC50, and 9NC25.
Figure 3A:
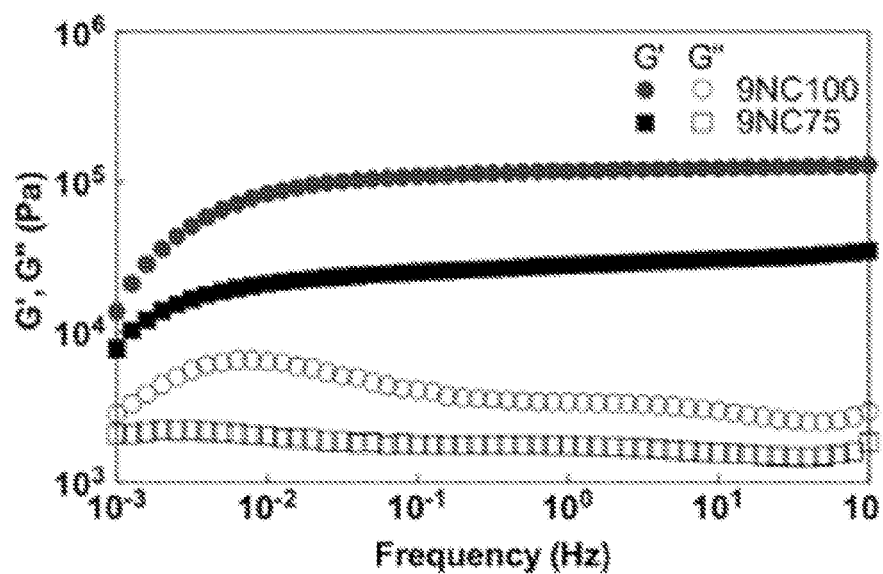
FIG. 3A shows frequency sweep curves representative of compositions 9NC75 and 9NC100 at 37° C.
Figure 3B:
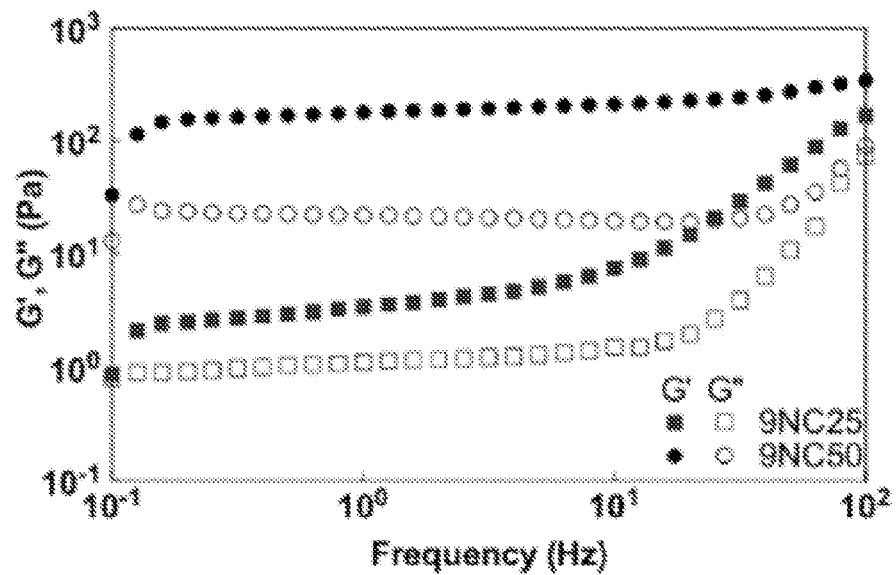
FIG. 3B shows frequency sweep curves representative of compositions 9NC25 9NC50 at 37° C.
Figures 4A, 4B, 4C:
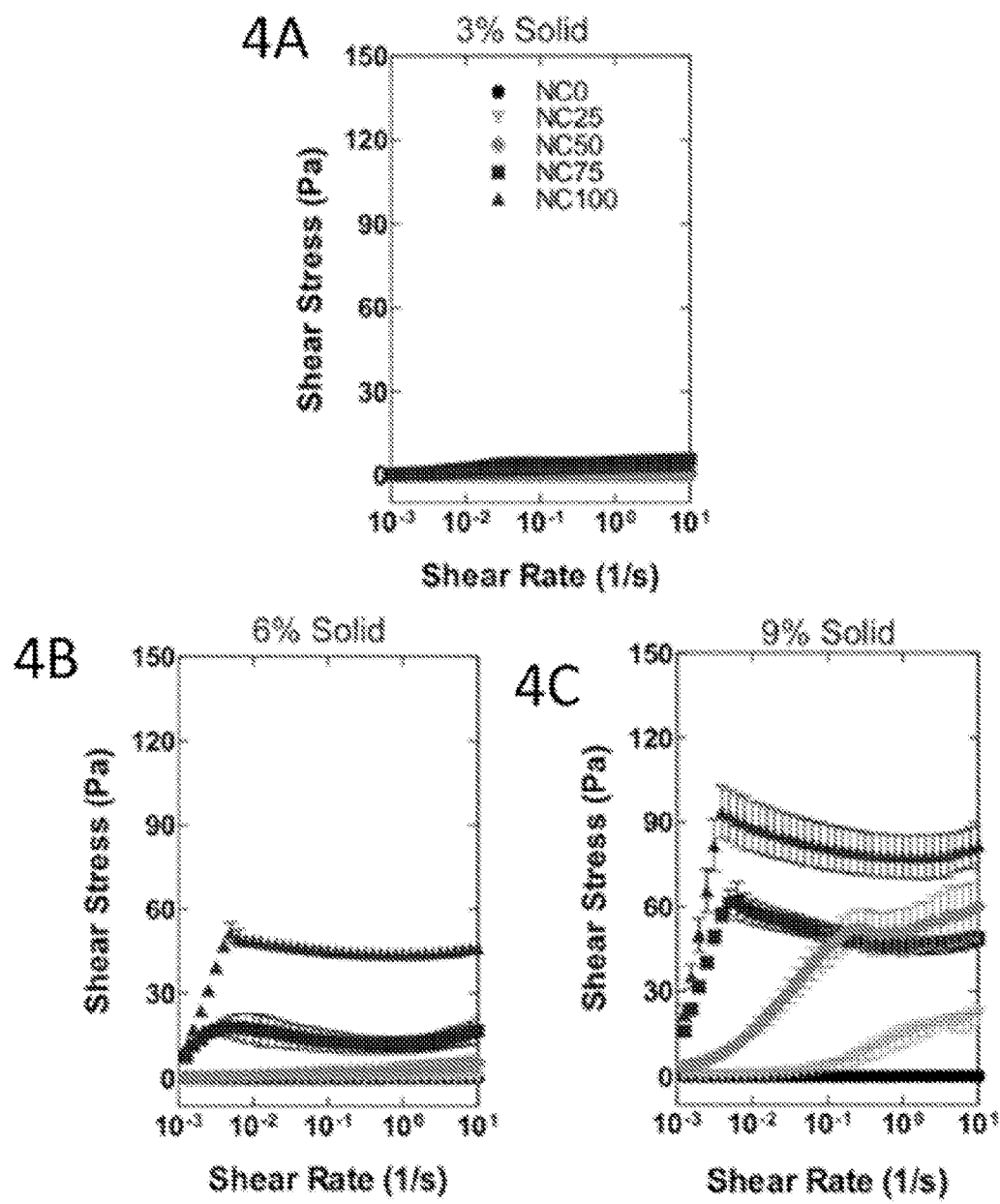
FIG. 4A shows yield stress curves representative of compositions comprising 3 total weight percent solids.
FIG. 4B shows yield stress curves representative of compositions comprising 6 total weight percent solids.
FIG. 4C shows yield stress curves representative of compositions comprising 9 total weight percent solids.
Figure 5:
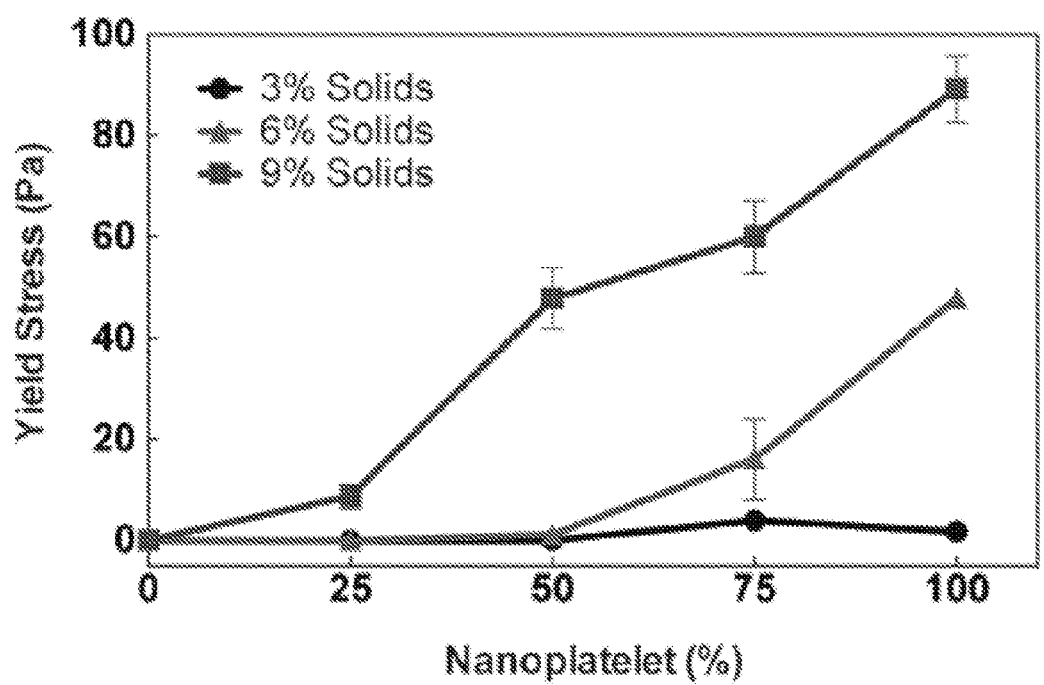
FIG. 5 shows the yield strength of compositions comprising 3, 6, and 9 total weight percent solids as a function of increasing concentrations of silicate nanoplatelets.

Silicate addition to gelatin modulated the rheological response of the compositions, resulting in a shear-thinning behavior observed at 37° C. Preliminary investigations using a 22-gauge needle indicated that all silicate-containing compositions could be injected and form self-supporting structures, suggesting the presence of a yield stress and recovery potential. Linear oscillatory shear rheology showed that the crossover frequency was below 0.001 Hz for 9NC75 and 9NC100, maintaining solid-like (G'>G") properties over the tested frequency range. Strain sweeps were performed at 1 Hz and indicated a crossover point when tan(δ)=1 that decreased with increasing silicate loading, as shown in FIG. 2. Frequency sweeps were performed at 37° C. Compositions 9NC25, 9NC50, 9NC75, and 9NC100 exhibited increased moduli for compositions with higher nanoplatelet loading, as shown in FIGS. 3A-3B. Oscillatory strain into the non-linear regime illustrated yielding behavior, an important parameter for designing hydrogels for minimally invasive therapies. Yield stress of gels as a function of nanoplatelet loading and total solid weight percent (3%, 6% and 9% solid) is shown in FIGS. 4A-4C. In oscillatory shear rate sweeps, the yield stress was defined as a 5% departure of the stress from the initial linearity on a stress-strain plot. Tests were performed at 37° C., where gelatin readily flows and lacks a yield stress. An increase in the silicate concentrations from 0% (9NC0) to 100% (9NC100) increased the yield stress from 2 Pa to 89 Pa, as shown in FIG. 5. A yield stress was observed in 9NC100 but not in 9NC0, suggesting that the yield stress behavior was derived from the presence of the dispersed nanoplatelets in the hydrogel composition, consistent with the known shear-thinning capability of nanoplatelets. Because increasing the concentration of gelatin reduces the yield stress, the presence of higher concentrations of gelatin eased delivery of the composition by injection.

Example 7

Gel Recovery and Aging

Recovery of the elastic gel strength in less than 10 seconds was observed in compositions for nanoplatelet loadings greater than 50% (9NC50, 9NC75, and 9NC100). Recovery was tested by straining above the crossover point, observed from strain sweeps, to break the network, resulting in $G''>G'$, followed by removal of the strain. Such rapid self-healing after the removal of stress can prevent material flow after application to a wound site. This provides a significant advantage over self-assembling peptides, which risk being washed away because they have relatively long self-healing times after the deformation of physically crosslinked networks. Results of the composition moduli indicate rapid recovery of the storage modulus after repeated application of high oscillatory strain amplitudes, suggesting rapid recovery of the physically crosslinked networks. After four cycles of high and low oscillatory strain, the modulus observed for composition 9NC50 during large amplitude strain oscillations was 80% lower than the initial modulus. At higher silicate loading (9NC75 and 9NC100), the moduli were 33% and 29% lower compared to the initial values. Extended monitoring indicated that after 30 seconds the moduli reached asymptotic values, indicating completion of the healing process. Aging of composition 9NC100 was observed when samples were monitored over a period of hours at 1% strain, 1 Hz. The effects of aging were able to be countered by application of high shear rates ($10 \text{ s}^{-1}$) prior to testing, which returned moduli to their initial, non-aged values.

Example 8

Zeta Potential Measurements

Solutions of silicate nanoplatelets possessed a zeta potential of −39 mV, whereas gelatin solutions had a zeta potential of 10 mV. Because the two components had opposite charges, electrostatic interactions between silicate and gelatin were expected. This was also supported by earlier findings which showed that strong interactions between montmorillonite (another type of silicate clay) and gelatin can function to increase the sol-gel transition temperature of the composite. Zeta potential measurements suggest that electrostatic interactions between nanoplatelets and gelatin contributed to the observed increase in the thermal stability.

Example 9

In Vitro Flow Models

Figures 6A, 6B, 6C:
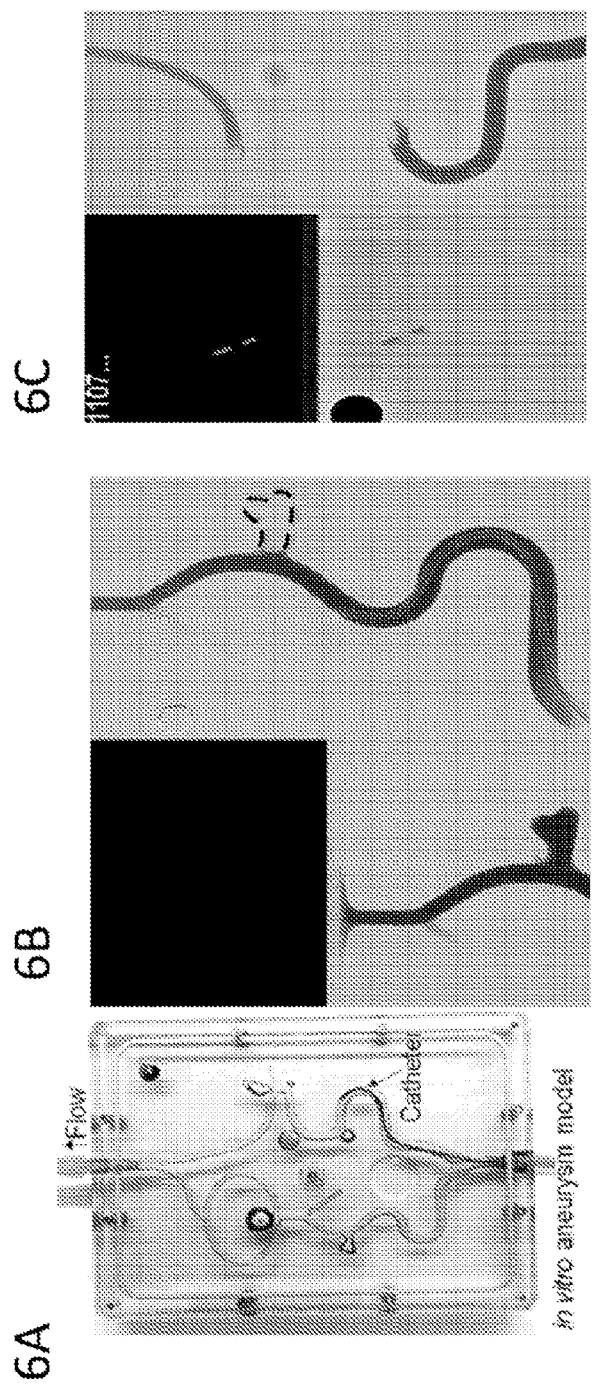
FIGS. 6A-6C shows an in vitro aneurysm model.

Using an in vitro aneurysm model (FIGS. 6A-6C), shear-thinning compositions were injected using a 5 French catheter (FIGS. 6B-6C). As shown in FIG. 6B, approximately 2 cc of the composition was injected during real-time fluoroscopy guidance. Subsequent contrast injection demonstrates absence of the wide neck aneurysm sac. As shown in FIG. 6C, to simulate gastrointestinal bleeding and its treatment, a long segment main branch received an injection of the shear-thinning composition (segment in between dotted lines). Subsequent contrast injection demonstrates exclusion of the injected segment. A unique property of this composition is that hemostasis is not coagulation dependent. The shear-thinning composition produces a cast of the injected vessel or aneurysm preventing flow into this segment. In modern treatments, coil embolization are generally performed; these coils rely on adequate coagulation for hemostasis. There is significant clinical failure of coil embolization cases often seen in coagulopathy patients; such failure would be a non-issue when using shear-thinning compositions.

Figure 6D:
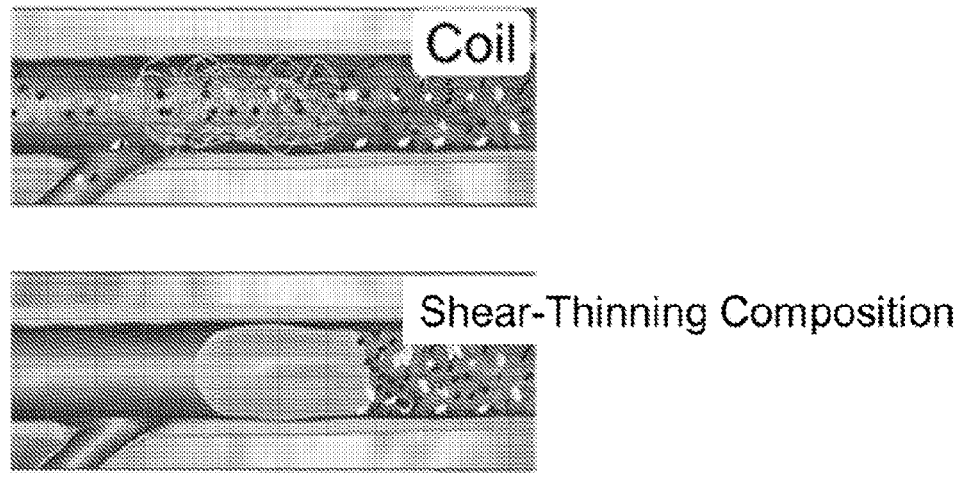
FIG. 6D shows a schematic of PDMS tube-based set-up utilizing a syringe pump and a pressure gauge to assess the pressure required to push anticoagulated blood through the PDMS tube containing only coils or only shear-thinning composition compared to blood alone (control).
Figure 6E:
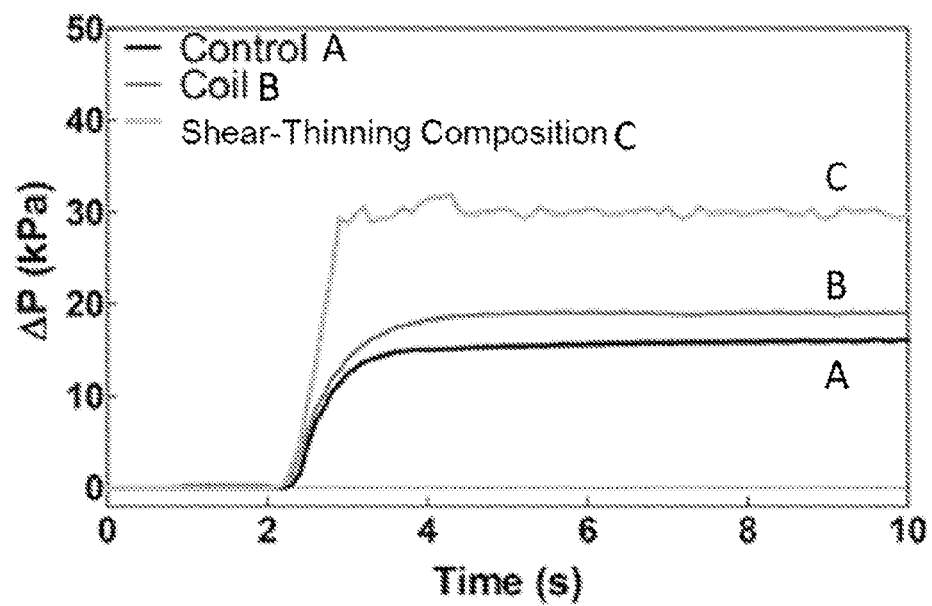
FIG. 6E shows pressure curves over time showing the pressure required to push anticoagulated blood through the PDMS tube containing blood (control), coil, and shear-thinning composition.
Figure 6F:
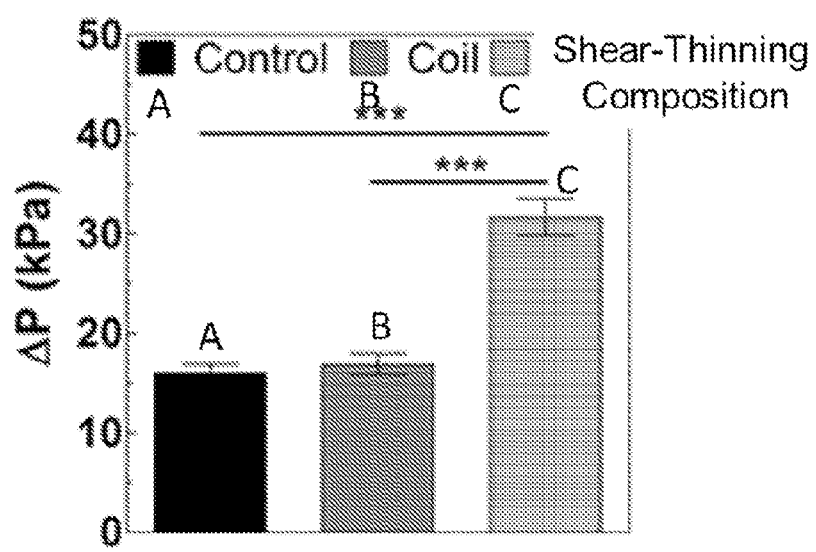
FIG. 6F shows pressure curves over time showing the pressure required to push anticoagulated blood through the PDMS tube containing anti-coagulated blood (control), coil, and shear-thinning composition. (N=3; ns: P>0.05; *: P≤0.05; : P≤0.01; *: P≤0.001; statistical significance determined by one-way analysis of variance with Tukey post hoc comparisons).

In a further example, anticoagulated whole blood (citrated, Research Blood Components) was flowed through a PDMS tube (ID: 4 mm, wall modulus: approximately 500 kPa) with a syringe pump, with the pressure being monitored upstream (FIG. 6D). A 5-French (ID: 1.7 mm) catheter was fed through the tubing to inject coils or shear-thinning composition directly into the PDMS mimic vessel. The catheter was removed, flow was started, and the pressure was measured until movement of the embolic agents in the tube. FIG. 6E shows pressure curves over time, which show that the control and coil samples are similar, reproducing the clinical scenario. The shear-thinning composition, however, requires significantly higher pressures to displace even when anticoagulated blood is used (FIG. 6F).

Example 10

Shear-Thinning Composition Catheter Injectability—Dependence on Temperature

Figures 7A, 7B, 7C:
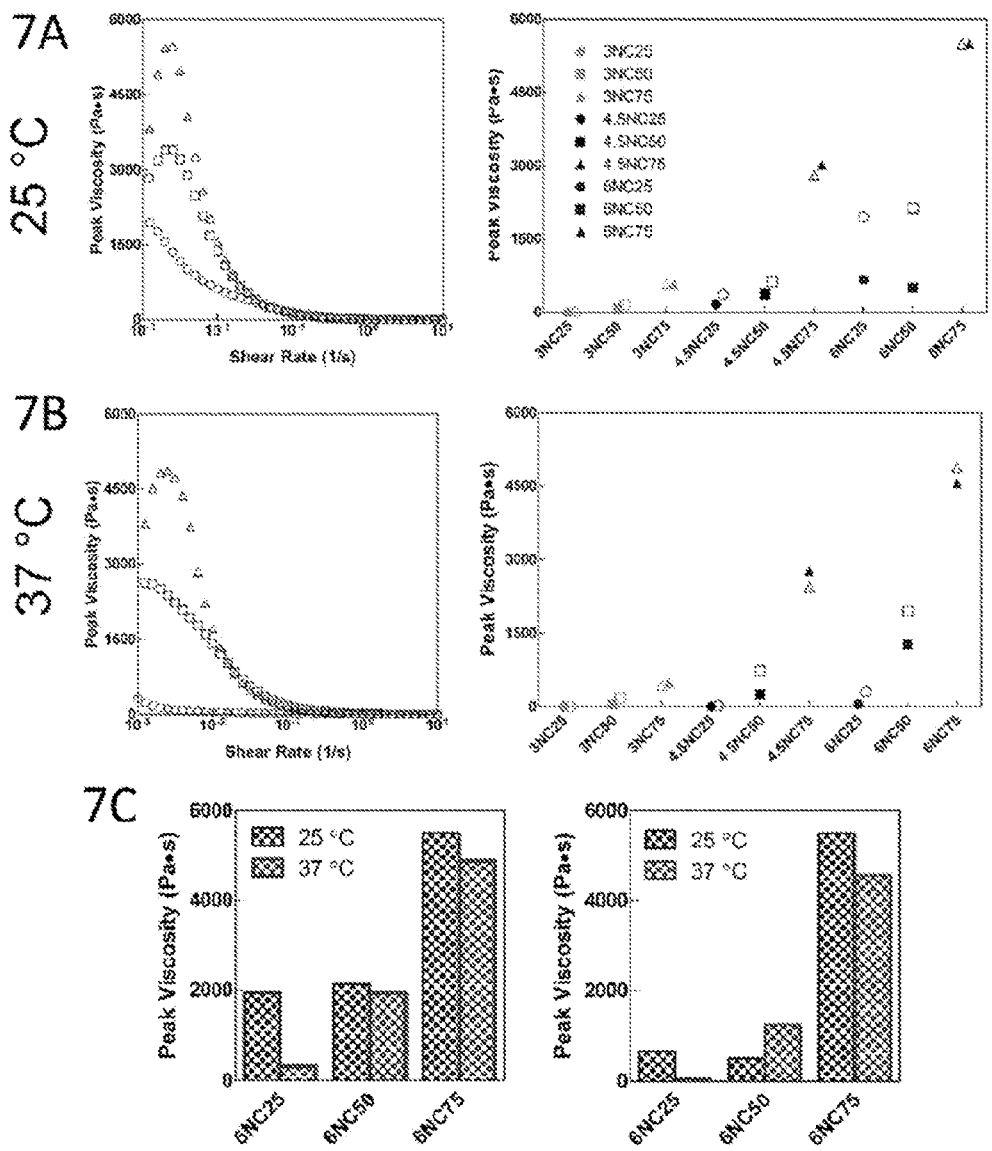
FIGS. 7A-7F shows the catheter injectability dependence on temperature for shear-thinning compositions.
Figures 7D, 7E, 7F:
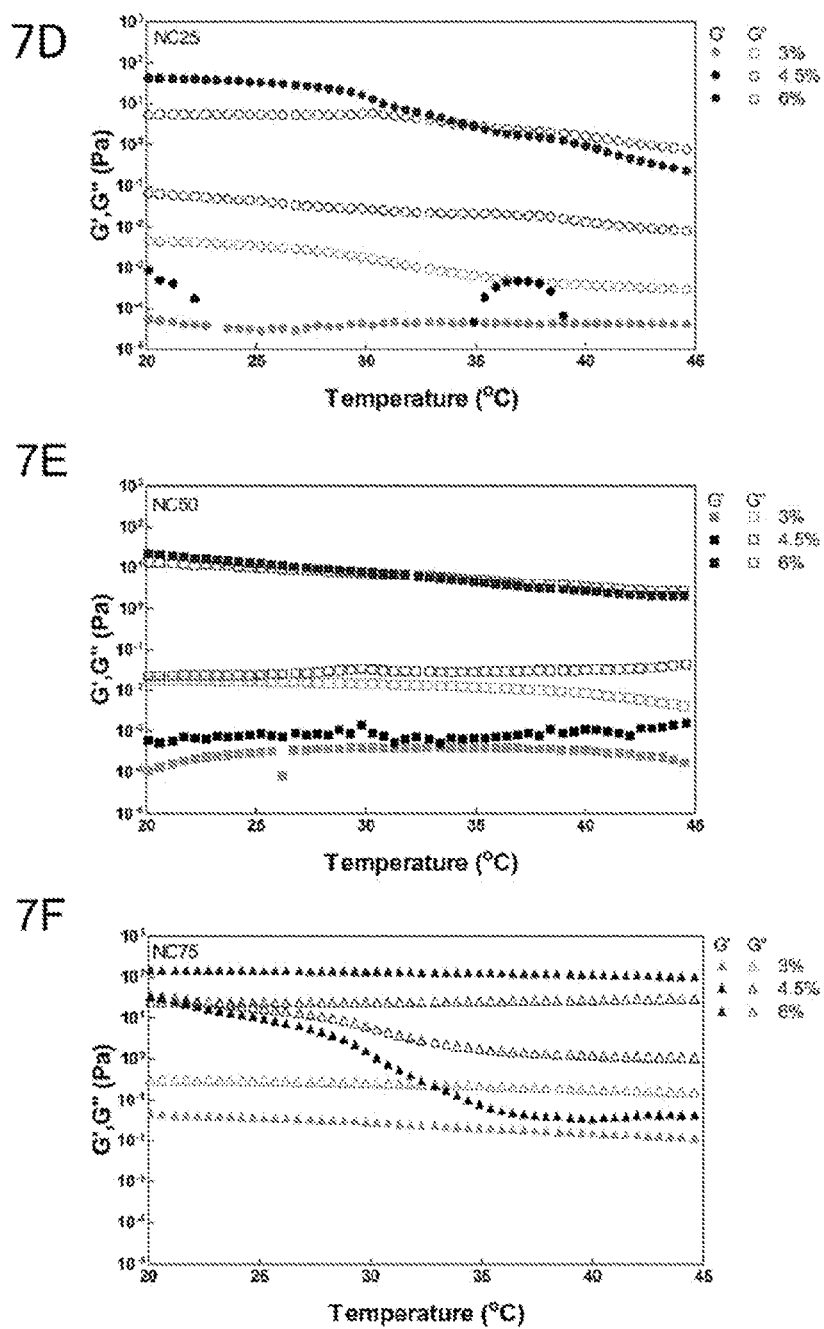

Shear-thinning compositions were characterized utilizing rheology to measure the mechanical properties of the shear-thinning composition. It can be used to determine the viscosity of materials under a variety of conditions such as changing temperature and applied torques, which can model the process of injection through a syringe, catheter, or needle. As shown in FIGS. 7A-7B, the shear-thinning composition was subjected to multiple injection rates (termed shear rates in rheological terms) and temperatures while measuring viscosity. Higher shear rates reflect a faster rate of injection and lower viscosity values reflect a material that is easier to flow (e.g. water has a lower viscosity than honey). In shear-thinning materials, once the viscosity begins to decrease, the material is "shear-thinning" and begins to flow. As the percent of silicate nanoplatelet is increased, the maximum viscosity attained prior to flowing (when the viscosity begins to decrease) is increased as shown in FIG. 7A. After waiting 5 minutes, the material is still able to be injected, summarized for multiple compositions in FIG. 7A (right trace) and FIG. 7B (right trace), with open symbols for the initial peak viscosity and closed symbols representing the peak viscosity after 5 minutes. The ability to pause and re-inject an embolic material is unique to shear-thinning compositions and something that is not possible today with metal coils or commercial embolics (see e.g., Onyx embolic agents). As shown in FIG. 7C, the temperature dependence is shown to be statistically insignificant when higher nanoplatelet concentrations are used, for initial peak viscosities FIG. 7C (left trace) and peak viscosities after 5 minutes FIG. 7C (right trace). Indeed, the temperature stability of the shear-thinning compositions is highlighted when the stiffness is monitored over a range of temperatures, from 15 to 45° C. (FIG. 7D-7F). At higher nanoplatelet compositions (e.g., FIG. 7F), there is independence in mechanical properties on the applied temperature.

Example 11

Shear-Thinning Composition Injectability—Dependence on Time

Figures 8A, 8B:
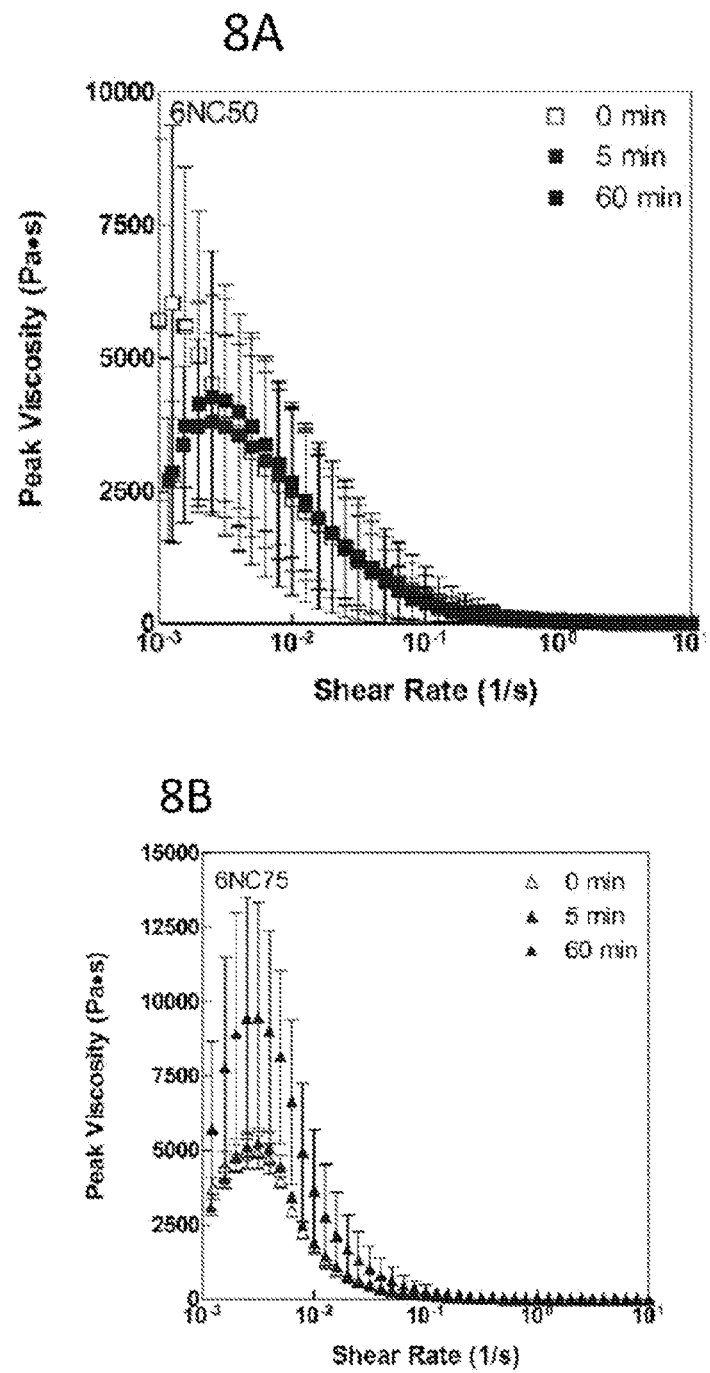
FIGS. 8A-8C shows the injectability dependence on time for shear-thinning compositions.
Figure 8C:
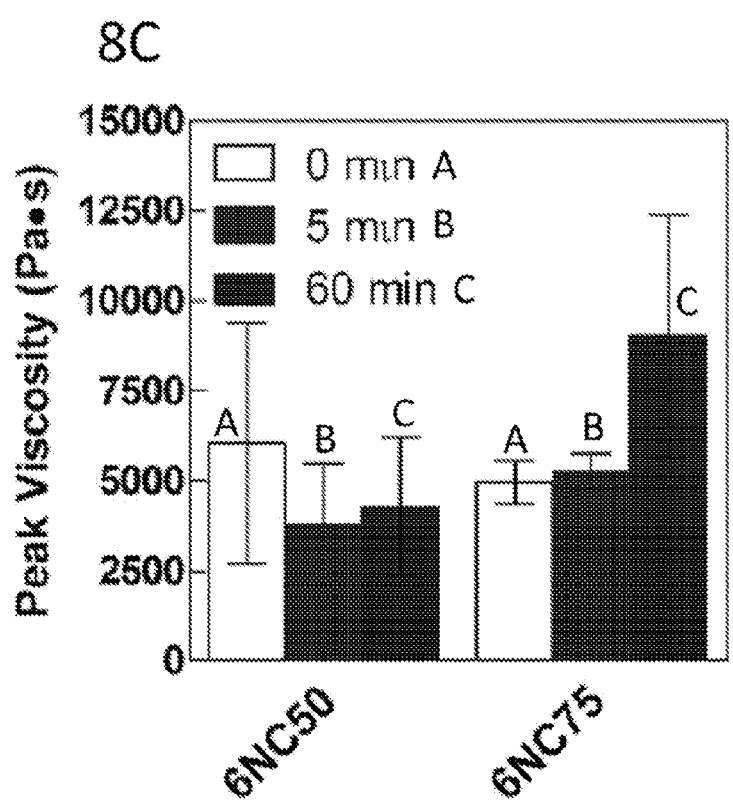

Longer term monitoring of shear-thinning composition injectability shows a statistically insignificant change in the peak viscosity over the span of 1 hour after the injectability was initially measured, as shown in FIGS. 8A-8C. This suggests that the shear-thinning composition is not hardening after equilibrating over 1 hour, highlighting the ability to keep the embolic in a catheter for the extent of a 1 hour procedure. This is a unique property of shear-thinning compositions; during embolization procedures, for example, the operator can stop and reassess progress and then continue safely with the procedure. In contrast, there is minimal time to pause when performing coil embolization to avoid occluding a microcatheter with thrombus and there is no time to pause and assess progress using Onyx embolic agents to avoid cementing the catheter to the embolic agent.

Example 12

Shear-Thinning Composition Recoverability

Figure 9A:
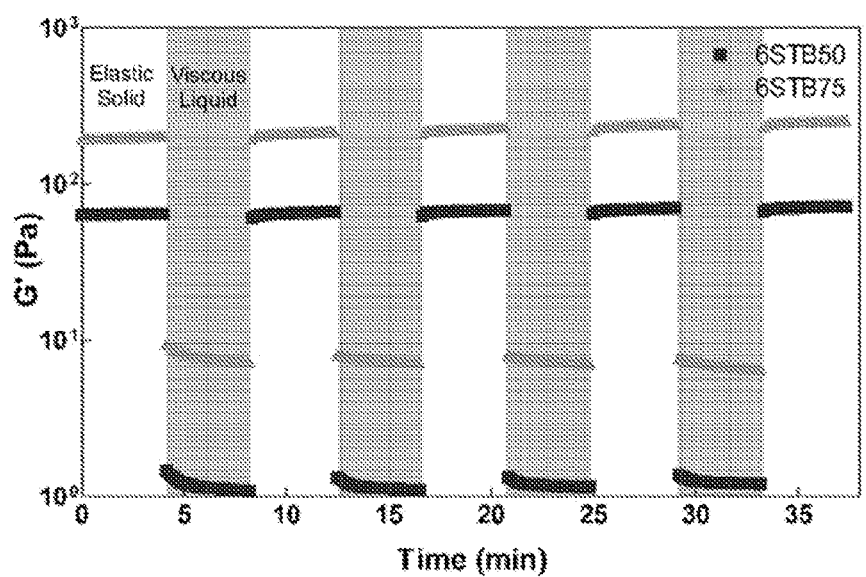
FIGS. 9A-9B shows recoverability of shear-thinning compositions (6STB50=6NC50; and 6STB75=6NC75).
Figure 9B:
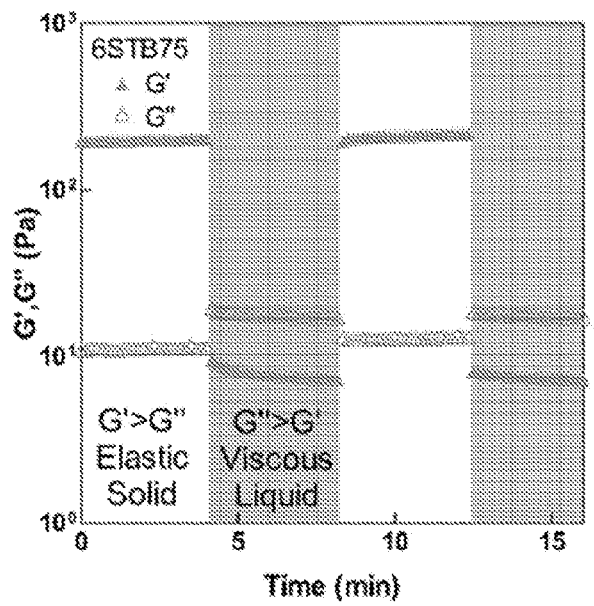

The stiffness of the shear-thinning composition is modified from an elastic solid to a viscous liquid as the deformation of the shear-thinning composition is changed. However, it is able to recover its stiffness after multiple cycles of high and low deformation without weakening, as shown in FIGS. 9A-9B. This highlights the rapid recovery of the shear-thinning composition stiffness after high deformation that is experienced during injection.

Example 13

Shear-Thinning Composition Injectability Through Catheters

Figures 10A, 10B, 10C, 10D:
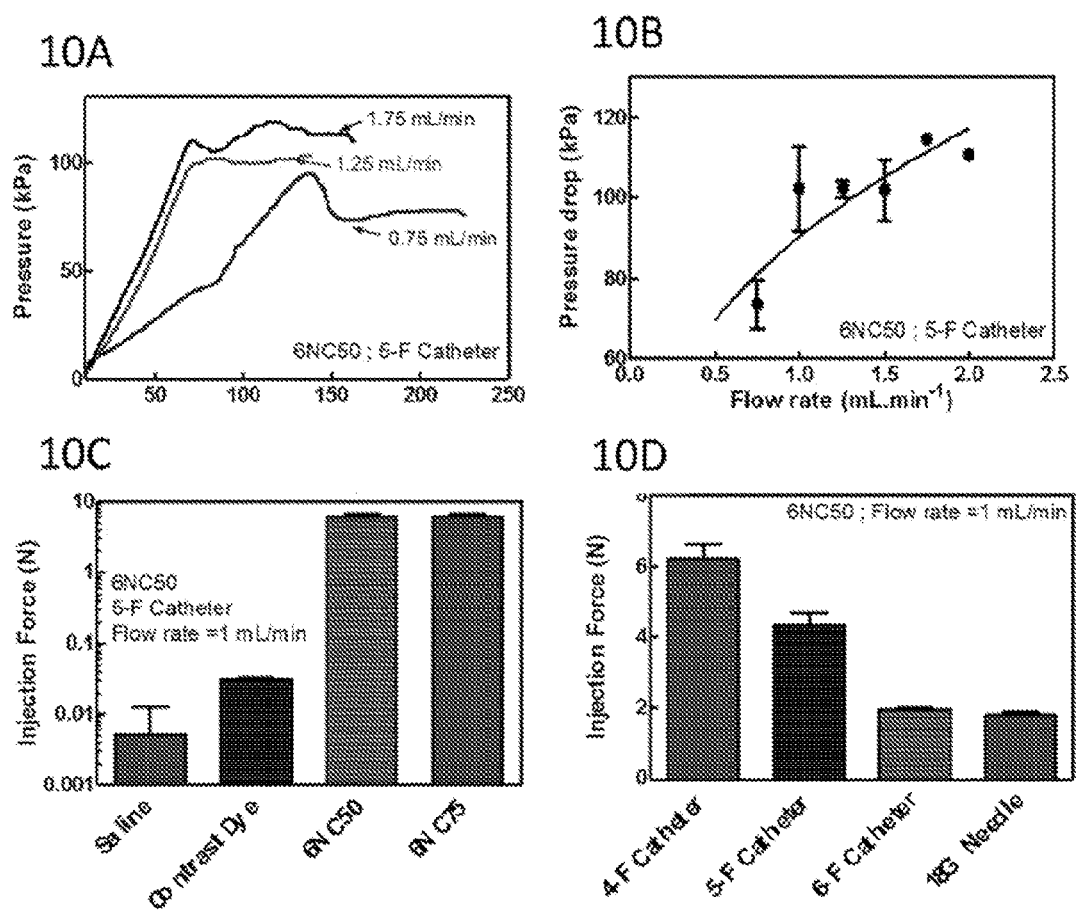
FIGS. 10A-10D shows injectability of shear-thinning compositions through catheters and needles.

Using a syringe pump and system of valves and pressure, the pressure needed to inject the shear-thinning composition through catheters and needles can be measured. The injection pressure is dependent on how quickly the shear-thinning composition is injected, as shown in FIGS. 10A-10B. Compared to standard liquids injected through catheters, (e.g., saline solutions and contrast dye), the shear-thinning compositions require more force to inject, as shown in FIGS. 10C-10D but all forces needed are below the maximum functional pressure of many catheters (approximately 1.4 MPa).

Example 14

Thrombosis Potential of Shear-Thinning Compositions

The time it commonly takes for blood to clot outside of the body is 5-7 minutes. One example of a shear-thinning composition contains silicate nanoplatelets, which accelerate the speed of blood clotting. The utilization of clays (e.g., silicate nanoplatelets) to impact blood clotting has already been shown to work in topical hemostats such as QuikClot. Compared to controls, increased shear-thinning composition concentrations accelerate the clotting time to 3-5 minutes, as shown in FIGS. 11A-11B. These results are similar to the currently used fibered metallic coils, as shown in FIG. 11C. These properties, for example, will allow for a clot to fill an aneurysm sac and produce a cast of the sac. The strength of the clot can improve the stability of the embolic.

Example 15

Shear-Thinning Composition Hemocompatibility and Physiological Stability

Figure 12A:
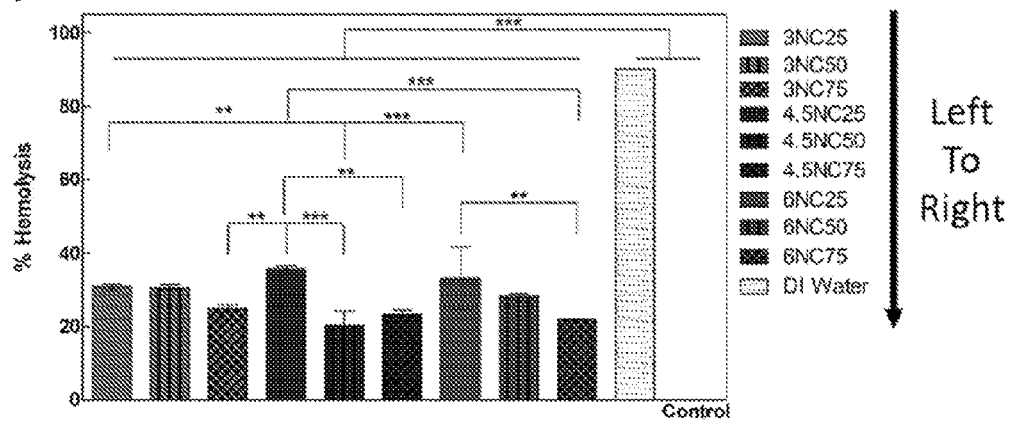
FIGS. 12A-12B shows hemocompatibility and physiological stability of shear-thinning compositions.
Figure 12B:
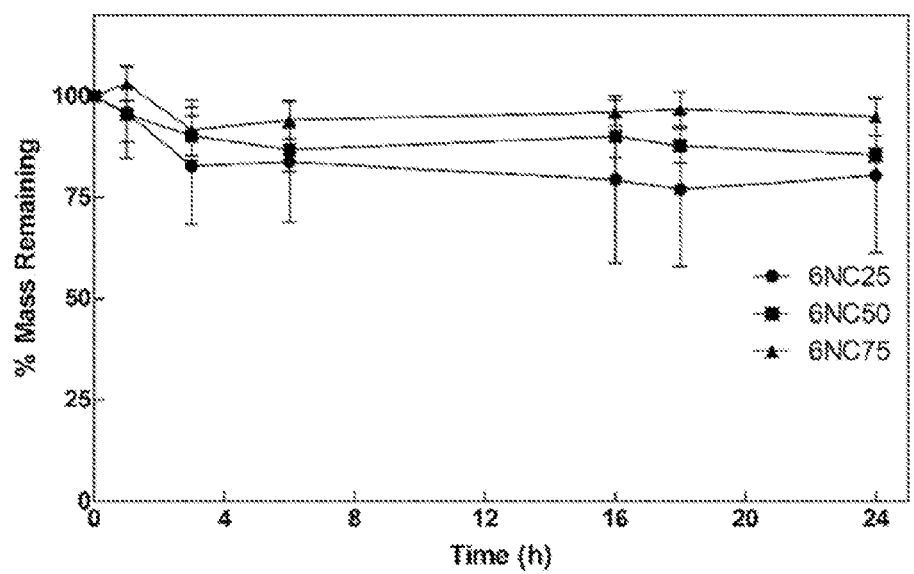

The interactions of blood with the shear-thinning composition are characterized by the level of red blood cell lysis, termed hemolysis. Stiffer shear-thinning compositions have lower hemolysis percent, as shown in FIG. 12A. Additionally, incubation of shear-thinning compositions in blood plasma showed no significant change in the shear-thinning composition mass over the span of 24 hours, as shown in FIG. 12B.

Example 16

Viscosity Measurements

Figure 13:
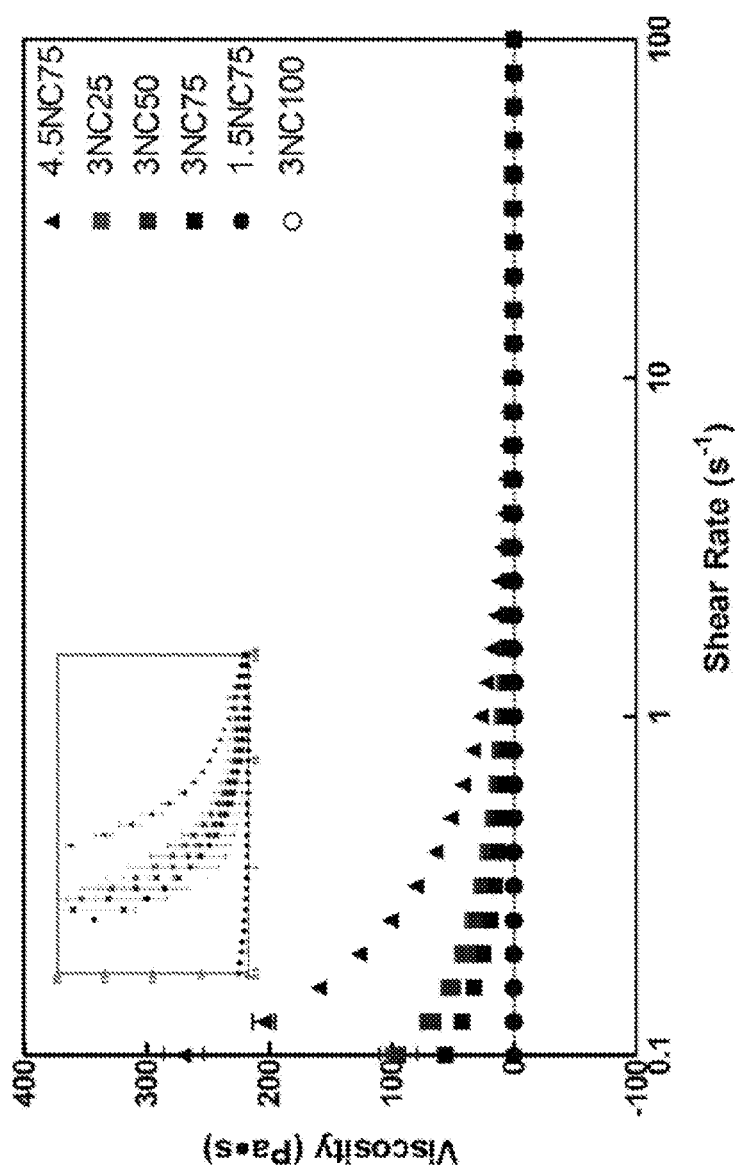
FIG. 13 shows viscosity as a function of injection rate (shear rate) for six shear-thinning compositions.

Viscosities of shear-thinning compositions from 1.5-4.5 wt. % were tested for their injectability by monitoring viscosity as injection rate (shear rate) was increased by rheology, as shown in FIG. 13. Using the correlation between flow rate and shear rate (injection rate), flow rates were converted to shear rates, as shown below in Table 2 and the resulting viscosity observed at this shear rate was determined from the viscosity curves as shown below in Table 3. During flow, the observed viscosities of these shear-thinning compositions are comparable to castor oil or corn syrup, highly viscous but able to flow when subjected to sufficient forces.

Correlation Between Flow Rate and Shear Rate $$\gamma = 4Q/\pi r^3 \qquad \text{Equation 3.}$$

TABLE 2

Flow Rate and Shear Rate

| Flowrate (mL/min) | Shear Rate (s$^{-1}$) |
|---|---|
| 0.1 | 17.0 |
| 0.2 | 34.0 |
| 0.3 | 50.9 | r = 0.5 mm

TABLE 3

Viscosity Values from Rheology
Viscosity Values from Rheology (Pa · s)

| Q (mL/min) | 0.1 | 0.2 | 0.3 |
|---|---|---|---|
| 1.5NC75 | 0.1 | 0.04 | 0.04 |
| 3NC75 | 0.7 | 0.4 | 0.3 |
| 4.5NC75 | 3.1 | 1.9 | 1.3 |
| 3NC25 | 0.9 | 0.4 | 0.3 |
| 3NC50 | 1.3 | 1.4 | 1.1 |

Example 17

Vasculature Microfluidic Model

Figures 14A, 14B, 14C:
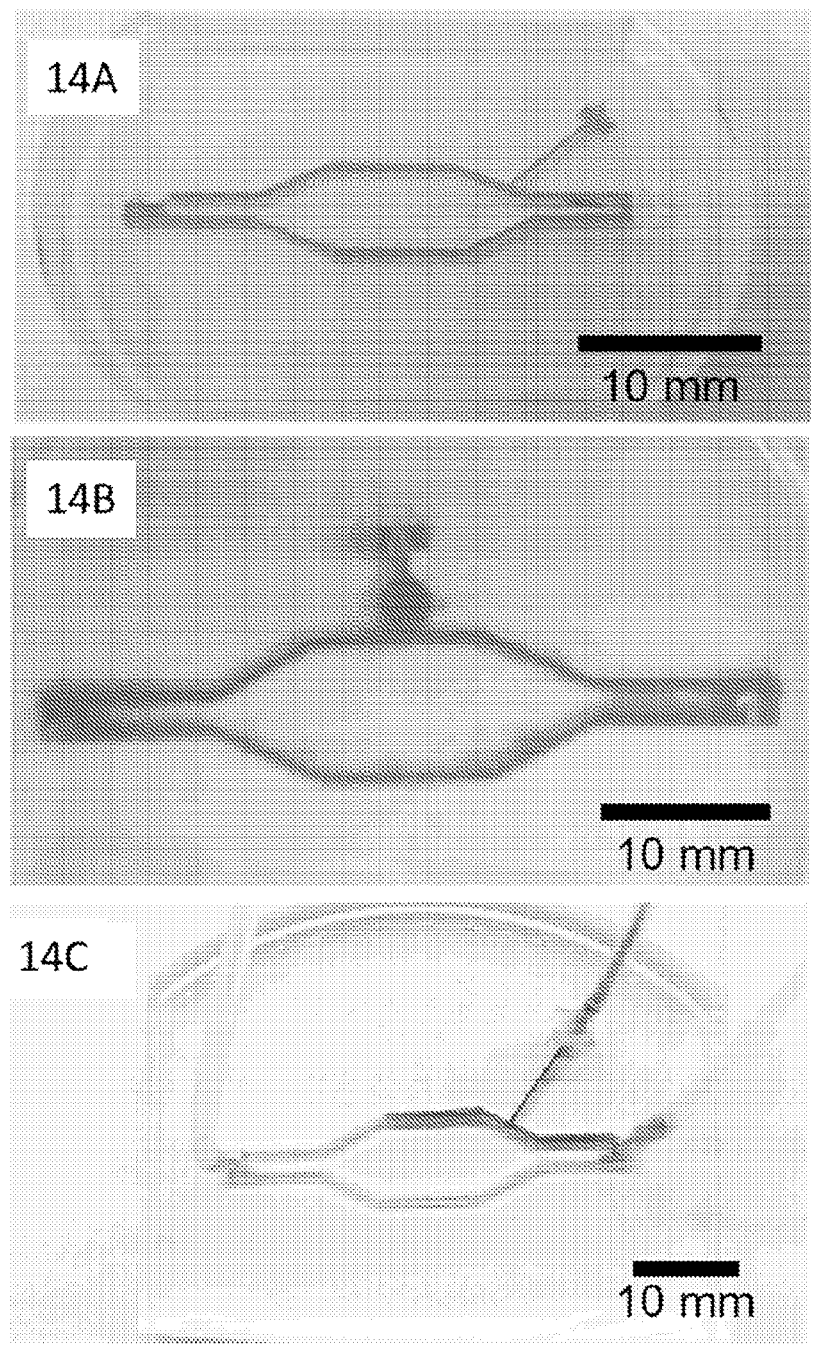
FIGS. 14A-14C shows vasculature microfluidic models used to assess shear-thinning composition stability and dynamic performance.

Ongoing tests are being performed within microfluidic flow systems. From these tests, the shear-thinning composition performance under high pressure and flow can be analyzed for stability and disruption or degradation of the shear-thinning composition. Models that can replicate vessel occlusion, as shown in FIG. 14A and aneurysm embolization, as shown in FIG. 14B have been developed from simple PDMS microchannels. The shear-thinning composition (dyed blue) is stable in the microfluidic system with flowing water (dyed green) at 37° C., as shown in FIG. 14C.

Example 18. Chitosan-based Shear-Thinning Composition

Figure 15:
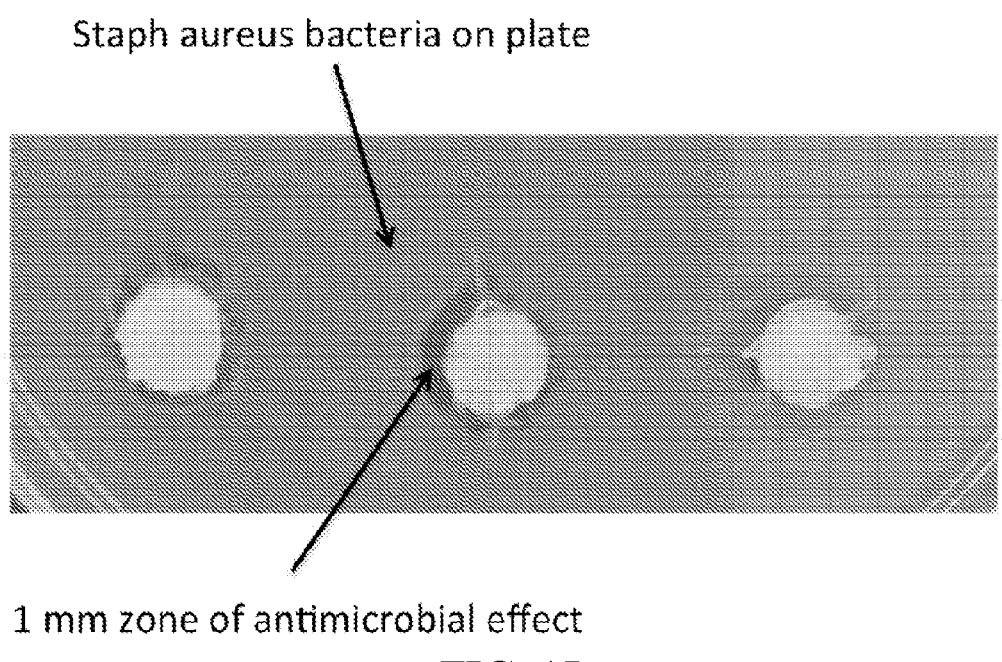
FIG. 15 shows antimicrobial effects of shear-thinning compositions comprising 8% chitosan.

As shown in FIG. 15, a shear-thinning-Chitosan composition (8% chitosan) produced approximately 1 mm of bacteria free zone when the composition is placed onto a confluent Staphylococcus aureus plate.

Example 19

In Vivo Mouse Model Vessel Occlusion

Figures 16A, 16B, 16C, 16D, 16E:
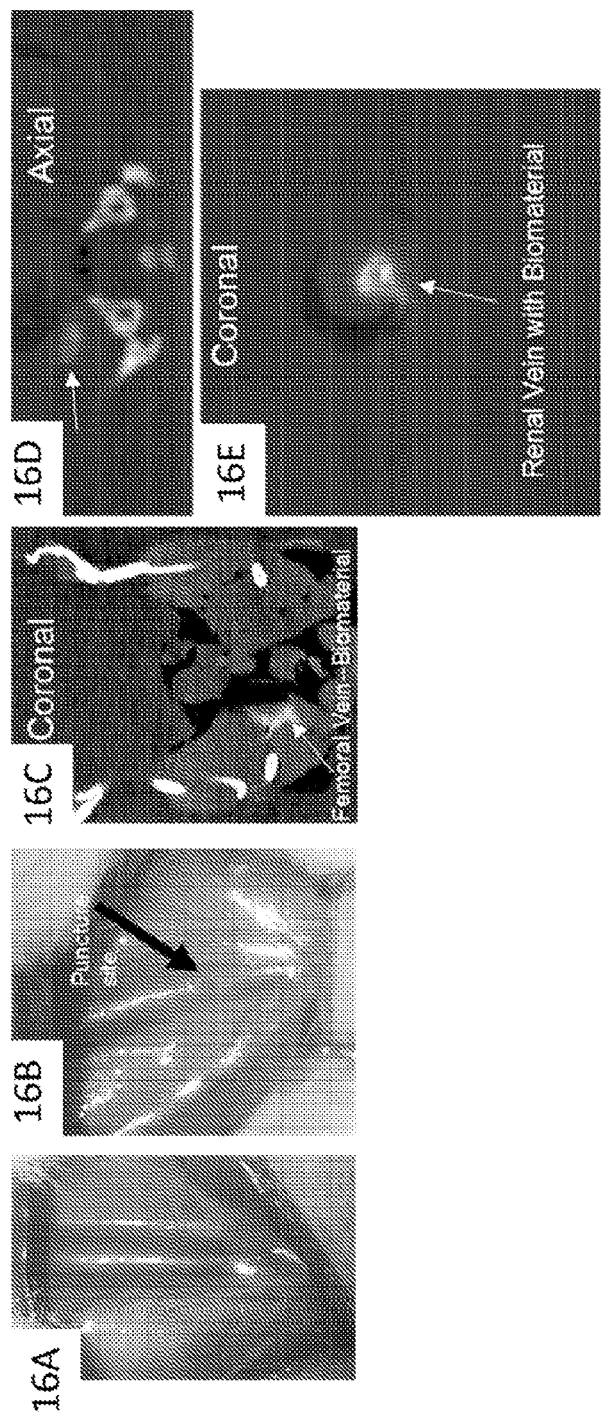
FIGS. 16A-16E show in vivo vessel occlusion using shear-thinning compositions.
Figures 16F, 16G, 16H:
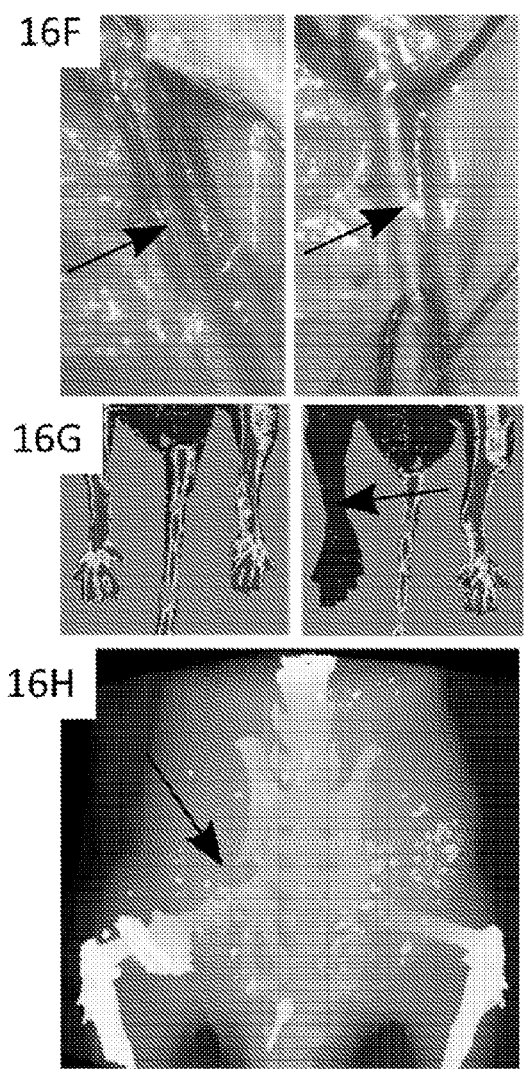
FIG. 16F shows representative photographs of a mouse femoral artery before and after injection of a shear-thinning composition via a 30 G needle.
FIG. 16G shows Laser Doppler microperfusion images showing that hind limb perfusion was maintained in the leg before the shear-thinning composition injection (left panel) but was interrupted after shear-thinning composition injection (right panel).
FIG. 16H shows a micro-CT (µCT) image of mouse after shear-thinning composition (6NC75 with Visipaque™; artificially colored and highlighted by the black arrow) injection showing the injected radiodense biomaterial stable in the femoral artery, consistent with ex vivo experiments described herein.

These experiments were performed to demonstrate that, following intravascular shear-thinning composition injection, the composition remains within the injected site and takes the shape of the vasculature without fragmentation despite blood pressures that exceed physiologic human systolic pressures and heart rates>400. The right groin was exposed revealing the femoral vasculature, shown in FIG. 16A, and approximately 200 μL of the 6% shear-thinning composition formulation was injected, as shown in FIG. 16B. The black arrow indicates the vessel puncture site; slight blanching of the vessel can be seen suggesting proximal and distal flow of the shear-thinning composition producing an occlusive cast. Similarly, the left flank was exposed revealing the left renal vasculature; 200 μL of the shear-thinning composition was again injected (not shown). Approximately 4 hours later, an ultrahigh resolution CT imaging was performed (0.4 mm×0.4 mm slice thickness reconstructed at 0.4×0.1 mm, 240 mA, KV 120, rotation time 1 sec, Pitch 0.85; 53 mGy, DLP 1738 mGycm); the composition is indicated by the arrow in the coronal and axial views, as shown in FIGS. 16C-16E. In each case, the shear-thinning composition successfully produced a cast of the vasculature without any evidence of fragmentation and non-target embolization. The shear-thinning composition was mixed with Visipaque contrast solution to help visualize the composition during CT imaging. No evidence of non-target contrast enhancement was identified in these state-of-the-art ultrahigh resolution CT imaging. Additional images are shown in FIGS. 16F-16H.

Example 20

Creep and Creep Recovery

Creep tests were performed on an Anton Paar MCR702 SingleDrive system with a disposable aluminum cone geometry (25 mm diameter, 1° angle, 50 μm truncation gap) and a sandblasted lower plate. Tests were performed at 37° C. and samples were sealed with mineral oil to prevent sample drying. Shear-thinning composition 6NC75 was loaded and creep was measured by applying stresses (σ) of 10, 20, and 30 Pa for 30 min, followed by relaxation for 30 min and monitoring the resulting strain (ε). Creep compliance was calculated according to Equation 4 from the 20 Pa creep curve and used to extrapolate the strain expected at 1, 2, 3, and 4 Pa (10-40 dynes/cm²), shear stress values experienced along the wall of vasculature (see e.g., Lopera et al, Semin. Intervent. Radiol. 2010, 27:14-28).

$$J(t) = \epsilon(t)/\sigma \qquad \text{Equation 4.}$$

Figure 17A:
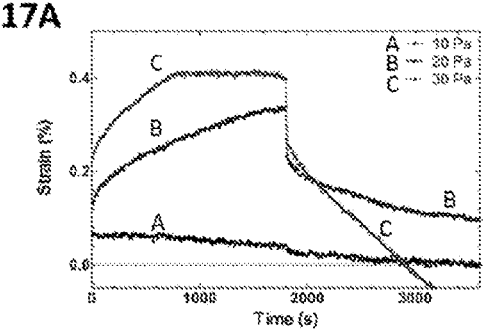
FIG. 17A shows creep and creep recovery of 6NC75 at 10, 20, and 30 Pa.
Figure 17B:
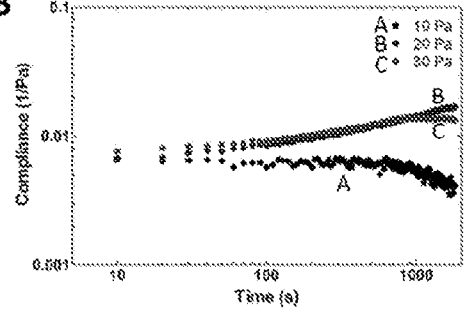
FIG. 17B shows compliance curves from 10, 20, and 30 Pa creep data.
Figure 17C:
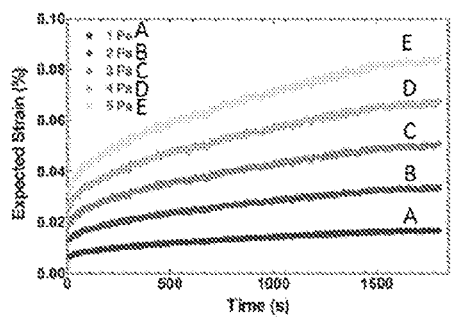
FIG. 17C shows the compliance curve derived from the 20 Pa creep curve ($J_{20\ Pa}(t)$) used to extrapolate the creep response at lower stress values (1-4 Pa) that are experienced along a vasculature wall (1-4 Pa).
Figures 18A, 18B, 18C, 18D, 18E:
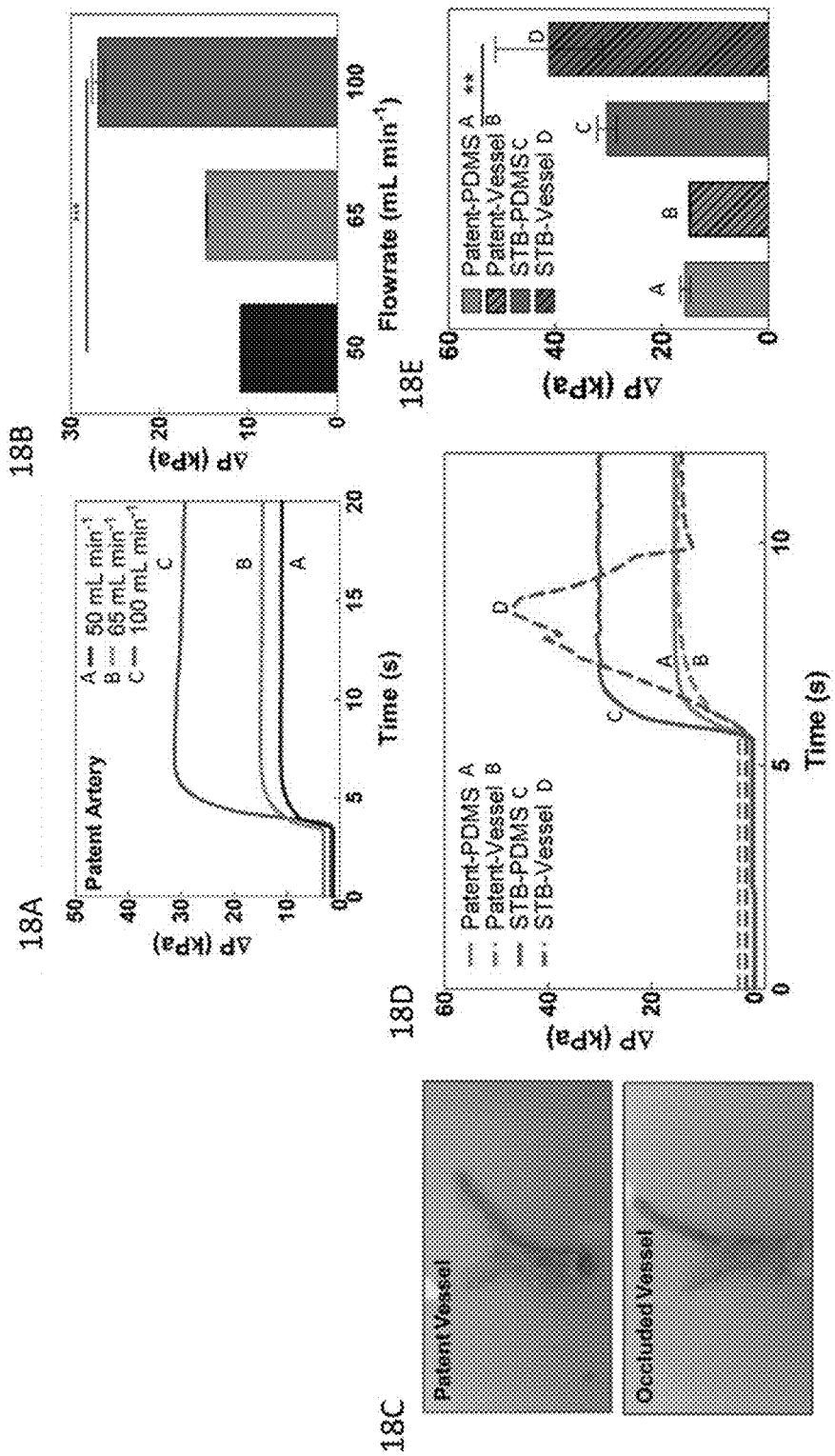
FIG. 18A shows the dependence of measured pressure on syringe pump flow rate.
FIG. 18B shows average pressure after equilibration.
FIG. 18C shows a representative image of excised arteries utilized for the ex vivo assay described herein, imaged patent and occluded with shear-thinning composition 6NC75 (dyed blue).
FIG. 18D shows pressure curves of patent and shear-thinning composition occluded arteries and PDMS tubes.
FIG. 18E shows significant differences between the pressure measured in STB occluded arteries and PDMS tubes. Without being bound by theory, the differences are believed to be due a rapid change in diameter encountered in the case of the artery when it was attached to the tubing of the pressure measurement device, causing a rapid peak as opposed to a more gradual increase in the case of PDMS tube of the same diameter with the device tubing. (N=3; ns: P>0.05; *: P≤0.05; : P≤0.01; *: P≤0.001 determined by one-way analysis of variance with Tukey comparison for FIG. 18A and FIG. 18E).

FIGS. 17A-17B show creep and creep recovery of a representative intravascular shear-thinning composition, 6NC75 (FIG. 17A) and compliance curves from creep data (FIG. 17B). The compliance curve derived from the 20 Pa creep curve ($J_{20\ Pa}(t)$) was used to extrapolate the creep response at lower stress values (1-4 Pa) that are experienced along a vasculature wall (1-4 Pa) as shown in FIG. 17C. Expected creep caused by physiologically relevant stresses is below 1% strain and, therefore, is likely not a source of hydrogel deformation following delivery into the vasculature. Almost complete recovery after shear was observed, suggesting minimal permanent deformation in the shear-thinning composition.

Example 21

Ex Vivo Occlusion

Simulated Body Fluid (SBF; 8.035 g sodium chloride, 0.355 g sodium bicarbonate, 0.225 potassium chloride, 0.231 g potassium phosphate dibasic, 0.311 g magnesium chloride hexahydrate, 39 mL 1 M hydrochloric acid, 0.292 calcium chloride, 0.072 sodium sulfate, 6.118 g Tris per 1 L SBF) was made with 22% (w/w) glycerol to simulate whole blood (see e.g., Marques et al, Dissolution Technol. 2011, 18:15-28). Porcine aorta and abdominal vasculature was acquired from Research 87, Inc. Vasculature including the aortic bifurcation and iliac arteries was excised and zip-tied to the tubing of a digital pressure gauge (PASPORT Dual Pressure Sensor). The vessels were submerged in a Simulated Body Fluid (SBF)-filled container and SBF was flowed through the vessels with a syringe pump, with the pressure being monitored upstream. Lastly, a 5-French (Internal Diameter=1.7 mm) catheter was fed through the tubing to inject the shear-thinning composition directly into the vessel. The catheter was removed and the pressure was measured until ejection of the shear-thinning composition plug from the vessel. FIGS. 18A-18E show results of the ex vivo occlusion studies using porine iliac arteries and simulated body fluid to mimic whole blood.

Example 22

Sterilization Procedures (γ-Sterilization)

Figure 19A:
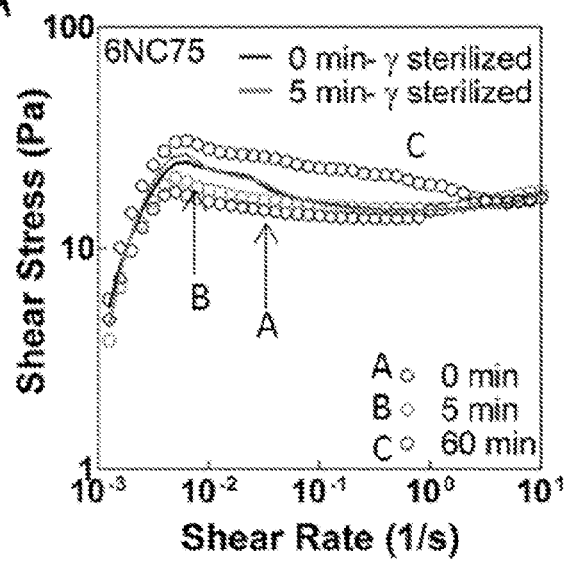
FIG. 19A shows the shear rate sweep of shear-thinning composition 6NC75 before and after gamma irradiation, which showed no significant change in the shear stress profile. (N=3; ns: P>0.05; *: P≤0.05; : P≤0.01; *: P≤0.001 determined by one-way analysis of variance with Tukey comparison for FIG. 19B).

Shear-thinning composition samples were transferred into syringes and the bottom sealed with a luer lock compatible syringe cap. Syringes were centrifuged at 3000 rpm in a swinging bucket rotor (plunger removed) to remove any bubbles and compact the shear-thinning composition. Plungers were reinserted and filled, capped syringes were placed in a plastic bag, in a glass jar filled with ice to prevent excessive heat from damaging the shear-thinning composition. The jar was placed in the irradiation chamber of a Gammacell 220E irradiator and irradiated for 6 h, resulting in a dosage of 25 kGy (69.36 gray $min^{-1}$). Shear rate sweep of the shear-thinning composition 6NC75 before and after gamma irradiation showed no significant change in the shear stress profile, as shown in FIG. 19A. Clotting time reduction of blood in contact with the shear-thinning composition was not significantly changed by gamma irradiation of the shear-thinning composition for sterilization, and addition of contrast dye (Visipaque™).

Figure 19B:
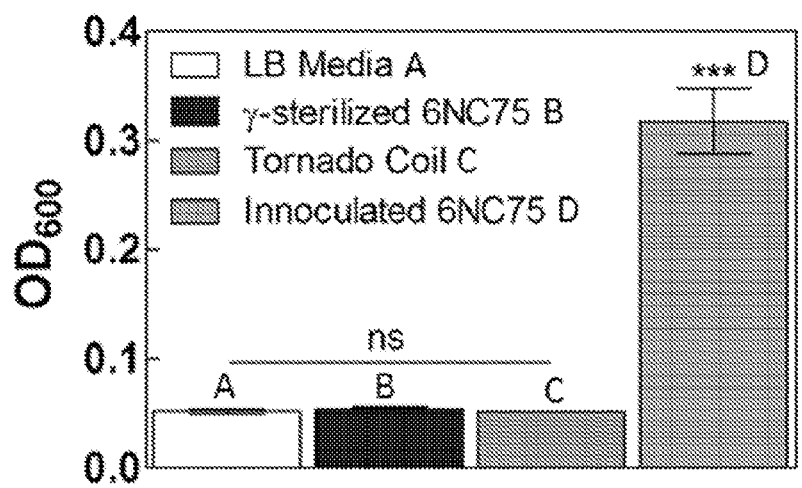
FIG. 19B shows the $OD_{600}$ of LB media incubated in shear-thinning composition-coated pipette tips for 12 h, which showed no increase in optical density of shear-thinning composition 6NC75 inoculated with *E. coli*.

Shear-thinning composition 6NC75 was inoculated with $10^7$ CFU $mL^{-1}$ BL21 Escherichia coli (E. coli) (see e.g., Trampuz et al, J. Med. Microbiol. 2006, 55:1271-1275; and Huebsch et al, J. Biomed. Mater. Res. Part B Appl. Biomater. 2005, 74B:440-447), according to a standard colony forming unit (CFU) calculation. CFU concentrations of overnight cultures were enumerated by plating serial dilutions of the culture onto LB agar plates without antibiotic. E. coli was mixed with the shear-thinning composition and separated into 2 parts: one that was placed in a sterile tube as the positive control and the other half prepared for γ-sterilization as described above. After irradiation, sterile pipette tips were used to sample the shear-thinning compositions and placed into culture tubes containing LB media. Tubes were incubated overnight (12 h) and $OD_{600}$ was measured. Serial dilutions of the overnight culture were also made in saline solution to perform the standard CFU calculation. 10 µL of each dilution was added to a LB agar plate without antibiotic and spread down the plate by tilting. The number of colonies formed at the first dilution containing between 30 and 300 colonies was used for the calculation of CFU concentration according to Equation 5:

$$CFU\ mL^{-1} = \frac{Colonies}{0.01\ mL \times 10^n} \quad \text{Equation 5}$$

where n is the dilution used for counting (e.g. 3 for a 1000 fold dilution). Samples that generated no colonies from the initial undiluted overnight culture were considered as being less than $10^2$ CFU $mL^{-1}$. $OD_{600}$ of LB media incubated in shear-thinning composition-coated pipette tips for 12 h showed no increase in optical density of 6NC75 inoculated with E. coli, as shown in FIG. 19B.

Figures 20A, 20B, 20C, 20D:
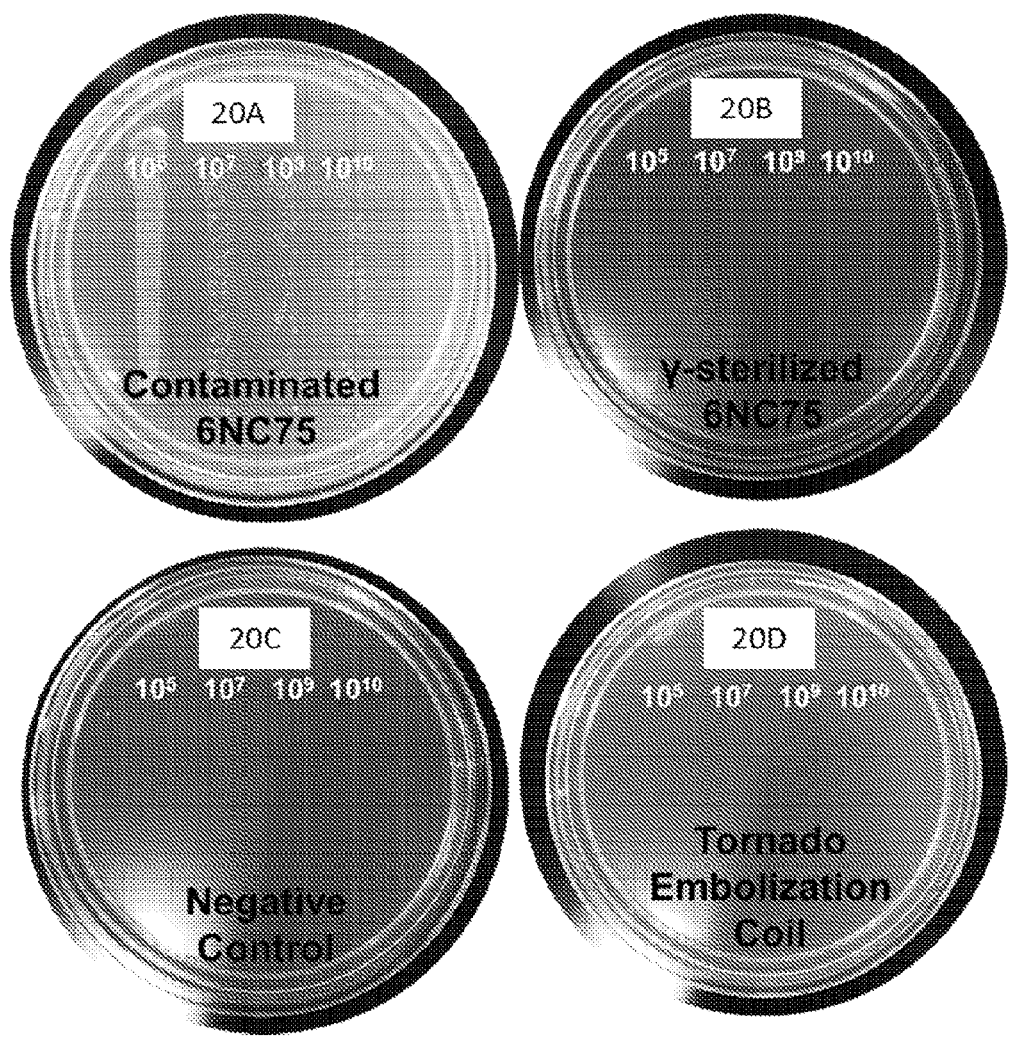
FIGS. 20A-20D show representative images of LB agar plates treated with dilutions of overnight cultures containing unsterilized inoculated shear-thinning compositions (FIG. 20A), γ-sterilized inoculated shear-thinning compositions (FIG. 20B), sterile pipette tips (negative control, FIG. 20C), and a sterile Tornado embolization coil (FIG. 20D).
Figures 21A, 21B, 21C, 21D:
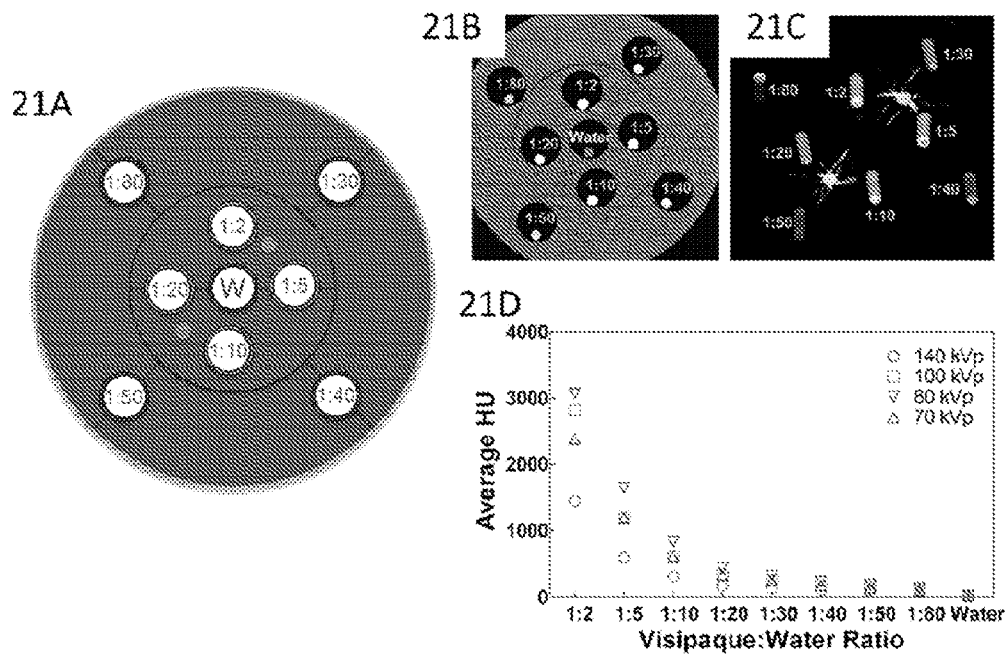
FIG. 21A shows a schematic of radiopaque shear-thinning composition syringe locations within phantom housing. Multiple ratios of Visipaque™-to-water were used to generate radiopaque shear-thinning compositions, which were subsequently imaged with different energies (kVp).
FIGS. 21B-21D show maximum intensity projections of the phantom imaging (FIGS. 21B-21C) and the dependence of Hounsfield units (HU) on energy and Visipaque™-to-water ratios. (Errors plotted are ±SD).

FIGS. 20A-20D show a visual comparison of agar plates treated with dilutions of overnight cultures containing unsterilized inoculated shear-thinning compositions (FIG. 20A), γ-sterilized inoculated shear-thinning compositions (FIG. 20B), sterile pipette tips (negative control, FIG. 20C), and a sterile Tornado embolization coil (FIG. 20D).

Example 23

Vasculature Model Testing

Shear-thinning compositions 6NC50 and 6NC75 were injected into the vessel or aneurysm of a clinical vasculature embolization model. The system was perfused manually with contrast dye (Ultravist®, Bayer) and imaged under fluoroscopy (Siemens; Artis Zeego) before and after injection of the shear-thinning composition. The shear-thinning compositions occluded the entire model vessel, delivered simply from a pre-loaded shear-thinning composition-filled syringe with no other necessary embolic preparation.

Example 24

Phantom Imaging

Shear-thinning compositions were prepared with multiple ratios of iodinated contrast dye (Visipaque™):water and added into syringes that were centrifuged to remove any bubbles in the syringe. The syringes were placed in a head and body modular phantom (Gammex 461A) and images were obtained on the same dual-energy CT scanner. Results of the phantom imaging studies are shown in FIGS. 21A-21D.

Example 25

Hematoxylin and Eosin (H&E) Staining and Mason's Trichrome (Tri) Tissue Staining Pig vessels were fixed in formalin (Sigma, HT 501128-4L, St. Louis, Mo.) for overnight at room temperature. Paraffin embedded blocks were sectioned at 8 µm and mounted on positively charged slide glass (Fisher Scientific, #12-550-15, Pittsburgh, Pa.). Slides were baked at 56° C. for 30 min, deparaffinized (2×100% Xylene, 3×100% ethanol, 1×95% ethanol, 1×80% ethanol, 1×70% ethanol, 5 min each) and rehydrated in double-distilled water for 5 min.

Slides were stained in Gill's #2 Hematoxylin solution (Sigma, GHS-216, St. Louis, Mo.) for 1 min and washed in running water for 5 min. Slides were then stained in Eosin Y (Sigma, HT110116, St. Louis, Mo.) for 1 min and washed for 5 min. Slides were dehydrated 1×in 70% ethanol, 1×80% ethanol, 1×in 95% ethanol, 1×100% ethanol for 30 s, respectively. Next, the slides were dried and mounted with permanent mounting solution (Histo Mount Solution, #008030, Life Technologies, Thermo-Fisher Scientific, Grand Island, N.Y.).

Figure 22:
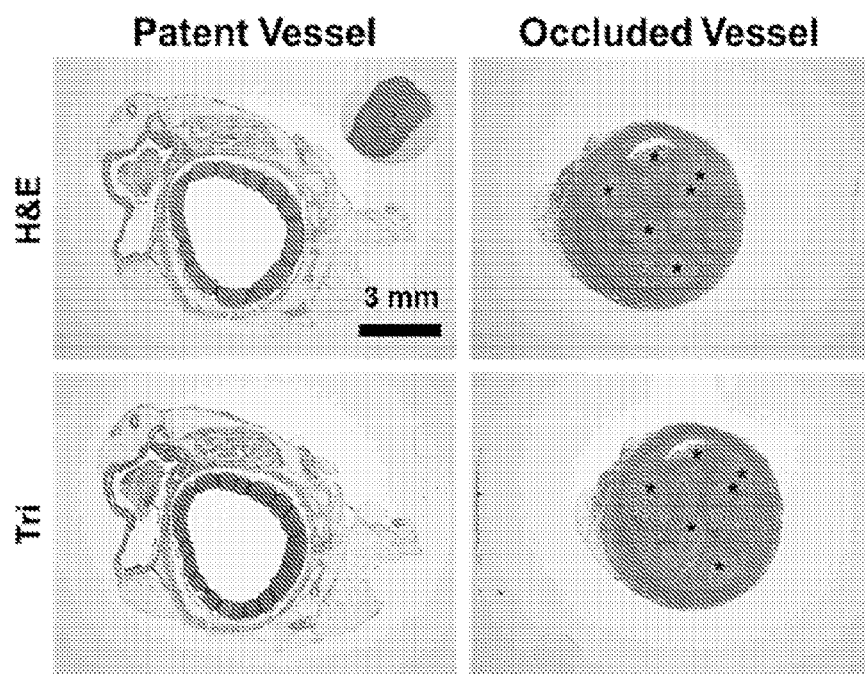
FIG. 22 shows Hematoxylin and Eosin (H&E) and Masson's Trichrome (Tri) staining of patent and occluded vessels after shear-thinning composition injection (inset in patent H&E image is H&E-stained shear-thinning composition). There was minimal remaining shear-thinning composition (asterisks), suggesting continual degradation of shear-thinning composition and replacement with dense fibrous tissue, indicative of a chronic clot.

Collagen in the vessels were stained according to Mason's Trichrome Stain Kit (Sigma HT1079, St. Louis, Mo.). Slides were stained in freshly prepared Weigert's iron Hematoxylin solution (Sigma HT15-1KT, St. Louis, Mo.) for 7 min in a humid chamber and washed in running tap water for 7 min. Then the slides were stained in Biehrich Scarlet Acid Fuchsin solution for 5 min and rinsed in phosphomolybdic-phosphotungstic acid solution for 5 s. Aniline blue solution was applied for 15 s and washed in tap water for 5 min. Slides were dried at 37° C. for 1 h and mounted with permanent mounting solution (Histo Mount Solution, #008030, Life Technologies, Thermo-Fisher Scientific, Grand Island, N.Y.). Nuclei are stained in black, cytoplasm in red and collagen in blue in the tissue. Representative images of histology staining of shear-thinning composition occluded and patent vessels are shown in FIG. 22.

Example 26

Immunohistochemistry for Myeloperoxidase (MPO), CD68 and PCNA

Antigen retrieval was performed in 10 mM sodium citrate, pH 6.0 solution (Life Technologies #005000, Thermo-Fisher Scientific, Grand Island, N.Y.). Vessel tissues were permeabilized in 0.1% Triton X-100 (Sigma T8532, St. Louis, Mo.) in PBS and endogenous peroxidase activity was quenched in 0.3% $H_2O_2$ in 60% methanol for 30 min at room temperature, respectively. Endogenous biotin activity was blocked by Avidin-Biotin Blocking Kit (Life Technologies, #004303, Thermo-Fisher Scientific, Grand Island, N.Y.). Non-specific protein was blocked in 5% goat serum in PBS for 1 h at room temperature. Polyclonal rabbit anti proliferating cell nuclear antigen (PCNA, Santa Cruz, #SC7907, 1:400, Santa Cruz, Calif.), CD68 (Aviva, ARP63008_P050, 1:400, San Diego, Calif.) and MPO (AbCam, #9535, 1:100, Cambridge, Mass.) were incubated in % goat serum for overnight at 4° C. in a humid chamber. Biotinylated goat anti-rabbit second antibody (Vector, BA4001, Burlingame, Calfi.) was applied for 1 h at room temperature. Signal was amplified with Avidin-Biotin-Complex solution (Vectastain Elite ABC kit, Vector Laboratories PK6100, Burlingame, Calif.). Permanent insoluble dark brown color (3,3'-diaminobenzidine, DAB substrate, Vector Laboratories SK4100, Burlingame, Calif.) was developed under a light microscope. Tissue sections were counterstained with Gill's #2 Hematoxylin (Sigma, GHS-216, St. Louis, Mo.) for 10 s and dehydrated and then permanently mounted.

Figures 23A, 23B, 23C, 23D:
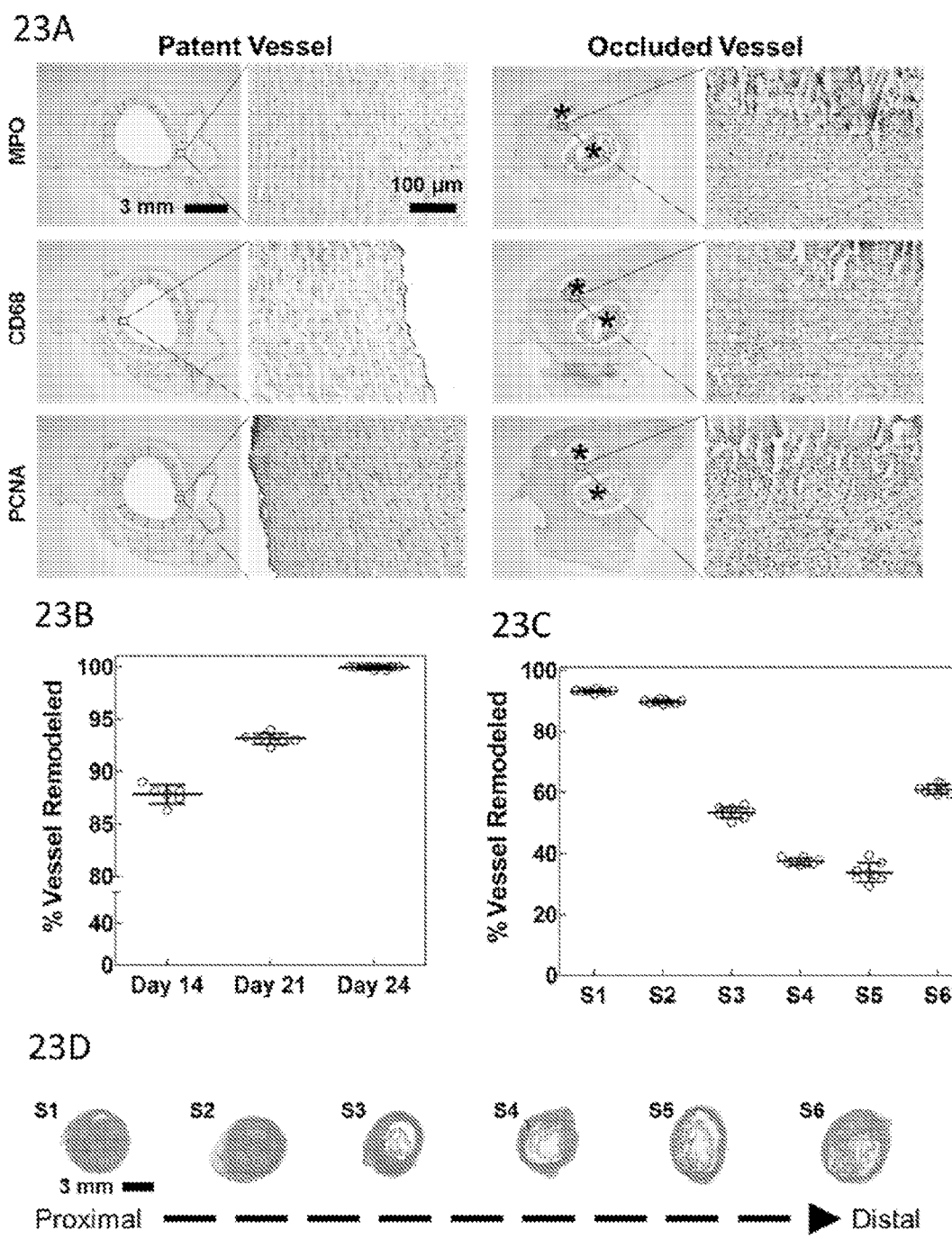
FIG. 23A shows histology staining results from patent and occluded veins after shear-thinning composition injection. Macrophages and proliferating cells were present surrounding the remaining STB. Histology sections of myeloperoxidase (MPO), CD68, and proliferating cell nuclear antigen (PCNA) showed a higher concentration of myeloid cells, macrophages, and proliferating cells surrounding the remaining shear-thinning composition (asterisks). Staining was localized to the lumen of the vessel, suggesting no systemic response to STB presence. Magnifications equal for patent and occluded vessel images.
FIG. 23B shows the replacement of the shear-thinning composition with connective tissue in the vessel, which was quantified by measuring the amount of intraluminal area filled with connective tissue from H&E histology images over time, reflecting the percentage of vessel remodeled.
FIG. 23C shows the remodeled vessel percent plotted against the histology slide's location proximal or distal to the shear-thinning composition injection. Higher levels of remodeling were noted proximal to the shear-thinning composition injection which then decreased as the sampled tissue became distal to the injection.
FIG. 23D shows the spatial dependence of vessel occlusion in histology slides sampled proximal and distal to the site of embolization.

Residual shear-thinning composition was present in the vessel with infiltrating inflammatory cells evident in the vessel lumen surrounding the remaining biomaterial. Immunohistochemistry for myeloperoxidase (MPO) revealed MPO-positive cells infiltrating the vessel luminal area. WO is known to be expressed primarily by neutrophils of the myeloid cell lineage but can also be present in monocytes and macrophages (see e.g., Klebanoff, *J. Leukoc. Biol.* 2005, 77:598-625). There was negligible WO staining observed in the vessel wall, highlighting that inflammation was confined to the lumen. Macrophages, as indicated by CD68 staining, were predominately expressed surrounding the remaining shear-thinning composition, as shown in FIG. 23A, second row), suggesting that there was ongoing degradation and clearance of residual shear-thinning composition inside the occluded vessel by phagocytic cells. In addition, there was active cellular proliferative activity, as determined by PCNA staining. The PCNA staining localized primarily to the areas of residual shear-thinning composition, suggesting that there is continued remodeling that parallels shear-thinning composition clearance within the occluded vessel lumen.

Example 27

Percent Connective Tissue in Vessel

H&E histology samples were imaged using a Zeiss Axio Zoom V16 stereomicroscope and the image files imported into ImageJ. Regions containing shear-thinning composition or unfilled with connective tissue within the intraluminal region of the vessel were outlined using the polygon tool and the area was measured (shear-thinning composition area). Next, the area of the intraluminal region of the vessel was measured (Vessel Area) and the percent vessel occluded was calculated according to Equation 6.

$$\text{Connective Tissue in Vessel (\%)} = \frac{\text{Vessel Area} - STB \text{ Area}}{\text{Vessel Area}} * 100 \quad \text{Equation 6}$$

FIG. 23B shows the replacement of shear-thinning composition with connective tissue in the vessel which was quantified by measuring the amount of intraluminal area filled with connective tissue from H&E histology images over time, reflecting the percentage of vessel remodeled. As shown in FIG. 23C, when the remodeled vessel percent was plotted against the histology slide's location proximal or distal to shear-thinning composition injection, higher levels of remodeling were noted proximal to the shear-thinning composition injection which then decreased as the sampled tissue became distal to the injection. As shown in FIG. 23D, the spatial dependence of vessel occlusion was noted in histology slides sampled proximal and distal to the site of embolization.

Clearance of the shear-thinning composition and remodeling of the embolized vessel was dependent on temporal and spatial factors (FIGS. 23B-23D). Temporally, histological sections from later time points were more advanced in their clearance of the shear-thinning composition and subsequent vessel remodeling. An increase in the percent of the vessel remodeled with connective tissue was observed, as the shear-thinning composition was cleared from the site (FIG. 23B). Spatially, comparing proximal and distal histologic cross sections of the embolized vessel, a trend toward decreased connective tissue presence was observed. There was near 100% connective tissue occupying the vessel at proximal locations and a decreased presence of connective tissue in more distal sections (FIGS. 23C-23D). The most distal section showed an increase in the presence of connective tissues relative to its adjacent more proximal sections, likely due to its proximity to the blood stream and the ability for phagocytic cells to interact with the shear-thinning composition at this extreme distal location during remodeling. The high percentage of connective tissues present at both the proximal and distal sites of occlusion result in an embolized site with minimal likelihood for subsequent fragmentation or recanalization.

Example 28

In Vivo Porcine Model

Porcine models were further tested where a shear-thinning composition (6NC75) was delivered to target vessels via standard clinical percutaneous catheterization techniques and tools. Because fragmentation and displacement of the shear-thinning composition following embolization of a target vessel is an undesired outcome, initial experiments were designed to assess stability of the injected shear-thinning composition in the arterial vasculature (FIGS. 24A-24F).

Figures 24A, 24B, 24C, 24D, 24E, 24F, 24G, 24H, 24I, 24J, 24K, 24L, 24M:
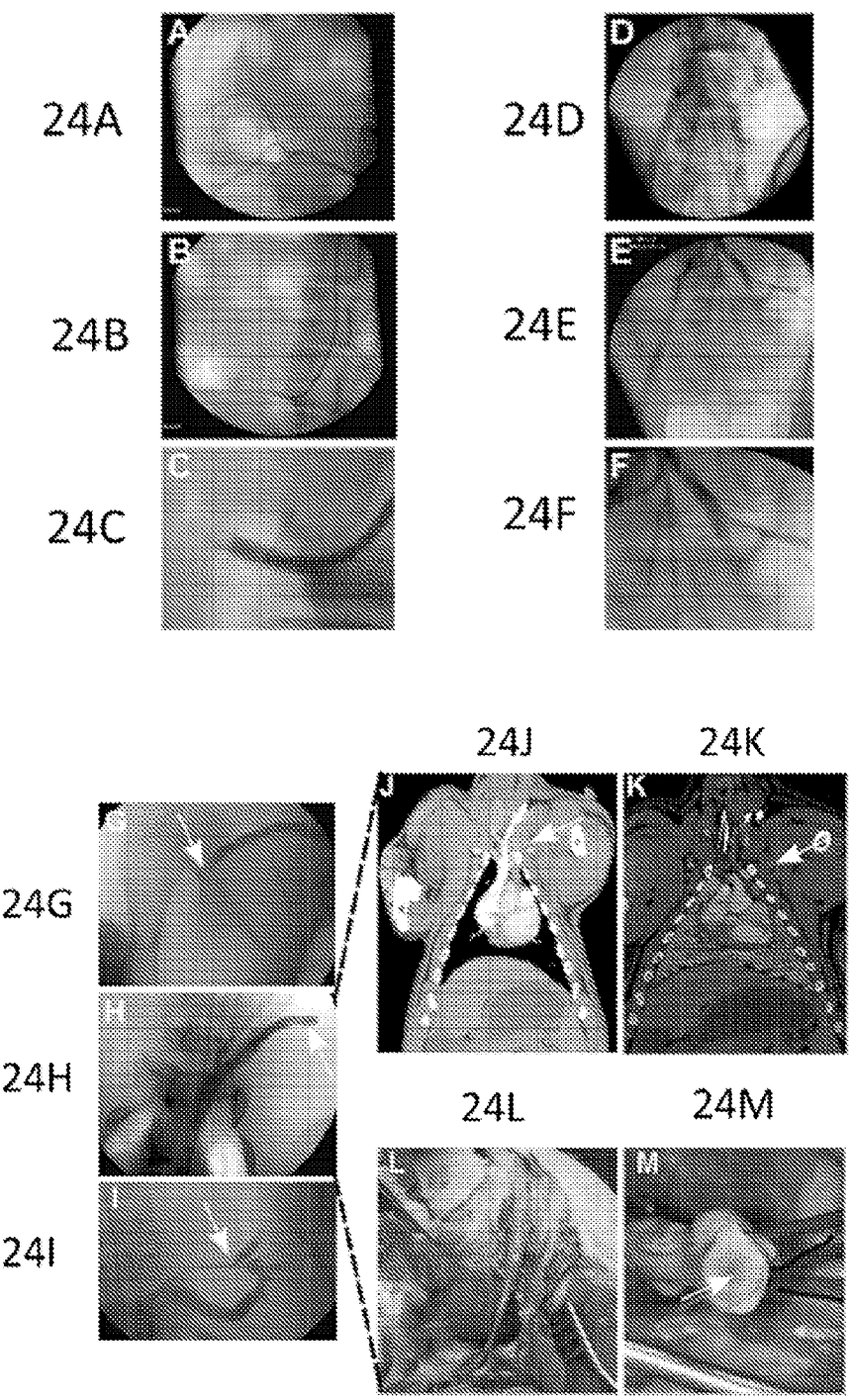
FIG. 24A shows a representative angiography image of the normal right L4 lumbar artery.
FIG. 24B shows a 5-French Cobra 2 catheter within the right L4 lumbar artery post shear-thinning composition injection; contrast injection revealed lack of opacification of the lumbar artery indicating successful embolization.
FIG. 24C shows a magnified view showing the tip of the catheter inside the lumbar artery and the abrupt cut-off of the artery indicating an impenetrable cast of the vessel and non-opacification despite high volume, high velocity contrast injection (>1000 PSI).
FIG. 24D shows digital subtraction angiography (DSA) at the level of the aortic bifurcation.
FIG. 24E shows abrupt cut-off of the left external iliac artery (EIA) following the shear-thinning composition injection.
FIG. 24F shows a magnified view of the embolized EIA.
FIGS. 24G-I show embolization of various forelimb central veins using a 5-French catheter. The white arrow in FIG. 24H indicates the same region of embolized vein shown in FIGS. 24J and 24K.
FIGS. 24J-24K shows coronal CT study at 24 days of the image shown in FIG. 24H. The CT iodine map demonstrates clear lungs without any pulmonary embolism. White arrows in FIGS. 24J and 24K indicate the same regions of embolized vein shown in FIG. 24H.
FIG. 24L shows a gross image revealing the distended, occluded vein of FIG. 24H.
FIG. 24M shows the cut surface of the shear-thinning composition occluded vein after 24 days, showing the shear-thinning composition filled within the vein.

Female Yorkshire pigs were anesthetized, intubated, and monitored throughout the procedure as described herein. Under ultrasound guidance, the right carotid artery was accessed using a standard 21 G needle and wire. Under fluoroscopic guidance, a 5-French Cobra 2 catheter (Cook Medical) and a 0.035" angled glidewire (Terumo) were brought to the infrarenal aorta and digital subtraction angiography (DSA) was performed demonstrating the lumbar arteries and the iliac arteries. The lumbar artery was catheterized and successfully embolized within seconds following the injection of approximately 1.5 mL of gamma-irradiated shear-thinning composition (6NC75) from a pre-made 3-mL syringe (FIGS. 24A-24C). FIG. 24C shows a magnified view of the shear-thinning composition edge with patent proximal lumbar artery and aorta.

Since this shear-thinning composition remained in place and did not migrate over a period of 15 min, the left external iliac artery (EIA) was embolized next. The same catheter was brought just distal to the internal iliac artery origin and approximately 4 mL of the shear-thinning composition was injected (FIGS. 24D-24F). Flow immediately ceased without any evidence for displacement or fragmentation; the shear-thinning composition remained at the injected site. This was a notable outcome because EIA is at high flow (approximately 100 cm/s) with a diameter of 7 mm, similar to the human iliac arteries; when compared to the clinical scenario, coil embolization of this high flow, large-diameter artery would be at high risk for coil displacement, which was not the case for the shear-thinning composition.

Next, the durability of shear-thinning composition embolization in the forelimb venous vasculature was tested. Forelimb veins were chosen because any fragmentation or displacement of the shear-thinning composition would lead to pulmonary embolism, an objective assessment of performance that was tested using computed tomography (CT) imaging. Using a 5-French Davis catheter (Cook Medical), various centrally positioned forelimb veins were embolized in three pigs using 3-4 mL of the gamma-sterilized shear-thinning composition 6NC75 (FIGS. 24G-24I). These pigs survived 14, 18, and 24 days. Just prior to necropsy, CT imaging was performed using a 256 slice dual-energy scanner (Definition Flash, Siemens) before and after intravenous administration of iodinated contrast media (Visipaque™). CT imaging revealed no evidence of artifact from the shear-thinning composition that would obscure the region of embolization. CT imaging also revealed that there was no evidence of any pulmonary embolism as indicated by the highly sensitive iodine maps of the lungs up to 24 days post-embolization.

Following CT imaging, the embolized veins were carefully dissected and immediately processed for histologic and immunohistochemical assessment. On gross examination, the veins were intact and occluded, with the shear-thinning composition completely filling the vein at the initial site of injection with no signs of recanalization, even after 24 days (FIGS. 24I-24J). FIGS. 24K-24M show representative images of vessel occlusion.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cancer in a subject in need thereof, comprising administering to the subject a therapeutically effective amount of a shear-thinning composition comprising gelatin or a derivative thereof and silicate nanoparticles, wherein the composition does not further comprise a chemotherapeutic agent.

2. The method of claim 1, wherein the patient is not further administered a chemotherapeutic agent.

3. The method of claim 1, wherein the shear-thinning composition comprises about 0.5 percent to about 85 percent by weight of gelatin or a derivative thereof, and silicate nanoparticles together.

4. The method of claim 1, wherein the shear-thinning composition comprises about 0.5 percent to about 20 percent by weight of the silicate nanoparticles.

5. The method of claim 1, wherein the shear-thinning composition comprises about 0.5 percent to about 70 percent by weight of the gelatin or a derivative thereof.

6. The method of claim 1, wherein the ratio of silicate nanoparticles to gelatin or a derivative thereof, is from about 0.1 to about 1.0.

7. The method of claim 1, wherein the shear-thinning composition comprises:
about 6.75 percent by weight gelatin and about 2.25 percent by weight silicate nanoparticles; or
about 4.5 percent by weight gelatin and about 4.5 percent by weight silicate nanoparticles; or
about 2.25 percent by weight gelatin and about 6.75 percent by weight silicate nanoparticles; or
about 4.5 percent by weight gelatin and about 1.5 percent by weight silicate nanoparticles; or
about 3 percent by weight gelatin and about 3 percent by weight silicate nanoparticles; or
about 1.5 percent by weight gelatin and about 4.5 percent by weight silicate nanoparticles; or
about 2.25 percent by weight gelatin and about 0.75 percent by weight silicate nanoparticles; or
about 1.5 percent by weight gelatin and about 1.5 percent by weight silicate nanoparticles; or
about 0.75 percent by weight gelatin and about 2.25 percent by weight silicate nanoparticles.

8. The method of claim 1, wherein the shear-thinning composition further comprises water.

9. The method of claim 8, wherein the shear-thinning composition comprises about 0.5 percent to about 99 percent by weight of the water.

10. The method of claim 8, wherein the shear-thinning composition comprises:
about 6.75 percent by weight gelatin, about 2.25 percent by weight silicate nanoparticles, and about 91 percent by weight water; or
about 4.5 percent by weight gelatin, about 4.5 percent by weight silicate nanoparticles, and about 91 percent by weight water; or
about 2.25 percent by weight gelatin, about 6.75 percent by weight silicate nanoparticles, and about 91 percent by weight water; or
about 4.5 percent by weight gelatin, about 1.5 percent by weight silicate nanoparticles, and about 94 percent by weight water; or
about 3 percent by weight gelatin, about 3 percent by weight silicate nanoparticles, and about 94 percent by weight water; or
about 1.5 percent by weight gelatin, about 4.5 percent by weight silicate nanoparticles, and about 94 percent by weight water; or
about 2.25 percent by weight gelatin, about 0.75 percent by weight silicate nanoparticles, and about 97 percent by weight water; or about 1.5 percent by weight gelatin, about 1.5 percent by weight silicate nanoparticles, and about 97 percent by weight water; or about 0.75 percent by weight gelatin, about 2.25 percent by weight silicate nanoparticles, and about 97 percent by weight water.

11. The method of claim 8, wherein the shear-thinning composition is a hydrogel.

12. The method of claim 1, wherein the gelatin is type-A porcine gelatin.

13. The method of claim 1, wherein the yield stress of the shear-thinning composition is from about 1 Pa to about 200 Pa.

14. The method of claim 7, wherein the shear-thinning composition comprises about 1.5 percent by weight gelatin and about 4.5 percent by weight silicate nanoparticles.

15. The method of claim 10, wherein the shear-thinning composition comprises about 1.5 percent by weight gelatin, about 4.5 percent by weight silicate nanoparticles, and about 94 percent by weight water.

* * * * *

UNITED STATES PATENT AND TRADEMARK OFFICE
CERTIFICATE OF CORRECTION

PATENT NO. : 11,083,780 B2
APPLICATION NO. : 15/746307
DATED : August 10, 2021
INVENTOR(S) : Alireza Khademhosseini and Rahmi Oklu It is certified that error appears in the above-identified patent and that said Letters Patent is hereby corrected as shown below:

On the Title Page

Item (12), delete "Khademosseini" and insert -- Khademhosseini --; and

Item (72) Inventors, delete "Ali Khademosseini" and insert -- Alireza Khademhosseini --.

Signed and Sealed this
Twenty-second Day of November, 2022

*Katherine Kelly Vidal*

Katherine Kelly Vidal
*Director of the United States Patent and Trademark Office*